US008716233B2

(12) United States Patent
Aster et al.

(10) Patent No.: US 8,716,233 B2
(45) Date of Patent: May 6, 2014

(54) NOTCH MUTATIONS LEADING TO INCREASED RECEPTOR SIGNALING

(75) Inventors: Jon C. Aster, Lexington, MA (US); Stephen C. Blacklow, Cambridge, MA (US); A. Thomas Look, North Reading, MA (US); Adolfo A. Ferrando, New York, NY (US); Andrew P. Weng, Vancouver (CA)

(73) Assignees: The Brigham and Women's Hospital, Inc., Boston, MA (US); Dana-Farber Cancer Institute, Inc., Boston, MA (US)

( * ) Notice: Subject to any disclaimer, the term of this patent is extended or adjusted under 35 U.S.C. 154(b) by 477 days.

(21) Appl. No.: 12/453,833

(22) Filed: May 22, 2009

(65) Prior Publication Data
US 2010/0087358 A1 Apr. 8, 2010

Related U.S. Application Data

(63) Continuation of application No. 11/194,913, filed on Aug. 2, 2005, now abandoned.

(60) Provisional application No. 60/598,546, filed on Aug. 4, 2004, provisional application No. 60/672,053, filed on Apr. 18, 2005.

(51) Int. Cl.
| | | |
|---|---|---|
| A61K 31/12 | (2006.01) | |
| A61K 31/21 | (2006.01) | |
| A61K 31/33 | (2006.01) | |
| A61K 31/35 | (2006.01) | |
| A61K 31/37 | (2006.01) | |
| A61K 35/02 | (2006.01) | |
| A61P 35/02 | (2006.01) | |
| C12Q 1/68 | (2006.01) | |
| G01N 33/53 | (2006.01) | |

(52) U.S. Cl.
USPC ......... 514/19.2; 514/19.6; 514/457; 514/475; 514/675; 435/6.17; 435/7.1

(58) Field of Classification Search
None
See application file for complete search history.

(56) References Cited

U.S. PATENT DOCUMENTS 6,703,221 B1 3/2004 Chan et al.

OTHER PUBLICATIONS

Rizzo et al. Rational targeting of Notch signaling in cancer. Oncogene 27: 5124-5131, 2008.*
Ferrando, AA. The role of NOTCH1 signaling in T-ALL. Hematology Am Soc Hetmaol Educ Program 2009: 353-361.*
Lee et al. Mutational analysis of Notch1, 2, 3, and 4 genes in common solid cancers and acute leukemias. APMIS 115: 1357-1363, 2007.*
Shou et al. Dynamics of notch expression during murine prostate development and tumorigenesis. Cancer Res 61: 7291-7297, 2001.*
Song et al. Cancer stem cells-an old idea that's new again: implications for the diagnsis and treatment of breast cancer. Expert Opin Biol Ther 7(4): 431438, 2007.*
Sriuranpong et al. Notch signaling induces cell cycle arrest in small cell lung cancer cells. Cancer Res 61: 3200-3205, 2001.*
Tannock and Hill. The Basic Science of Oncology. 1998. New York: McGraw-Hill, pp. 357-358.*
Tsuji et al. Radiation-induced deletions in the 5' end region of Notch1 lead to the formation of truncated proteins and are involved in the development of mouse thymic lymphomas. Carcinogenesis 24(7): 1257-1268, 2003.*
Allenspach, et al., Notch Signaling in Cancer,@ *Cancer Biol. Ther.* 1(5):466-476 (2002).
Allman, et al., Separation of Notch 1 Promoted Lineage Commitment and Expansion/Transformation in Developing T Cells,@ *J. Exp. Med.* 194:99-106 (2001).
Asnafi, et al., CALM-AF 10 is a Common Fusion Transcript in T-ALL and is Specific to the TCRγδLineage,@ *Blood* 102:1000-1006 (2003).
Aster, et al., Functional Analysis of the *TAN-1* Gene, a Human Homolog of *Drosophila notch* ,@ *Cold Spring Harbor Symp. Quant. Biol.* 59:125-136 (1994).
Aster, et al., Essential Roles for Ankyrin Repeat and Transactivation Domains in Induction of T-Cell Leukemia by Notch 1,@ *Mol. Cell. Biol.* 20:7575-7515 (2000).
Aster, "Deregulated NOTCII Signaling in Acute T-Cell Lymphoblastic Leukemia/Lymphoma: New Insights, Questions, and Opportunities," *International Journal of Hematology* 82(4):295-301 (2005).
Bellavia, et al., Constitutive Activation of NF-κB and T-Cell Leukemia/Lymphoma Notch3 in Transgenic Mice,@ *Embo J.* 19:3337-3348 (2000).
Brou, et al., A Novel Proteolytic Cleavage Involved in Notch Signaling: The Role of the Disintegrin-Mctalloprotcasc TACE,@ *Mol. Cell* 5:207-216 (2000).
Callahan, et al., Notch Signaling in Mammary Gland Tumorigenesis,@ *J. Mammary Gland Biol. Neoplasia* 6:23-36 (2001).
Calvi, et al., Osteoblastic Cells Regulate the Ilaemotopoietic Stem Cell Niche,@ *Nature* 425:841-846 (2003).
Das, et al., Notch Oncoproteins Depend on γ-Secretase/Presenilin Activity for Processing and Function,@ *J. Biol. Chem.* 279:30771-30780 (2004).
De Strooper, et al., A Presenilin-1 -Dependent γ-Secretase-Like Protease Mediates Release of Notch Intracellular Domain,@ *Nature* 398:518-522 (1999).
Ellisen, et al., A *TAN-1*, the Human Homolog of the *Drosophila notch* Gene, is Broken by Chromosomal Translocations in T Lymphoblastic Neoplasms,@ *Cell* 66:649-661 (1991).

(Continued)

*Primary Examiner* — Bridget E Bunner
(74) *Attorney, Agent, or Firm* — Law Office of: Michael A. Sanzo, LLC

(57) ABSTRACT

The present invention is based upon the identification of regions within the NOTCH-1 receptor that, when mutated, lead to increase receptor signaling. The mutations are associated with uncontrolled cellular growth and this growth may be arrested using agents that interfere with NOTCH-1 activity, such as inhibitors of gamma-secretase. Assays for the NOTCH-1 mutations may be used diagnostically or as part of a treatment regimen for cancer patients.

20 Claims, 38 Drawing Sheets

(56) References Cited

OTHER PUBLICATIONS

Feldman, et al., A Carboxy-Terminal Deletion Mutant of Notch 1 Accelerates Lymphoid Oncogenesis in E2A-PBX1 Transgenic Mice,@ Blood 96:1906-1913 (2000).

Ferrando, et al., Gene Expression Signatures Define Novel Oncogenic Pathways in T Cell Acute Lymphoblastic Leukemia,@ Cancer Cell 1:75-87 (2002).

Ferrando, et al., Prognostic Importance of TLX1 (HOX11) Oncogene Expression in Adults with T-Cell Acute Lymphoblastic Leukaemia,@ Lancet 363:535-536 (2004).

Francis, et al., alph-1 and pen-2 are Required for Notch Pathway Signaling, γ-Secretase Cleavage of βAPP, and Presenilin Protein Accumulation,@ Developmental Cell 3:85-97 (2002).

Fryer, et al., Mastermind Mediates Chromatin-Specific Transcription and Turnover of the Notch Enhancer Complex,@ Genes Dev. 16:1397-1411 (2002).

Gray, et al., "Human Ligands of the Notch Receptor," Am. J. Pathol. 154(3):785-794 (Mar. 1999).

Gridley, "Kick it up a Notch: Notch1 Activation in T-ALL," Cancer Cell 6(5):431-432 (Nov. 2004).

Gupta-Rossi, et al., Monoubiquitination and Endocytosis Direct γ-Secretase Cleavage of Activated Notch Receptor,@ J. Cell Biol. 166:73-83 (2004).

Hsieh, et al., Truncated Mammalian Notch1 Activates CBF1/RBPJk-Repressed Genes by a Mechanism Resembling That of Epstein-Barr Virus EBNA2,@ Mol. Cell. Biol. 16:952-959 (1996).

Hoemann, et al., Two Distinct Notch1 Mutant Alleles are Involved in the Induction of T-Cell Leukemia in c-myc Transgenic Mice,@ Mol. Cell. Biol. 20:3831-3842 (2000).

Kimberly, et al., Aγ-Secretase is a Membrane protein Complex Comprised of Presenilin, Nicastrin, aph-1, and pen-2,@ PNAS 100:6382-6387 (2003).

Kornilova, et al., Differential Effects of Inhibitors on the γ-Secretase Complex,@ J. Biol. Chem. 278:16470-16473 (2003).

Logeat, et al., The Notch1 Receptor is Cleaved Constitutively by a Furin-Like Convertase,@ Proc. Natl. Acad. Sci. USA 95:8108-8112 (1998).

Mumm, et al., A Ligand-Induced Extracellular Cleavage Regulates γ-Secretase-Like Proteolytic Activation of Notch1,@ Mol. Cell 5:197-206 (2000).

Nam, et al., Structural Requirements for Assembly of the CSL Intracellular Notch1 Mastermind-Like 1 Transcriptional Activation Complex,@ J. Biol. Chem. 278:21232-21239 (2003).

Öberg, et al., The Notch Intracellular Domain Is Ubiquitinated and Negatively Regulated by the Mammalian Sel-10 Homolog,@ J. Biol. Chem. 276:35847-35853 (2001).

O'Neil, et al., "Activating Notch 1 mutations in mouse models of T-ALL," Blood 107(2):781-785 (2006).

Pear, et al., "Exclusive Development of T cell Neoplasms in Mice Transplanted with Bone Marrow Expressing Activated Notch Alleles," J. Exp. Med. 183:2283-2291 (May 1996).

Pear, et al., "T cell acute lymphoblastic leukemia/lymphoma: a human cancer commonly associated with aberrant NOTCH1 signaling," Curr. Opin. Hematol. 11:426-433 (2004).

Pui, et al., Acute Lymphoblastic Leukemia, N. Engl. J. Med. 350:1535-1548 (2004).

Radtke, et al., Deficient T Cell Fate Specification in Mice with an Induced Inactivation of Notch1,@ Immunity 10:547-558 (1999).

Rand, et al., Calcium Depletion Dissociates and Activates Heterodimeric Notch Receptors,@ Mol. Cell. Biol. 20:1825-1835 (2000).

Rohn, et al., Transduction of Notch2 in Feline Leukemia Virus-Induced Thymic Lymphoma,@ J. Virol. 70:8071-8080 (1996).

Sanchez-Irizarry, et al., "Notch Subunit Heterodimerization and Prevention of Ligand-Independent Proteolytic Activation Depend, Respectively, on a Domain and the LNR Repeats," Mol. Cell Biol. 24(21):9265-9273 (Nov. 2004).

Tannock and Hill. The Basic Science of Onocology. 1998. New York: McGraw-Hill, pp. 396-397.

Wallberg, et al., p300 PCAF Act Cooperatively to Mediate Transcriptional Activation from Chromatin Templates by Notch Intracellular Domains in Vitro,@ Mol. Cell. Biol. 22:7812-7819 (2002).

Weng, et al., Growth Suppression of Pre-T Acute Lymphoblastic Leukemia Cells by Inhibition of Notch Signaling,@ Mol. Cell. Biol. 23:655-664 (2003).

Weng, et al., "Activating Mutations of Notch1 in Human T Cell Acute Lymphoblastic Leukemia," Science 306:269-271 (Oct. 2004).

Weng, et al., "Activating Mutations of Notch1 in Human T Cell Acute Lymphoblastic Leukemia (Supplement)," Science 306:269-271 (2004), Supporting online material.

Wolfe, Therapeutic Strategies for Alzheimer=s Disease,@ Nat. Rev. Drug. Discov. 1:859-866 (2002).

Wolfer, et al., Inactivation of Notch1 Impairs VDJβ Rearrangement and Allows pre-TCR-Independent Survival of Early αβ Lineage Thymocytes,@ Immunity 16:869-879 (2002).

Zhu, et al., "NOTCH 1 mutations in T-cell acute lymphblastic leukemia: prognostic significance and implication in multifactorial leukemogenesis," Clin. Cancer Res. 12(10):3043-3049 (2006).

International Search Report for PCT/US2005/027716 filed Aug. 4, 2005.

International preliminary Report on Patentability for PCT/US2005/027716 filed Aug. 4, 2005.

European Search Report for EP 05804071.8, 2008.

Moellering, et al., "Direct inhibition of the NOTCH transcription factor complex," Nature 462:182-188 (Nov. 2009) with Supplemental pages.

Real, et al., "γ-secretase inhibitors reverse glucocorticoid resistance in T cell acute lymphoblastic leukemia," Nature Medicine 15(1):50-58 (Jan. 2009).

Cullion, et al., "Targeting the Notch 1 and mTOR pathways in a mouse T-ALL model," Blood 113(24):6172-6181 (Jun. 2009).

Deangelo, et al., "A phase I clinical trial of the notch inhibitor MK-0752 in patients with T-cell acute lymphoblastic leukemia/lymphoma (T-ALL) and other leukemias," J. Clin. Oncol. 24(18S):6585 (2006).

Wei, et al., "Evaluation of Selective γ-Secretase InhibitorPF-03084014 for Its Antitumor Efficacy and Gastrointestinal Safety to Guide Optimal Clinical Trial Design," Mol. Cancer Ther. 9:1618-1628 (2010).

Weng, et al., "Growth Suppression of Pre-T Acute Lymphoblastic Leukemia Cells by Inhibition of Notch Signaling," Mol. Cell. Biol. 23(2):655-664 (2003).

Wu, et al., "Therapeutic antibody targeting of individual Notch receptors," Nature 464:1052-1057 (Apr. 2010) with Supplemental pages.

* cited by examiner

```
NOTCH1  ------------------MPPLLAPLLCLALLPALAARGPRCSQPGETCLNGGKCEAAN       41
NOTCH2  --------------MPALRPALLWALLALWLCCAAPAHALQCRDGYEPCVNEGMCVTYH       45
NOTCH3  MGLGARGRRRRRRLMALPPPPPMRALPLLLLLAGLGAAAPPCLDG-SPCANGGRCTHQQ       59
NOTCH4  ---------------MQPPSLLLLLLLLLLLCVSVVRPRGLLCGSFPEPCANGGTCLSLS      44
                          :    *  *    . . *      ..* * * *

NOTCH1  --GTEACVCGGAFVGPRCQDPNPCL-STPCKNAGTCHVVDRR----------GVADYACS     88
NOTCH2  N-GTGYCKCPEGFLGEYCQHRDPCE-KNRCQNGGTCVAQAML----------GKAT--CR     91
NOTCH3  PSLEAACLCLPGWVGERCQLEDPCH-SGPCAGRGVCQSSVVA----------GTAR----   104
NOTCH4  -LGQGTCQCAPGFLGETCQFPDPCQNAQLCQNGGSCQALLPAPLGLPSSPSPLTPSFLCT    103
             * *   .::* **  :**     * . * *

NOTCH1  CALGFSGPLCLTPLDNACLTN-PCRNGGTCDLLTLTEYKCRCPPGWSGKSCQQADPCASN    147
NOTCH2  CASGFTGEDCQYSTSHPCFVSRPCLNGGTCHMLSRDTYECTCQVGFTGKECQWTDACLSH    151
NOTCH3  -----------------------------------FSCRCLRGFQGPDCSQPDPCVSR     127
NOTCH4  CLPGFTGERCQAKLEDPCPPS-FCSKRGRCHIQASGRPQCSCMPGWTGEQCQLRDFCSAN    162
                                            .* *  *:  * .* .   * * :

NOTCH1  PCANGGQCLP-FEASYICHCPPSFHGPTCRQDVNECGQKPGLCRHGGTCHNEVGSYRCVC    206
NOTCH2  PCANGSTCTT-VANQFSCKCLTGFTGQKCETDVNECD-IPGHCQHGGTCLNLPGSYQCQC    209
NOTCH3  PCVHGAPCSVGPDGRFACACPPGYQGQSCQSDIDECR-SGTTCRHGGTCLNTPGSFRCQC    186
NOTCH4  PCVNGGVCLA-TYPQIQCHCPPGFEGHACERDVNECFQDPGPCPKGTSCHNTLGSFQCLC    221
        **. *.  *             * * .:   *  .* :** :    * :*  * **: *  *

NOTCH1  RATHTGPNCERPYVPCSPSPCQNGGTCRPTGD---VTHECACLPGFTGQNCEENIDDCPG    263
NOTCH2  PQGFTGQYCDSLYVPCAPSPCVNGGTCRQTGD---FTFECNCLPGFEGSTCERNIDDCPN    266
NOTCH3  PLGYTGLLCENPVVPCAPSPCRNGGTCRQSSD---VTYDCACLPGFEGQNCEVNVDDCPG    243
NOTCH4  PVGQEGPRCELRAGPCPPRGCSNGGTCQLMPEKDSTFHLCLCPPGFIGPGCEVNPDNCVS    281
         *  *:    **.*   ***** :         .  * *** *  ** * *:*

NOTCH1  NNCKNGGACVDGVNTYNCRCPPEWTGQYCTEDVDECQLM-PNACQNGGTCHNTHGGYNCV    322
NOTCH2  HRCQNGGVCVDGVNTYNCRCPPQWTGQFCTEDVDECLLQ-PNACQNGGTCANRNGGYGCV    325
NOTCH3  HRCLNGGTCVDGVNTYNCQCPPEWTGQFCTEDVDECQLQ-PNACHNGGTCFNLLGGHSCV    302
NOTCH4  HQCQNGGTCQDGLDTYTCLCPETWTGWDCSEDVDECEAQGPPHCRNGGTCQNSAGSFHCV    341
        :.*'***.*  **::**.  *** :** *** *:****** *  *:****** *  .. **

NOTCH1  CVNGWTGEDCSENIDDCASAACFHGATCHDRVASFYCECPHGRTGLLCHLNDACISNPCN    382
NOTCH2  CVNGWSGDDCSENIDDCAFASCTPGSTCIDRVASFSCMCPEGKAGLLCHLQDDACISNPCH    385
NOTCH3  CVNGWTGESCSQNIDDCATAVCFHGATCHDRVASFYCACPMGKTGLLCHLDDACVSNPCH    362
NOTCH4  CVSGWGGTSCEENLDDCIAATCAPGSTCIDRVGSFSCLCPPGRTGLLCHLEDMCLSQPCH    401
        **.**  *  *.:*:***   *  .:*:** ::** *.****  * *.*:**:
```

FIG. 1A

```
NOTCH1  EGSNCDTNPVNGKAICTCPSGYTGPACSQDVDECSLG---ANPCEHAGKCINTLGSFECQ  439
NOTCH2  KGALCDTNPLNGQYICTCPQGYKGADCTEDVDECAMAN--SNPCEHAGKCVNTDGAFHCE  443
NOTCH3  EDAICDTNPVSGRAICTCPPGFTGGACDQDVDECSIG---ANPCEHLGRCVNTQGSFLCQ  419
NOTCH4  GDAQCSTNPLTGSTLCLCQPGYSGPTCHQDLDECLMAQQGPSPCEHGGSCLNTPGSFNCL  461
         .: *.***:.* :* * *:.* * .*:.*** ::  ..**** * *:.** *:.* *

NOTCH1  CLQGYTGPRCEIDVNECVSNPCQNDATCLDQIGEFQCICMPGYEGVHCEVNTDECASSPC  499
NOTCH2  CLKGYAGPRCEMDINECHSDPCQNDATCLDKIGGFTCLCMPGFKGVHCELEINECQSNPC  503
NOTCH3  CGRGYTGPRCETDVNECLSGPCRNQATCLDRIGQFTCICMAGFTGTYCEVDIDECQSSPC  479
NOTCH4  CPPGYTGSRCEADHNECLSQPCHPGSTCLDLLATFHCLCPPGLEGQLCEVETNECASAPC  521
         *  **:*.*** * *** * **:   .:****  :.  * *:.* .*   **:: .** * **

NOTCH1  LHNGRCLDKINEFQCECPTGFTGHLCQYDVDECASTPCKNGAKCLDGPNTYTCVCTEGYT  559
NOTCH2  VNNGQCVDKVNRFQCLCPPGFTGPVCQIDIDDCSSTPCLNGAKCIDHPNGYECQCATGFT  563
NOTCH3  VNGGVCKDRVNGFSCTCPSGFSGSMCQLDVDECASTPCRNGAKCVDQPDGYECRCAEGFE  539
NOTCH4  LNHADCHDLLNGFQCICLPGFSGTRCEEDIDECRSSPCANGGQCQDQP-----------  569
         :: .  * *  * .*:*  * * *.** **:.*  *: :.* :.** **.:.* * *

NOTCH1  GTHCEVDIDECDPDPCHYGSCKDGVATFTCLCRPGYTGHHCETNINECSSQPCRHGGTCQ  619
NOTCH2  GVLCEENIDNCDPDPCHHGQCQDGIDSYTCICNPGYMGAICSDQIDECYSSPCLNDGRCI  623
NOTCH3  GTLCERNVDDCSPDPCHHGRCVDGIASFSCACAPGYTGIRCESQVDECRSQPCRYGGKCL  599
NOTCH4  -----------------------GAFHCKCLPGFEGPRCQTEVDECLSDPCPVGASCL  604
                                 ::  * **: *  *: :::** *.**   .. *

NOTCH1  DRDNAYLCFCLKGTTGPNCEINLDDCASSPCDSGTCLDKIDGYECACEPGYTGSMCNINI  679
NOTCH2  DLVNGYQCNCQPGTSGVNCEINFDDCASNPCIHGICMDGINRYSCVCSPGFTGQRCNIDI  683
NOTCH3  DLVDKYLCRCPPGTTGVNCEVNIDDCASNPCTFGVCRDGINRYDCVCQPGFTGPLCNVEI  659
NOTCH4  DLPGAFFCLCPS-------------------------------GFTGQLC--EV  625
         *   .  : **                                     *.**  *  ::

NOTCH1  DECAGNPCHNGGTCEDGINGFTCRCPEGYHDPTCLSEVNECNSNPCVHGACRDSLNGYKC  739
NOTCH2  DECASNPCRKGATCINGVNGFRCICPEGPHHPSCYSQVNECLSNPCIHGNCTGGLSGYKC  743
NOTCH3  NECASSPCGEGGSCVDGENGFHCLCPPGSLPPLCLPANHPCAHKPCSHGVCHDAPGGFRC  719
NOTCH4  PLCAPNLCQPKQICKDQKDKANCLCPDG--SPGCAPPEDNCT---CHHGHCQRSS----C  676
         . *  * .* :  *  :   .* ** *   ..  .    *   * ** *  .     *

NOTCH1  DCDPGWSGTNC--DINNNECESNPCVNGGTCKDMTGYVCTCREGFSGPNCQTNINECAS  797
NOTCH2  LCDAGWVGINC--EVDKNECLSNPCQNGGTCDNLVNGYRCTCKKGFKGYNCQVNIDECAS  801
NOTCH3  VCEPGWSGPRCSQSLAPDACESQPCQAGGTCTSDGIGFRCTCAPGFQGHQCEV-------  772
NOTCH4  VCDVGWTGPEC--EAELGGCISAPCAHGGTCYPQPSGYNCTCPT---------------  718
         *:. ** .*       .   * ** ****    .  :.**    *:  ***
```

FIG. 1B

```
NOTCH1  NPCLNQGTCIDDVAGYKCNCLLPYTGATCEVVLAPCAPSPCRNGGECRQSEDYESFSCVC  857
NOTCH2  NPCLNQGTCFDDISGYTCHCVLPYTGKNCQTVLAPCSPNPCENAAVCKESPNFESYTCLC  861
NOTCH3  -------------------------------LSPCTPSLCEHGGHCESDPD-RLTVCSC  799
NOTCH4  ------------------------------------------------------------

NOTCH1  PTGWQAGQTCEVDINECV-LSPCRHGASCQNTHGGYRCHCQAGYSGRNCETDIDDCRPNP  916
NOTCH2  APGWQG-QRCTIDIDECI-SKPCMNHGLCHNTQGSYMCECPPGFSGMDCEEDIDDCLANP  919
NOTCH3  PPGWQG-PRCQQDVDECAGASPCGPHGTCTNLPGNFRCICHRGYTGPFCDQDIDDCDPNP  858
NOTCH4  ---------------------------------------GYTGPTCSEEMTACHSGP    736
                                                *::* *. :: * ..*

NOTCH1  CHNGGSCTDGINTAFCDCLPGFRGTFCEEDINECASDPCRNGANCTDCVDSYTCTCPAGF  976
NOTCH2  CQNGGSCMDGVNTFSCLCLPGFTGDKCQTDMNECLSEPCKNGGTCSDYVNSYTCKCQAGF  979
NOTCH3  CLHGGSCQDGVGSFSCSCLDGFAGPRCARDVDECLSSPCGPG-TCTDHVASFTCACPPGY  917
NOTCH4  CLNGGSCNPSPGGYYCTCPPSHTGPQCQTSTDYCVSAP----------------------  774
        * :****   ..   * *   ..  *   *  :  * * *

NOTCH1  SGIHCENNTPDCTESSCFNGGTCVDGINSFTCLCPPGFTGSYCQHDVN-ECDSQPCLHGG  1035
NOTCH2  DGVHCENNINECTESSCFNGGTCVDGINSFSCLCPVGFTGSFCLHEIN-ECSSHPCLNEG  1038
NOTCH3  GGFHCEIDLPDCSPSSCFNGGTCVDGVSSFSCLCRPGYTGTHCQYEAD-PCFSRPCLHGG  976
NOTCH4  ---------------CFNGGTCVNRPGTFSCLCAMGFQGPRCEGKLRPSCADSPCRNRA  818
                       ********:  :*:*** *:. *.  *      *  **  :

NOTCH1  TCQDGCGSYRCTCPQGYTGPNCQNLVHWCDSSPCKNGGKCWQTHTQYRCECPSGWTGLYC  1095
NOTCH2  TCVDGLGTYRCSCPLGYTGKNCQTLVNLCSRSPCKNKGTCVQKKAESQCLCPSGWAGAYC  1098
NOTCH3  ICNPTHPGFECTCREGFTGSQCQNPVDWCSQAPCQNGGRCVQTG--AYCICPPGWSGRLC  1034
NOTCH4  TCQDSPQGPRCLCPTGYTGGSCQTLMDLCAQKPCPRNSHCLQTGPSFHCLCLQGWTGPLC  878
        *        .* *  *:** **  :  *   **     .   *    * *  **:* *

NOTCH1  DVPSVSCEVAAQRQGVDVARLCQHGGLCVDAGNTHHCRCQAGYTGSYCEDLVDECSPSPC  1155
NOTCH2  DVPNVSCDIAASRRGVLVEHLCQHSGVCINAGNTHYCQCPLGYTGSYCEEQLDECASNPC  1158
NOTCH3  DIQSLPCTEAAAQMGVRLEQLCQEGGKCIDKGRSHYCVCPEGRTGSHCEHEVDPCTAQPC  1094
NOTCH4  NLPLSSCQKAALSQGIDVSSLCHNGGLCVDSGPSYFCHCPPGFQGSLCQDHVNPCESRPC  938
         :     .*  **  *:  :  **...* *::  * ::.* *   *  **  :: * .**

NOTCH1  QNGATCTDYLGGYSCKCVAGYHGVNCSEEIDECLSHPCQNGGTCLDLPNTYKCSCPRGTQ  1215
NOTCH2  QHGATCSDFIGGYRCECVPGYQGVNCEYEVDECQNQPCQNGGTCIDLVNHFKCSCPPGTR  1218
NOTCH3  QHGGTCRGYMGGYVCECPAGYAGDSCEDNIDECASQPCQNGGSCIDLVARYLCSCPPGTL  1154
NOTCH4  QNGATCMAQPSGYLCQCAPGYDGQNCSKELDACQSQPCHN--------------------  978
        *:*.**      ** *:* .*  *.* *. *  *.  :: *  .:**.*
```

FIG. 1C

```
NOTCH1  GVHCEINVDDCNPPVDPVSRSPKCFNNGTCVDQVGGYSCTCPPGFVGERCEGDVNECLSN  1275
NOTCH2  GLLCEENIDDC-------ARGPHCLNGGQCMDRIGGYSCRCLPGFAGERCEGDINECLSN  1271
NOTCH3  GVLCEINEDDCDLG-PSLDSGVQCLHNGTCVDLVGGFRCNCPPGYTGLHCEADINECRPG  1213
NOTCH4  ----------------------HGTCTPKPGGFHCACPPGFVGLRCEGDVDECLDQ      1012
               *  **. * * **:.* :**.*::**

NOTCH1  PCDARGTQNCVQRVN-DFHCECRAGHTGRRCESVINGCKGKPCKNGGTCAVASNTARG--  1332
NOTCH2  PCSSEGSLDCIQLTN-DYLCVCRSAFTGRHCETFVDVCPQMPCLNGGTCAVASNMPDG--  1328
NOTCH3  ACHAAHTRDCLQDPGGHFRCVCHPGFTGPRCQIALSPCESQPCQHGGQCRHSLGRGGGLT  1273
NOTCH4  PCHPTGTAACHSLAN-AFYCQCLPGHTGQWCEVEIDPCHSQPCFHGGTCEATAGSPLG--  1069
         .*   :  *  .  .:  ** ...** *:  :.*   ** :**  *  : .    *

NOTCH1  FICKCPAGFEGATCENDARTCGSLRCLNGGTCISGPRS---PTCLCLGPFTGPECQFPAS  1389
NOTCH2  FICRPPGFSGARCQS---SCGQVKCRKGEQCVHTASG---PRCFCPSPRD---CESGCA  1379
NOTCH3  FTCHCVPPFWGLRCERVARSCRELQCPVGIPCQQTARG---PRCACPPGLSGPSCRVSRA  1330
NOTCH4  FICHCPKGFEGPTCSHRAPSCGFHHCHHGGLCLPSPKPGFPPRCACLSGYGGPDCLTPPA  1129
         * *:*   * * *.   :* :* * *     *** *          *

NOTCH1  SPC------LGGNPCYNQGTCEPTS--ESPFYRCLCPAKFNGLLCHILDYSFGGGAGRDI  1441
NOTCH2  S----------SPCQHGGSCHPQR--QPPYYSCQCAPPFSGSRCELYT----------A  1416
NOTCH3  SPSGATNASCASAPCLHGGSCLPVQ--SVPFFRCVCAPGWGGPRCETPS----------AA  1379
NOTCH4  PKG-----CGPPSPCLYNGSCSETTGLGGPGFRCSCPHSSPGPRCQKPG-----------  1173
                **  *:* *       * : **.   * *.

NOTCH1  PPPLIEEACELPECQEDAGNKVCSLQCNNHACGWDGGDCSLNFNDPWKNCTQSLQCWKYF  1501
NOTCH2  PPSTPPATCLSQYCADKARDGVCDEACNSHACQWDGGDCSLTMENPWANCSSPLPCWDYI  1476
NOTCH3  PEVPEEPRCPRAACQAKRGDQNCDRECNTPGCGWDGGDCSLNVDDPWRQC-EALQCWRLF  1438
NOTCH4  ---------AKGCEGRSGDGACDAGCSGPGGNWDGGDCSLGVPDPWKGCPSHSRCWLLF  1223
                   *    : *. *.  .  ********  :**  *     **  :

NOTCH1  SDGHCDSQCNSAGCLFDGFDCQ--RAEGQCNPLYDQYCKDHFSDGHCDQGCNSAECEWDG  1559
NOTCH2  NN-QCDELCNTVECLFDNFECQ--GNSKTCK--YDKYCADHFKDNHCDQGCNSEECGWDG  1531
NOTCH3  NNSRCDPACSSPACLYDNFDCYSGGRDRTCNPVYEKYCADHFADGRCDQGCNTEECGWDG  1498
NOTCH4  RDGQCHPQCDSEECLFDGYDCE---TPPACTPAYDQYCHDHFHNGHCEKGCNTAECGWDG  1280
         : *.  *.: **:*.::*       *. *::**  *** :..*::***: ** ***

NOTCH1  LDCAEHVPERLAAGTLVVVVLMPPEQLRNSSFHFLRELSRVLHTNVVFKRDAHGQQMIFP  1619
NOTCH2  LDCAADQPENLAEGTLVIVVLMPPEQLLQDARSFLRALGTLLHTNLRIKRDSQGELMVYP  1591
NOTCH3  LDCASEVPALLARGVLVLTVLLPPEELLRSSADFLQRLSAILRTSLRFRLDARGQAMVFP  1558
NOTCH4  GDCRPEDGDPEWGPSLALLVVLSPPALDQQLFALARVLSLTLRVGLWVRKDRDGRDMVYP  1340
         **   .  *  * .*:. *::* *.    : *.  *:. ::.  : * *. *:.*
```

FIG. 1D

```
NOTCH1  YYGREEELRKHPIKRAAEGWAAPDALLGQVKASLLPGGSEGGRRRRELDPMDVRGSIVYL 1679
NOTCH2  YYGEKSAAMKK---------------QRMTRRSLPGEQE----------QEVAGSKVFL 1625
NOTCH3  YHRPSPGSESR------------------VRRELGP--------------EVIGSVVML 1585
NOTCH4  YPGARAEEKLG-----------GTRDPTYQERAAPQTQPLG----KETDSLSAGFVVVM 1384
                *                           *                  *  * :

NOTCH1  EIDNRQCVQ--ASSQCFQSATDVAAFLGALASLGSLN--IPYKIEAVQSETVEPPPPAQL 1735
NOTCH2  EIDNRQCVQ--DSDHCFKNTDAAAALLASHAIQGTLS--YP--LVSVVSESLTP---ERT 1676
NOTCH3  EIDNRLCLQSAENDHCFPDAQSAADYLGALSAVERLD--FPYPLRDVRGEPLEAPE-QSV 1642
NOTCH4  GVDLSRCGPDHPASRCPWDPGLLLRFLAAMAAVGALEPLLPGPLLAVHPHAGTAPPANQL 1444
         :*    *      .:*  ..    *.: :   *.  *    : *    ..   .

NOTCH1  HFMYVAAAAFVLLFFVG---CGVLLSRKRRRQHGQLWFPEGFKVS---EASKKKRREPLG 1789
NOTCH2  QLLYLLAVAVVIILFII---LLGVIMAKRKRKHGSLWLPEGFTLRR--DASNHKRREPVG 1731
NOTCH3  PLLPLLVAGAVFLLIIF---ILGVMVARRKREHSTLWFPEGFALHKDIAAGHKGRREPVG 1699
NOTCH4  PWPVLCSPVAGVILLALGALLVLQLIRRRREHGALWLPPGFTRRPRTQSAPHRRRPPLG 1504
            :     .:::     :  :*:*:*, **.* **         :. :** *:*

NOTCH1  EDSVGLKPLKN-ASDGALMDDNQNE--WGDEDLETKKFRFEEPVVLPDLDDQTDHRQWTQ 1846
NOTCH2  QDAVGLKNLSVQVSEANLIGTGTSEHWVDDEGPQPKKVKAEDEALLSEEDDPIDRRPWTQ 1791
NOTCH3  QDALGMKNMAKGESLMGEVVTDLND----SECPEAKRLKVEEPGMGAE--EPEDCRQWTQ 1753
NOTCH4  EDSIGLKALKPKAEVDEDGVVMCSGPE-----------EGEEVGQAEETGPPSTCQLWS- 1552
         :*::*:*  :    .     .     .       *:      :      : *:

NOTCH1  QHLDAADLR-MSAMAPTPPQGEVDADCMDVNVRGPDGFTPLMIASCSGGGLE-TGNSEE- 1903
NOTCH2  QHLEAADIRRTPSLALTPPQAEQEVDVLDVNVRGPDGCTPLMLASLRGGSSD-LSDEDED 1850
NOTCH3  HHLVAADIRVAPATALTPPQGDADADGVDVNVRGPDGFTPLMLASFCGGALEPMPAEEDE 1813
NOTCH4  --LSGGCGALPQAAMLTPPQ-ESEMEAPDLDTRGPDGVTPLMSAVCCG---EVQSGTFQG 1606
           *   ..    :    ****  :  :   *: ****** ****  *        :

NOTCH1  -EEDAPAVISDFIYQGASLHNQTDRTGETALHLAARYSRSDAAKRLLEASADANIQDNMG 1962
NOTCH2  AEDSSANIITDLVYQGASLQAQTDRTGEMALHLAARYSRADAAKRLLDAGADANAQDNMG 1910
NOTCH3  ADDTSASIISDLICQGAQLGARTDRTGETALHLAARYARADAAKRLLDAGADTNAQDHSG 1873
NOTCH4  AWLGCPEPWEPLLDGGACPQAHTVGTGETPLHLAARFSRPTAARRLLEAGANPNQPDRAG 1666
           ..          ::   **     :* *** .******::*.**.***:*.* * *

NOTCH1  RTPLHAAVSADAQGVFQILIRNRATDLDARMHDGTTPLILAARLAVEGMLEDLINSHADV 2022
NOTCH2  RCPLHAAVAADAQGVFQILIRNRVTDLDARMNDGTTPLILAARLAVEGMVAELINCQADV 1970
NOTCH3  RTPLHTAVTADAQGVFQILIRNRSTDLDARMADGSTALILAARLAVEGMVEELIASHADV 1933
NOTCH4  RTPLHAAVAADAREVCQLLLRSRQTAVDARTEDGTTPLMLAARLAVEDLVEELIAAQADV 1726
        * ***.**.***.  * .* .* .:.:*** :**:* *:********::: :**  :***
```

FIG. 1E

```
NOTCH1  NAVDDLGKSALHWAAAVNNVDAAVVLLKNGANKDMQNNREETPLFLAAREGSYETAKVLL 2082
NOTCH2  NAVDDHGKSALHWAAAVNNVEATLLLLKNGANRDMQDNKEETPLFLAAREGSYEAAKILL 2030
NOTCH3  NAVDELGKSALHWAAAVNNVEATLALLKNGANKDMQDSKEETPLFLAAREGSYEAAKLLL 1993
NOTCH4  GARDKWGKTALHWAAAVNNARAARSLLQAGADKDAQDNREQTPLFLAAREGAVEVAQLLL 1786
         .*.*. **.:**********.  *:   **:  **::* *:..:*.**********:  *.*::**

NOTCH1  DHFANRDITDHMDRLPRDIAQERMHHDIVRLLDEYNLVRSPQLHGAPLGGTPTLSPPLCS 2142
NOTCH2  DHFANRDITDHMDRLPRDVARDRMHHDIVRLLDEYNVTPSP--PGTVL--TSALSPVICG 2086
NOTCH3  DHLANREITDHLDRLPRDVAQERLHQDIVRLLDQPSGPRSPS-------GPHGLGPLLCP 2046
NOTCH4  GLGAARELRDQAGLAPADVAHQRNHWDLLTLLEG-------------------------- 1820
         .  * *::  *:.   * *:*::*  * *::  **:

NOTCH1  PNGYLGSLKPGVQG-KKVRKPSSK-----GLACGSKEAKDLK-ARRKKSQDGKGCLLDSS 2195
NOTCH2  PNRSFLSLKHTPMG-KKSRRPSAKSTMPTSLPNLAKEAKDAKGSRRKKSLSEKVQLSESS 2145
NOTCH3  PGAFLPGLKAVQSGTKKSRRPPGK---------TGLGPQGTRGRGKKLTLACPGPLADSS 2097
NOTCH4  -----------AGPPEARHKATP-----------------GREAGPFPRARTVSVS 1848
                 *  :  *:.                                ::        . *

NOTCH1  GMLSPVDSLESPHGYLSDVASPPLLPSP-FQQSPSVPLNHLPGMPDTHLGIGHLNVAAKP 2254
NOTCH2  VTLSPVDSLESPHTYVSDTTSSPMITSPGILQASPNPMLATAAPPAPVHAQHALSFSNLH 2205
NOTCH3  VTLSPVDSLDSPRPFSGPPASP-----------GGFPLEGPYATTATAVSLAQLGASRAG 2146
NOTCH4  VPPHGGGALPRCRTLSAGAGPR----------GGGACLQARTWSVDLAARGGGAYSHCR 1897
         ..:*       :   *.    .                    .             :

NOTCH1  EMAALGGGGRLAFETGPPRLSHLPVASGTSTVLGSSSGGALNFTVGGSTSLNGQCEWLSR 2314
NOTCH2  EMQPLAHGASTVLPSVSQLLSHHHIVS-----PGSGSAGSLSR----LHPVPVPADWMNR 2256
NOTCH3  PLGRQPPGGCVLSFG------------------------------LLNPVAVPLDWAR- 2174
NOTCH4  SLSGVGAGG--------------------------------------------------- 1906
         :              *.

NOTCH1  LQSGMVPNQYNPLRGSVAPGPLSTQAPSLQHGMVGPLHSSLAASALSQMMSYQGLPSTRL 2374
NOTCH2  MEVNET--QYNEMFGMVLAPAEGTHP-----GIA---------------------PQSRP 2288
NOTCH3  --------------------------------------------------------LPPPA 2179
NOTCH4  --------------------------------------------------------GPT 1909

NOTCH1  ATQPHLVQTQQVQPQNLQMQQQNLQPANIQQQQSLQPPPPPPQPHLGVSSAASGHLGRSF 2434
NOTCH2  PEGKHITTPREPLPPIVTFQ-------LIPKGSIAQPAGAPQPQSTCPPAVAGPLPTMY 2340
NOTCH3  PPGPSFLLPLAPGPQ-------------LLNPGAPVSPQERPPPYLAAPGHG-------- 2218
NOTCH4  PRGRRFSAGMR--------------------GPRPNPAIMRGRYG-------- 1934
         . :                               * *
```

FIG. 1F

```
NOTCH1  LSGEPSQADVQPLGPSSLAVHTILPQESPALPTSLPSSLVPPVTAAQFLTPPSQHSYSSP 2494
NOTCH2  QIP-----EMARLPSVAFPTAMMPQQDGQVAQTILPAYHPFPASVGKYPTPPSQHSYASS 2395
NOTCH3  -------EEYPAAGTRSSPTKARFLRVPSEHPYLTPSPESPEHWASPSPPSLSDWSDSTP 2271
NOTCH4  --------------------------------------------VAAGRGGRVSTDDWPCD 1951
                                                    ..        *   . .

NOTCH1  --VDNTPSHQLQVP-EHPFLTPSPESPDQWSSSSPHSNVSDWSEGVSSPPTSMQSQIARI 2551
NOTCH2  NAAERTPSHSGHLQGEHPYLTPSPESPDQWSSSSPHS-ASDWSDVTTSPTPGGAGGGQRG 2454
NOTCH3  SPATATNATASGALPAQPHPISVPSLPQSQTQLGPQPEVTPKRQVMAZ------------ 2319
NOTCH4  WVALGACGSASNIPIPPPCLTPSPERGSPQLDCGPPALQEMPINQGGEGKK--------- 2002
         . :            *  . *.   . . *   :

NOTCH1  PEAFK------------ 2556
NOTCH2  PGTHMSEPPHNNMQVYA 2471
NOTCH3  -----------------
NOTCH4  -----------------
```

FIG. 1G

```
              1571                                                        1618
human   NOTCH1  AAGTLVVVVLMPPEQLRNSSFHFLRELSRVLHTNVVFKRDAHGQQMIF   SEQ ID NO:5
rat     notch1  AAGTLVLVVLLPPDQLRNNSFHFLRDVSAVLHTNVVFKRDAHGQQMIF   SEQ ID NO:6
mouse   notch1  AAGTLVLVVLLPPDQLRNNSFHFLRELSAVLHTNVVFKRDAHGQQMIF   SEQ ID NO:7
chicken notch1  ADGTLV VVLITPENLKNNSFNFLRELSRVLHTNVVFKKNAHGQQMIF   SEQ ID NO:8
frog    notch1  AEGTLVLVVLMPPERLKNNSVNFLRELSRVLHTNVVFKKDAHGQQMIF   SEQ ID NO:9
fish    notch1  AVGLLVVVVAIHPDQLRNNSFGFLRELSRVLHTNVVFRRDAHGQQMIF   SEQ ID NO:10
consensus       A-G-LV-VV---P--L-N-S--FLR--S-VLHTNVVF--DAHGQQMIF   SEQ ID NO:11
```

FIG. 3A

| | 1571 | 1618 | |
|---|---|---|---|
| human NOTCH1 | AAGTLVVVVLMPPEQLRNSSFHFLRELSRVLHTNVVFKRDAHGQQMIF | | SEQ ID NO:5 |
| KOPTK1 | AAGTLVVVVLMPPEQLRNSSFHFLRELSRVLHTNVVFKRDAHGQQMIF | | SEQ ID NO:12 |
| TALL 07 | AAGTLVVVVLMPPEQLRNSSFHFLRELSRVLHTNVVFKRDAHGQQMIF | | SEQ ID NO:12 |
| TALL 40 | AAGTLVVVVLMPPEQLRNSSFHFLRELSRVAHTNVVFKRDAHGQQMIF | | SEQ ID NO:12 |
| TALL 41 | AAGTLVVVVLMPPEQLRNSSFHFLRELSRVAHTNVVFKRDAHGQQMIF | | SEQ ID NO:12 |
| TALL 47 | AAGTLVVVVLMPPEQLRNSSFHFLRELSRVAHTNVVFKRDAHGQQMIF | | SEQ ID NO:12 |
| TALL 68 | AAGTLVVVVLMPPEQLRNSSFHFLRELSRVAHTNVVFKRDAHGQQMIF | | SEQ ID NO:12 |
| TALL 83 | AAGTLVVVVLMPPEQLRNSSFHFLRELSRVAHTNVVFKRDAHGQQMIF | | SEQ ID NO:12 |
| ALL-SIL | AAGTLVVVVLMPPEQLRNSSFHFLRELSRVAHTNVVFKRDAHGQQMIF | | SEQ ID NO:12 |
| DND-41 | AAGTLVVVVLMPPEQLRNSSFHFARELSRVLHTNVVFKRDAHGQQMIF | | SEQ ID NO:13 |
| TALL 12 | AAGTLVVVVLMPPEQLRNSSFHFARELSRVLHTNVVFKRDAHGQQMIF | | SEQ ID NO:13 |
| TALL 18 | AAGTLVVVVLMPPEQLRNSSFHFARELSRVLHTNVVFKRDAHGQQMIF | | SEQ ID NO:13 |
| TALL 44 | AAGTLVVVVLMPPEQLRNSSFHFARELSRVLHTNVVFKRVAHGQQMIF | | SEQ ID NO:14 |
| TALL 45 | AAGTLVVVVLMPPEQLRNSSFHFARELSRVLHTNVVFKRDAHGQQMIF | | SEQ ID NO:13 |
| TALL 55 | AAGTLVVVVLMPPEQLRNSSFHFLRELSPVLHTNVVFKRDAHGQQMIF | | SEQ ID NO:15 |
| TALL 64 | AAGTLVVVVLMPPEQLRNSSFHFLRELSPVLHTNVVFKRDAHGQQMIF | | SEQ ID NO:15 |
| TALL 87 | AAGTLVVVVLMPPEQLRNSSFHFLRELSPVLHTNVVFKRDAHGQQMIF | | SEQ ID NO:15 |
| TALL 89 | AAGTLVVVVLMPPEQLRNSSFHFLRELSPVLHTNVVFKRDAHGQQMIF | | SEQ ID NO:15 |
| TALL 91 | AAGTLVVVVLMPPEQLRNSSFHFLRELSPVLHTNVVFKRDAHGQQMIF | | SEQ ID NO:15 |
| HPB-ALL | AAGTPVVVVLMPPEQLRNSSFHFLRELSRVLHTNVVFKRDAHGQQMIF | | SEQ ID NO:16 |
| TALL 03 | AAGTPVVVVLMPPEQLRNSSFHFLRELSRVLHTNVVFKRDAHGQQMIF | | SEQ ID NO:16 |
| TALL 79 | AAGTPVVVVLMPPEQLRNSSFHFLRELSRVLHTNVVFKRDAHGQQMIF | | SEQ ID NO:16 |
| TALL 96 | AAGTPVVVV-LMPPEQLRNSSFHFLRELSRVLHTNVVFKRDAHGQQMIF | | SEQ ID NO:16 |
| TALL 05 | AAGTLVVV-LMPPEQLRNSSFHFLRELSRVLHTNVVFKRDAHGQQMIF | | SEQ ID NO:17 |

FIG.3B-1

| | 1571 | 1618 | |
|---|---|---|---|
| TALL 21 | AAGTLVVV-LMPPEQLRNSSFHFLRELSRVLHTNVVFKRDAHGQQMIF | | SEQ ID NO:17 |
| TALL 23 | AAGTLVVV-LMPPEQLRNSSFHFLRELSRVLHTNVVFKRDAHGQQMIF | | SEQ ID NO:17 |
| TALL 93 | AAGTLVVV-LMPPEQLRNSSFHFLRELSRVLHTNVVFKRDAHGQQMIF | | SEQ ID NO:17 |
| TALL 30 | AAGTLVVVVLMPPEQLRNSSFHSLRELSRVLHTNVVFKRDAHGQQMIF | | SEQ ID NO:18 |
| TALL 04 | AAGTLVVVVLMPPEQ*P*RNSSFHFLRELSRVLHTNVVFKRDAHGQQMIF | | SEQ ID NO:19 |
| TALL 76 | AAGTLVVVVLMPPEQLRNSSFHFLRELSRVLH*T*NVVFK*S*DAHGQQMIF | | SEQ ID NO:20 |
| TALL 02 | AAGTLVVVVLMPPEQLRNSSFHFLRELSRVLHTNV-FKRDAHGQQMIF | | SEQ ID NO:21 |
| TALL 42 | AAGTLVVVVLMPPEQLRNSSFHFLRELSRVLHTNVVFK*T*--HGQQMIF | | SEQ ID NO:22 |
| TALL 04.1 | AAGTLV*E*VLMPPEQLRNSSFHFLRELSRVLHTNVVFKRDAHGQQMIF | | SEQ ID NO:102 |
| TALL 04.2 | AAGTLVV*E*VLMPPEQLRNSSFHFLRELSRVLHTNVVFKRDAHGQQMIF | | SEQ ID NO:103 |
| TALL 04.3 | AAGTLVVV*G*LMPPEQLRNSSFHFLRELSRVLHTNVVFKRDAHGQQMIF | | SEQ ID NO:104 |
| TALL 04.4 | AAGTLVVVVLMPPEQ*P*RNSSFHFLRELSRVLHTNVVFKRDAHGQQMIF | | SEQ ID NO:105 |
| TALL 04.5 | AAGTLVVVVLMPPEQ*Q*RNSSFHFLRELSRVLHTNVVFKRDAHGQQMIF | | SEQ ID NO:106 |
| TALL 04.6 | AAGTLVVVVLMPPVQLRNSSFHFLRELSRVLHTNVVFKRDAHGQQMIF | | SEQ ID NO:107 |
| TALL 04.7 | AAGTLVVVVLMPPEQLRNSSFHFLRE*P*SRVLHTNVVFKRDAHGQQMIF | | SEQ ID NO:108 |
| TALL 04.8 | AAGTLVVVVLMPPEQLRNSSFHFLRE*H*SRVLHTNVVFKRDAHGQQMIF | | SEQ ID NO:109 |
| TALL 04.9 | AAGTLVVVVLMPPEQLRNSSFHFLREL*T*RVLHTNVVFKRDAHGQQMIF | | SEQ ID NO:110 |
| TALL 04.10 | AAGTLVVVVLMPPEQLRNSSFHFLRELSRVLHM*W*VFKRDAHGQQMIF | | SEQ ID NO:111 |
| TALL 04.11 | AAGTLVVVVLMPPEQLRNSSFHFLRELSRVLHTN*E*VFKRDAHGQQMIF | | SEQ ID NO:112 |
| TALL 04.12 | AAGTLVVVVLMPPEQLRNSSFHFLRELSRVLHTNG*V*FKRDAHGQQMIF | | SEQ ID NO:113 |
| TALL 04.13 | AAGTLVVVVLMPPEQLRNSSFHFLRELSRVLHTNVVFKSDAHGQQMIF | | SEQ ID NO:114 |
| TALL 04.14 | AAGTLVVVVLMPPEQLRNSSFHFLRELSRVLHTNVVFKRDAHGQQMNF | | SEQ ID NO:115 |
| TALL 04.15 | AAGTLVVVVLMPPEQLRNSSFHFLRELSRVLHTNVVFKRDAHGQQM*T*F | | SEQ ID NO:116 |

FIG.3B-2

| | | |
|---|---|---|
| TALL 04.16 | AAGTLVVVVLMPPEQLRNSSFRSLRELSRVLHTNVVFKRDAHGQQMIF | SEQ ID NO:117 |
| TALL 04.17 | AAGTLVVVVLMP-EQLRNSSFHFLRELSRVLHTNVVFKRDAHGQQMIF | SEQ ID NO:118 |
| AML 04.1 | AAGTLVVVVLMPPEQLRNSSFHFLSRELSRVLHTNVVFKRDAHGQQMIF | SEQ ID NO:145 |

FIG.3B-3

```
              1571                                                              1622
NOTCH1    AAGTLVVVVLMPPE.QLRNSSFHF.LRE...LSRVLHTNVVFK....RDAHGQQMIFPYY.G        SEQ ID NO:77
TALL 09   AAGTLVVVVLMPPE.QLRNSSFHF.LRE...LSRVLHTNVVFK....RDAHGQQMIFPPGGG        SEQ ID NO:23
TALL 19   AAGTLVVVLMPPAQQLRNSSFHF.LRE...LSRVLHTNVVFK....RDAHGQQMIFPYY.G         SEQ ID NO:24
TALL 24   AAGTLVVVVLMPPE.QLRNSSFHF.LRE...LSRVLHTNVVLGR...RDAHGQQMIFPYY.G        SEQ ID NO:25
TALL 46   AAGTLVVVVLMPPE.QLRNSSFHLARE...LSRVLHTNVVFK....RDAHGQQMIFPYY.G         SEQ ID NO:26
TALL 53   AAGTLVVVVLMPPE.QLRNSSFHF.LREKEDLSRVLHTNVVFK....RDAHGQQMIFPYY.G        SEQ ID NO:27
TALL 86   AAGTLVVVVLMPPE.QLRNSSFHF.LRE...LSRVLHTNVVFKSMPPRDAHGQQMIFPYY.G        SEQ ID NO:28
TALL 95   AAGTLVVVVLMPPE.QLRNSSFHTALRE...LSRVLHTNVVFK....RDAHGQQMIFPYY.G        SEQ ID NO:29

1571                                                              1622
NOTCH1    AAGTLVVVVLMPPEEQLRNSSFHF  LRELSRVLHTNV      VF         KRDAHGQQMIF PYYG    SEQ ID NO:77
TALL 04.18 AAGTLVVVVLMPPEEQLRNSSFHFA LRELSRVLHTNV      VF         KRDAHGQQMIF PYYG    SEQ ID NO:119
TALL 04.19 AAGTLVVVVLMPPEEQLRNSSFHLY LRELSRVLHTNV      VF         KRDAHGQQMIF PYYG    SEQ ID NO:120
TALL 04.20 AAGTLVVVVLMPPEEQLRNSSFHSHLKRELSRVLHTNV      VF         KRDAHGQQMIF PYYG    SEQ ID NO:121
TALL 04.21 AAGTLVVVVLMPPEEQLRNSSFHF  LRELSRVLHTNVLPPPAF           KRDAHGQQMIF PYYG    SEQ ID NO:122
TALL 04.22 AAGTLVVVVLMPPEEQLRNSSFHF  LRELSRVLHTNVLGR   F          KRDAHGQQMIF PYYG    SEQ ID NO:123
TALL 04.23 AAGTLVVVVLMPPEEQLRNSSFHF  LRELSRVLHTNV      VFERARSKRDAHGQQMIF PYYG        SEQ ID NO:124
TALL 04.24 AAGTLVVVVLMPPEEQLRNSSFHF  LRELSRVLHTNV      VFH        KRDAHGQQMIF PYYG    SEQ ID NO:125
TALL 04.25 AAGTLVVVVLMPPEEQLRNSSFHF  LRELSRVLHTNV      VFD        KRDAHGQQMIF PYYG    SEQ ID NO:126
TALL 04.26 AAGTLVVVVLMPPEEQLRNSSFHF  LRELSRVLHTNV      VF         KRDAHGQQMILGPYYG    SEQ ID NO:127
```

FIG.3C

```
        2311
NOTCH1   WLSRLQSGMVPNQYNPLRGSVAPGPLSTQAPSLQHGMWGPLHSSLAASALSQMMSYQGLPSTRLATQPHLVQTQQVQPQNLQMQQQNLQP    SEQ ID NO:60
TALL 05  ........................................................................................*   SEQ ID NO:30
TALL 13  ..........................................................................................   SEQ ID NO:31
TALL 13  ..........................................................................................   SEQ ID NO:32
TALL 44  .................................................*                                          SEQ ID NO:33

NOTCH1   WLSRLQSGMVPNQYNPLRGSVAPGPLSTQAPSLQHGMWGPLHSSLAASALSQMMSYQGLPSTRLATQPHLVQTQQVQPQNLQMQQQNLQP    SEQ ID NO:60
TALL 04.37 .....................................................................................*     SEQ ID NO:138

2401
NOTCH1    ANIQQQSLQPPPPPPQPHLGVSSAASGHLGRSFLSGEPSQADVQPLGPSSLAVHTILPQESPALPTSLPSSLVPPVTAAQFLTPPSQHS    SEQ ID NO:60 (cont)
TALL 35   .........................................................................*                SEQ ID NO:34
ALL-SIL   ..........................................................AHP*                            SEQ ID NO:35
TALL 53   ..............................................GCHPRWSHP*                                  SEQ ID NO:36
TALL 96   ...............................*                                                           SEQ ID NO:37
TALL 40   ........................PCPRRCHPRWSHP*                                                     SEQ ID NO:38
TALL 08   ..................*                                                                         SEQ ID NO:39
TALL 37                    LSRDLCSHWAPAAWRCTLFCPRRAPPCPRRCHPRWSH*                                    SEQ ID NO:40
DND41                       CCSHWAPAAWRCTLFCPRRAPPCPRRCHPRWSHP*                                      SEQ ID NO:41
HPB-ALL                    EGRGRCSHWAPAAWRCTLFCPRRAPPCPRRCHPRWSHP*                                   SEQ ID NO:42
TALL 23                  GGGGMGSHWAPAAWRCTLFCPRRAPPCPRRCHPRWSHP*                                     SEQ ID NO:43
TALL 91                    ERARQTCSHWAPAAWRCTLFCPRRAPPCPRRCHPRWSHP*                                  SEQ ID NO:44
TALL 84                  RVRARQTCSHWAPAAWRCTLFCPRRAPPCPRRCHPRWSHP*                                   SEQ ID NO:45
TALL 07   ......................*                                                                    SEQ ID NO:46
```

FIG.3D-1

```
TALL 01     ..............................APS*                                                              SEQ ID NO:47
TALL 36     ...........AA*                                                                                   SEQ ID NO:48
TALL 32     .............RHHHHSRTLVA*                                                                        SEQ ID NO:49
TALL 68     ...*                                                                                             SEQ ID NO:50
TALL 57     ...*                                                                                             SEQ ID NO:51

2401
            ANIQQQSLQPPPPPPQPHLGVSSAASGHLGRSFLSGEPSQADVQPLGPSSLAVHTILPQESPALPTSLPSSLVPPVTAAQFLTPPSQHS          SEQ ID NO:60
(cont)
TALL 04.38  ..........................................................................LILWSH*               SEQ ID NO:139
TALL 04.39  .........................................VL*                                                    SEQ ID NO:140
TALL 04.40  ........CGLSPRRPHHHHSRTLA*                                                                       SEQ ID NO:141
TALL 04.41  ....*                                                                                            SEQ ID NO:142
TALL 04.42  ....*                                                                                            SEQ ID NO:143

2491                                                           2556
NOTCH1      YSSPVDNTPSHQLQVPEHPFLTPSPESPDQWSSSSPHSWSDWSEGVSSPPTSMQSQIARIPEAFK*                                SEQ ID NO:60 (cont)
TALL 41     ................................DSGPARRRIPTSPTGPRASPALPPACSPRSPAFRRPSSKRRAPRDPGFLSQAFGRLCALCGCQGRPEEPF*   SEQ ID NO:52
TALL 30     ................................SVP*                                                            SEQ ID NO:53
KOPTK1      ................................RVP*                                                            SEQ ID NO:54
TALL 83     ................................RVP*                                                            SEQ ID NO:54
TALL 94     ................................RVP*                                                            SEQ ID NO:54
TALL 80     ................................RVP*                                                            SEQ ID NO:54
TALL 81     ................................RVP*                                                            SEQ ID NO:54
TALL 47     ...........................VP*                                                                   SEQ ID NO:55
```

FIG.3D-2

```
TALL 52      ..............VP*                                                                       SEQ ID NO:55
TALL 41      ..............Y*                                                                        SEQ ID NO:56
TALL 93      ..............*                                                                         SEQ ID NO:57
TALL 63      ...GRQHPQPPATGA*                                                                        SEQ ID NO:58
TALL 92      ..*                                                                                     SEQ ID NO:59
          2491                                                                              2556
          YSSPVDNTPSHQLQVPEHPFLTPSPESPDQMSSSSSPHSNWSDWSEGVSSPPTSMQSQIARIPEAFK                          SEQ ID NO:60(cont)
                                                                         PAFQRLRLVRGRLQPSHQHAVPDRPHSGGLQVNGAPHETPASFPKPSGVCVRS  SEQ ID NO:144
TALL04.43 VDARADQRSLFKTHVFIQNKNEDFNFF*                                                                SEQ ID NO:144 (cont)
```

FIG.3D-3

```
Fish         GSIVYLEIDNRLCSQ--GSDDCFRNADSAAEYLGALSAREMLR-FPYPTKEVTSEKREPS      SEQ ID NO:61
hN3          GSVVMLEIDNRLCLQSAENDHCFPDAQSAADYLGALSAVERLQ-FPYPLRDVRGEPLEAP      SEQ ID NO:62
Mouse        GSIVYLEIDNRQCVQ--SSSQCFQSATDVAAFLGALASLGSLN-IPYKIEAVKSEPVEPP      SEQ ID NO:63
Rat          GSIVYLEIDNRQCVQ--SSSQCFQSATDVAAFLGALASLGSLN-IPYKIEAVKSETVEPP      SEQ ID NO:64
Human        GSIVYLEIDNRQCVQ--ASSQCFQSATDVAAFLGALASLGSLN-IPYKIEAVQSETVEPP      SEQ ID NO:65
Chicken      GSIVYLEIDNRQCIQ--SSSQCFQSATDVAAFLGALASLGNLN-IPYKIEAVKSETAEPA      SEQ ID NO:66
Frog         GSIVYLEIDNRQCYK--SSSQCFNSATDVAAFLGALASLGSLDTLSYKIEAVKSENMETP     SEQ ID NO:67
HN2          GSKVFLEIDNRQCVQ--DSDHCFKNTDAAAALLASHAIQGTLS---YPLVSVVSESLTPE      SEQ ID NO:68
Concsensus   GS-V-LEIDNR-C----CF------A--L-------L----Y---V--E-----           SEQ ID NO:69

1674                                                 1730
Human NOTCH1 GSIVYLEIDNRQCVQASSQCFQSATDVAAFLGALASLGSLNIPYKI-EAVQSETVEPP        SEQ ID NO:65
Mutation 1   GSIVYLEIDNRQCVQASSQCFQSATDVAAFLGALASLGSLNIPYKIFEAVQSETVEPP        SEQ ID NO:70
Mutation 2   GSIVYAEIDNRQCVQASSQCFQSATDVAAFLGALASLGSLNIPYKI-EAVQSETVEPP        SEQ ID NO:71
Mutation 3   GSIDYLEIDNRQCVQASSQCFQSATDVAAFLGALASLGSLNIPYKI-EAVQSETVEPP        SEQ ID NO:72
Mutation 4   GSIVYLEAMNRQCVQASSQCFQSATDVAAFLGALASLGSLNIPYKI-EAVQSETVEPP        SEQ ID NO:73
Mutation 5   GSIVYLEZDNRQCVQASSQCFQSATDVAAFLGALASLGSLNIPYKI-EAVQSETVEPP        SEQ ID NO:74
Mutation 6   GSIVYLEIDNRQCVQASSQCFQSAMDVAAFLGALASLGSLNIPYKI-EAVQSETVEPP        SEQ ID NO:75

Human Notch1 GSIV    YLEIDNRQCVQASSQCFQSATDVAAFLGALASLGSLNIPYKIEAVQSETVEPP         SEQ ID NO:65
TALL 04.27   GSIV    YLEIDNRQCVQASSQCFQSATDVAAFLGALASLGSLNIPYKIEAVQSETVEPP         SEQ ID NO:128
TALL 04.28   GSIV    YLEIDNRQCVQASSQCFQSATDVAAFLGALASLGSLNIPYKIEAVQSETVEPP         SEQ ID NO:129
TALL 04.29   GSIV    YLEIDNRQCVQASSQCFQSATDVAAFLGALASPGSLNIPYKIEAVQSETVEPP         SEQ ID NO:130
TALL 04.30   GSIV    YLEIDNRQCVQASSQCFQLATDVAAFLGALASLGSLNIPYKIEAVQSETVEPP         SEQ ID NO:131
TALL 04.31   GSIVSTLYLEIDNRQCVQASSQCFQSATDVAAFLGALASLGSLNIPYKIEAVQSETVEPP      SEQ ID NO:132
```

FIG. 3G-1

| | | | |
|---|---|---|---|
| TALL 04.32 | GSIV | YLEIDNRQCVQASSQCFQSANDVAAFLGALASLGSLNIPYKIEAVQSETVEPP | SEQ ID NO:133 |
| TALL 04.33 | GSIV | YLENDNRQCVQASSQCFQSATDVAAFLGALASLGSLNIPYKIEAVQSETVEPP | SEQ ID NO:134 |
| TALL 04.34 | GSI*D* | YLEIDNRQCVQASSQCFQSATDVAAFLGALASLGSLNIPYKIEAVQSETVEPP | SEQ ID NO:135 |
| TALL 04.35 | GSIV | YPEIDNRQCVQASSQCFQSATDVAAFLGALASLGSLNIPYKIEAVQSETVEPP | SEQ ID NO:136 |

| | | |
|---|---|---|
| Human | GSIVYLEIDNRQCVQASSQCFQSATDVAAFLGALASLGSLNIPYKIEAVQSETVEPP | SEQ ID NO:65 |
| TALL 04.36 | GSIVYLEIDNRQCVQASSQCFQSATDVAAFLGALASLGSLNIPYKIEiVQSETVEPP | SEQ ID NO:137 |

RLGSLNIPYKIEAV

1/1
ATG CCG CCG CTC CTG CCC CTG CTC CTG CTC CTG CCC CTG CTC CCA CCC CTG GCC CTC GCC CCG CTC GCC CTG GCC CTG CCC CTG GCA CCC CTG CTC CTG CTG CTG CCC CTG CTC CCA CCC CTG GCC CTC GCC CCG CTC GCC CTG GCC CTG CCC CTG
M P P L L P L L C L A L L P A L A A R G P R C S Q P G E T C L N G G K C E A A

121/41
AAT GGC ACG GAG GCC TGC GTC TGT GGA GGG GCC TTC GTG GGC CCG GCT CGC CAG GAC CCC AAC CCG CTC AGC ACC CCC TGC AAG AAC GCC GGG ACA TCC CAC GTG GTG GAC AGA AGA
N G T E A C V C G G A F V G P R C Q D P N P L S T P C K N A G T C H V V D R R

241/81
GGC GTG GCA GAC TAT GCC TGC AGC TGT GCC CTG GGC TTC TCT GGG CCC CTC TGC CTC ACA CCC CTG GAC AAT GCC CTC ACC AAC CCC TGC AGG AAC GGC ACC TGC CTG CTC
G V A D Y A C S C A L G F S G P L C L T P L D N A C L T N P C R N G G T C D L L

361/121
ACG CTG ACG GAG TAC AAG TGC CGC TGC CCA CCC GGC TGG TCA GGG AAA TGC TGC CAG ACC CCG ACC CCC AAC CCC TGC GCC AGC AAC CCC TGC GCC AAC GGT GGC CAG TGC CTC CCC TTC GAG GCC
T L T E Y K C R C P P G W S G K S C Q Q A D P C A S N P C A N G G Q C L P F E A

481/161
TCC TAC ATC TGC CAC TGC CCA ACC TTC CAT GGC CCC ACC TGC CGG CAG GAT GTC AAC GAG TGT GGC ATC CGG CAG GAG CCC TGC TTC CAC GGC CTT GGC CTG CGG CAC GGC GGA GCC ACC TGC CAC AAC GAG GTC GGC
S Y I C H C P P S F H G P T C R Q D V N E C G Q K P G L C R H G G T C H N E V G

601/201
TCC TAC CGC TGC GTC TGC CGC ACT CAC ACT GGC CCC AAC TGC GAG CGG CCC TAC GTG CCC TGC AGC CCG AGC CCC TGC CAG AAC GGG GGC ACC TGC CGC CCC ACA GGC GAC GTC ACC
S Y R C V C R A T H T G P N C E R P Y V P C S P S P C Q N G G T C R P T G D V T

9/31
...CTC AAT GGG GGC AAG TGT GAA GCG GCC
...L N G G K C E A A

211/71
...ACC CCC AGC ACC CCC TGC AAG AAC GCC GGG ACA TCC CAC GTG GTG GAC AGA AGA
...T P C K N A G T C H V V D R R

331/111
...ACC AAC CCC TGC AGG AAC GGC ACC TGC CTG CTC
...T N P C R N G G T C D L L

451/151
...AAC CCC TGC GCC AAC GGT GGC CAG TGC CTC CCC TTC GAG GCC
...N P C A N G G Q C L P F E A

571/191
...CAC AAC GAG GTC GGC
...H N E V G

```
721/241
CAC GAG TGT GCC TGC CTG CCA GGC TTC ACC GGC TGC GAA AAT ATC GAC GAG TGT CCA GGA AAC AAC TGC AAG AAC GGG GGT GCC TGT GTG GAC GGC GTG AAC ACC TAC AAC
 H   E   C   A   C   L   P   G   F   T   G   C   E   N   I   D   E   C   P   G   N   N   C   K   N   G   G   A   C   V   D   G   V   N   T   Y   N

841/281
TGC CGC TGC CCG CCA GAG TGG ACA GGT CAG TAC TGT TGT ACC GAG GAT GTG GAC GAG TGC CTG ATG CCA AAT GCC TGC CAG AAC GGG ACC TGC CAC AAC ACC CAC GGT TAC AAC
 C   R   C   P   P   E   W   T   G   Q   Y   C   T   E   D   V   D   E   C   Q   L   M   P   N   A   C   Q   N   G   T   C   H   N   T   H   G   Y   N

961/321
TGC GTG TGT GTC AAC GGC TGG ACT GGT GAG GAC TGC TCC GAG AAC ATT GAT GAC TGT GCC AGC GCC TGC TTC CAC GGC GCC ACC TGC CAT GAC CGT GTG GCC TCC TTC TAC TGC GAG
 C   V   C   V   N   G   W   T   G   E   D   C   S   E   N   I   D   D   C   A   S   A   A   C   F   H   G   A   T   C   H   D   R   V   A   S   F   Y   C   E

1081/361
TGT CCC CAT GGC AGG ACA GGT CTG CTG TGC CAC CTC AAC GAC GCC ATC AGC AAC CCT TGC AAC GAG GGC TCC AAC TGC GAC ACC AAC CCT GTC AAT GGC AAG GCC ATC TGC ACC TGC
 C   P   H   G   R   T   G   L   L   C   H   L   N   D   A   I   S   N   P   C   N   E   G   S   N   C   D   T   N   P   V   N   G   K   A   I   C   T   C

1201/401
CCC TGG GGG TAC ACG GGC CCC CGA TCC GAG TGT GAT GAC GAG TGC TCG GGT GCC AAC CCC TGC GAG CAT GCG GGC AAG TGC ATC AAC ACG CTG GGC TCC TTC GAG TGC CAG TGT
 P   S   G   Y   T   G   P   A   C   S   Q   D   V   D   E   C   S   L   G   A   N   P   C   E   H   A   G   K   C   I   N   T   L   G   S   F   E   C   Q   C

1321/441
CTG CAG GGC TAC ACG GGC CCC CGA TGC GAG ATC GAC GTC AAC GAG TGC GTC TCG AAC CCG TGC CAG AAC GAC GCC ACC TGC CTG GAC CAG ATT GGG GAG TTC CAG TGC ATC TGC ATG CCC
 L   Q   G   Y   T   G   P   R   C   E   I   D   V   N   E   C   V   S   N   P   C   Q   N   D   A   T   C   L   D   Q   I   G   E   F   Q   C   I   C   M   P
```

FIG. 5B

```
1441/481                                                                                              1501/501
GGC TAC GAG GGT GTG CAC TGC GAG GTC AAC ACA GAC GAG TGT GCC AGC AGC CCC TGC CTG CAC AAT GGC CGC TGC CTG GAC AAG ATC AAT GAG TTC CAG TGT GAG TGC CCC ACG GGC TTC
 G   Y   E   G   V   H   C   E   V   N   T   D   E   C   A   S   S   P   C   L   H   N   G   R   C   L   D   K   I   N   E   F   Q   C   E   C   P   T   G   F

1531/511                                                                                              1591/531                                          1621/541
ACT GGG CAT CTG TGC CAG TAC GAT GTG GAC GAG TGT GCC AGC ACC CCC TGC AAG AAT GGT GCC AAG TGC CTG GAC GGA AAC GCC AAG TGT GTG TGC ACG GAG TAC ATG GGG
 T   G   H   L   C   Q   Y   D   V   D   E   C   A   S   T   P   C   K   N   G   A   K   C   L   D   G   N   A   K   C   V   C   T   E   G   Y   T   G

1681/561                                                                                              1741/581                                          1771/591
ATG CAC TGC GAG GTG GAC ATC GAT GAG TGC GAC CCC GAC CCC TGC CAC TAC GGC TCC TGC AAG GAC GGC GTC GCC ACC TTC ACC TGC CTC TGC CGA CCC GGC TAC ACG GGC CAC CAC TGC
 M   H   C   E   V   D   I   D   E   C   D   P   D   P   C   H   Y   G   S   C   K   D   G   V   A   T   F   T   C   L   C   R   P   G   Y   T   G   H   H   C

1831/611                                                                                              1861/621                                          1891/631
GAG ACC AAC ATC AAC GAG TGC TCC AGC CAG CCC TGC CGC CAC GGT GGG ACC TGC CAG GAC CGC GAC AAC GCC TAC CTC TGC TTC TGC CTG AAG GGG ACC ACA GGA CCC AAC TGC GAG ATC
 E   T   N   I   N   E   C   S   S   Q   P   C   R   H   G   G   T   C   Q   D   R   D   N   A   Y   L   C   F   C   L   K   G   T   T   G   P   N   C   E   I

1921/641                                                                                              1981/661                                          2011/671
AAC CTG GAT GAC TGT GCC AGC AGC CCC TGC GAC AGC GGG ACC TGC CTG GAC ACC TGT CTG GAC AAG ATC GAT GGC TAC GAG TGT GCC TGT GAG CCG GGC TAC ACA GGG GCC ATG TGT AAC ATC AAC ATC GAT
 N   L   D   D   C   A   S   S   P   C   D   S   G   T   C   L   D   T   C   L   D   K   I   D   G   Y   E   C   A   C   E   P   G   Y   T   G   S   M   C   N   I   N   I   D

2041/681                                                                                              2101/701                                          2131/711
GAG TGT GCG GGC AAC CCC TGC CAC AAC GGT GGC ACC TGC GAG GAC GGC ATC AAT GGC TTC ACC TGC CGC TGC CCC GAG GGC TAC CAC GAC CCC ACC TGC CTG AGT GAG GTC AAT GAG TGC
 E   C   A   G   N   P   C   H   N   G   G   T   C   E   D   G   I   N   G   F   T   C   R   C   P   E   G   Y   H   D   P   T   C   L   S   E   V   N   E   C
```

FIG. 5C

2161/721
AGC AGC AAC CCC TGC GTC CAC GGG GCC TGC CGG GAC TCC CTC AAC GGG TAC AAG TGC GAC TGT GAC CCT GGC TGG AGT GGG ACC AAC TGT AAC TGT GAA TCC AAC
 N   S   N   P   C   V   H   G   A   C   R   D   S   L   N   G   Y   K   C   D   C   D   P   G   W   S   G   T   N   C   N   C   E   S   N

2221/741
2281/761
CCT TGT GTC AAC GGC GGC ACC ATG AGT ACC GCC ATC AAC TCC CGG GAG GGC TTC AGC GGG GCC CCC AAC TGC CAG ACC AAC ATC AAC GAG TGT GCG TCC ACC CCA TGT
 P   C   V   N   G   G   T   M   S   T   A   I   N   S   R   E   G   F   S   G   A   P   N   C   Q   T   N   I   N   E   C   A   P   P   C

2341/781
2401/801
CTG AAC CAG GGC ACG TGT ATT GAC GAC GTT GCC GGG TAC AAG TGC AAC TGC CTG CCC TAC ACA GGT GCC ACG TGT GAG GTG GTG CTG GCC CCC GCC CCC TCC AGA AAC
 L   N   Q   G   T   C   I   D   D   V   A   G   Y   K   C   N   C   L   L   P   Y   T   G   A   T   C   E   V   V   L   A   P   C   R   N

2461/821
2521/841
GGC GGG GAG TCC AGG CAA TCC GAG GAC TAT GAG GAC TTC TCC GTC TGT CCC ACG GGC TGG AAC CAA GGG CAG ACC TGT GAG GTC GAC ATC AAC GAG TGT GTT CTG AGC CCG TGC CGG
 G   G   E   C   R   Q   S   E   D   Y   E   D   F   S   V   C   P   T   G   W   N   Q   G   Q   T   C   E   V   D   I   N   E   C   V   L   S   P   C   R

2581/861
2641/881
CAC GGC GGA TCC CAG AAC ACC CAC GGC GGC TAC CGG TGC CAC TGC CAG GCC AAC TAC AGT GGG CGC AAC TGC GAG ACC GAC ATC GAC GAC TGT CGA CCC AAC CCG
 H   G   A   S   C   Q   N   T   H   G   G   Y   R   C   H   C   Q   A   G   Y   S   G   R   N   C   E   T   D   I   D   D   C   R   P   N   P

2701/901
2761/921
TGC CAC AAT GGG GGC TCC TGC ACA GAC GGC ATC AAC ACG GCG TTC TGC GAC TGC CTG CCC GGC TTC CGC GGG ACT TTC TGT GAG GAG GAC ATC AAC GAG TGT GCC TCC GAC CCC CGG AAC GGG GCC AAC
 C   H   N   G   G   S   C   T   D   G   I   N   T   A   F   C   D   C   L   P   G   F   R   G   T   F   C   E   E   D   I   N   E   C   A   S   D   P   C   R   N   G   A   N

281/961                    291/971                    291/981                    291/991
TCC ACG GAC TCC GTG GAC TAC ACC AGT ACC TGC CCA GCC TTC AGC GGC ATC CAC TGT GAG AAC AAC ACG CCT GAC TCC ACG AGC ACC TCC TTC AAC GGT GCC ACC TCC GTG
 C  T  D  C  V  D  S  Y  T  C  T  C  P  A  G  F  S  G  I  H  C  E  N  N  T  P  D  C  T  E  S  S  C  F  N  G  G  T  C  V

301/1001                   301/1011                   301/1021                   301/1031
GAC GGC ATC AAC TCG TTC ACC TGC CTG CCA CCC GGC TTC ACG GGC TCG TAC TGC CAG CCC CAT GAC GTC AAT GAG TGC GAC TCA CAG CCC TGC CTG CAT GGG GGC ACC TGT CAG GAC GGG
 D  G  I  N  S  F  T  C  L  P  P  G  F  T  G  S  Y  C  Q  P  H  D  V  N  E  C  D  S  Q  P  C  L  H  G  G  T  C  Q  D  G

312/1041                   315/1051                   318/1061                   321/1071
TCC GGC TCC TAC AGG TGC ACC TGC CCC CAG GGC TAC ACT GGC TCC TAC TGC CAG AAC TGC CAG AAC CTT GTG CAC TGG TGT GAC TCC TCG CCC TGC AAG AAC GGA GGC AAA TGC TGG CAG ACC CAC ACC
 C  G  S  Y  R  C  T  C  P  Q  G  Y  T  G  S  Y  C  Q  N  C  Q  N  L  V  H  W  C  D  S  S  P  C  K  N  G  G  K  C  W  Q  T  H  T

324/1081                   327/1091                   330/1101                   333/1111
CAG TAC CGC TGC GAG TGC CCC AGC GGC TGG ACC GGC CTT TAC TGC GAC GTG CCC AGC GTG TCC TGT GAG GTG GCT GCG GCA CAA GTG CGT GTT GGC CGT GAC GTG GCC CGC CTG CAG CAT GGA
 Q  Y  R  C  E  C  P  S  G  W  T  G  L  Y  C  D  V  P  S  V  S  C  E  V  A  A  Q  R  Q  G  V  D  V  A  R  L  C  Q  H  G

336/1121                   339/1131                   342/1141                   345/1151
GGG CTC TGT GTG GAC GCG GGC AAC ACG CAC CAC TGC CGC TGC CAG GCG GGC TAC ACA GGC AGC TAC TGT GAG GAC CTG GTG GAC GAG TGC TCA CCC AGC CCC TGC CAG AAC GGG GCC ACC
 G  L  C  V  D  A  G  N  T  H  H  C  R  C  Q  A  G  Y  T  G  S  Y  C  E  D  L  V  D  E  C  S  P  S  P  C  Q  N  G  A  T

348/1161                   351/1171                   354/1181                   357/1191
TGC CTG GAC TAC CTG GGC GGC TAC TCC TGC AAG TGC GTG GCC GGC TAC CAC GGC GTG AAC TGC TCT GAG GAG ATC GAC GAG TGC CTC TCC CAC CCC TGC CAG AAC GGG GGC ACC TGC CTC
 C  L  D  Y  L  G  G  Y  S  C  K  C  V  A  G  Y  H  G  V  N  C  S  E  E  I  D  E  C  L  S  H  P  C  Q  N  G  G  T  C  L

FIG. 5E

```
3601/1201                    3631/1221                         3661/1231
GAC CTC CCC AAC ACC TAC AAG TCC TGC TCC CCA CGG GGC ACT CAG GGT GTG CAC TGT GAG ATC AAC GTG GAC GAC TGT AAT CCC CCG GTT GAC CCC AAG TCC TTT
 D   L   P   N   T   Y   K   C   S   C   P   R   G   T   Q   G   V   H   C   E   I   N   V   D   D   C   N   P   P   V   D   P   V   S   R   S   P   K   C   F

3721/1241                                 3751/1251                                3781/1271
AAC AAC GGC ACC TGC GTG GAC CAG GTG GGC GGC TAC AGC TGC ACC TGC CCG CCC GGC TTC GTG GGG GAG CGG TGT GAG GGG GAT GTC AAC GAG TGC CTG TCC AAC CCC TGC GAC GCC CGT
 N   N   G   T   C   V   D   Q   V   G   G   Y   S   C   T   C   P   P   G   F   V   G   E   R   C   E   G   D   V   N   E   C   L   S   N   P   C   D   A   R

3841/1281                                       3901/1301                          3931/1311
GGC ACC CAG AAC TGC GTG CAG CGG GTC AAT GAC TTC CAC TGC GAG TGC CGT GCT GGT CAC ACC GGG CGG CGC TGT GAG TCC GTC ATC AAT GGC TGC AAA CCC TGC AAG AAT GGG
 G   T   Q   N   C   V   Q   R   V   N   D   F   H   C   E   C   R   A   G   H   T   G   R   R   C   E   S   V   I   N   G   C   K   P   C   K   N   G

3961/1321                                   3991/1331                              4051/1351
GGC ACC TGC GTG GTG TCC GCC GTG GCC AGC AAC ACC GCC CGG GGC TTC ATC TGC AAG TGC CCT GCC GGG TTC GAG GGG GCC ACC TGT GAG GAA GAT GCC CGG ACC TGC GGG AGC CTG CGC CTC AAC
 G   T   C   V   V   S   A   V   A   S   N   T   A   R   G   F   I   C   K   C   P   A   G   F   E   G   A   T   C   E   N   D   A   R   T   C   G   S   L   R   C   L   N

4081/1361                                   4111/1371                              4171/1391
GGG GGC ACA TCC ATC TCC GGC CCC AGG TCC CCC ACC TGC CTG TGC CTG GGC CCC TTC ACG GGC CCC GAA TCC CAG TTC CCG GCC AGC TCC CCC TGC CTG GGG AAC CCC TGC TAC AAC
 G   G   T   C   I   S   G   P   R   S   P   T   C   L   C   L   G   P   F   T   G   P   E   C   Q   F   P   A   S   S   P   C   L   G   G   N   P   C   Y   N

4231/1401                    4261/1421                                              4291/1431
CAG GGG ACC TGT GAG CCC ACA TCC GAG AGC CCC TTC TAC CGT TGC CTC TGC CCC GCC AAA TTC AAC GGG CTC CTG TGC CAC ATC CTG GAC TAC AGC TTC GGT GGG GGC GCC GGG CGC GAC
 Q   G   T   C   E   P   T   S   E   S   P   F   Y   R   C   L   C   P   A   K   F   N   G   L   L   C   H   I   L   D   Y   S   F   G   G   G   A   G   R   D
```

FIG. 5F

4321/1441
ATC CCC CCG CTG ATC ATC GAG GAG GCG TCC CAG GAG GAC CTG CCC GAG TCC TGC CAG GAG GAC GCG GGT AAC AAG GTC TGC AGC CTG CAG TGC AAC AAC CAC GCC TGG TGC CCC TCC GGC CTC GGC CTC GGC GAC GGT GGC TCC
I  P  P  L  I  I  E  E  A  C  E  L  P  E  C  Q  E  D  A  G  N  K  V  C  S  L  Q  C  N  N  H  A  C  G  W  D  G  G  D  C

4411/1471

4381/1461
4441/1481
TCC CTC AAC TTC AAT GAC CCC TGG AAG AAC TGC ACG CAG TCT CTG CAG TGC TGG AAG TAC TTC AGT GAT GGC CAT TGT GAC AGC CAG CAC TGC CTC TTC GAC GGC TTT
S  L  N  F  N  D  P  W  K  N  C  T  Q  S  L  Q  C  W  K  Y  F  S  D  G  H  C  D  S  Q  C  N  S  A  G  C  L  F  D  G  F

4531/1511
4501/1501
4561/1521
GAC TGT CAG CGT GCG GAA GGC TGC AAC CCC CTG TAC GAC CAG TAC TGC AAG GAC CAC TTC AGC GAC GGC CAC TGC GAC CAG GGC TGC AAC AGC GCG GAG TGC GAG TGG GAC GGG CTG
D  C  Q  R  A  E  G  C  N  P  L  Y  D  Q  Y  C  K  D  H  F  S  D  G  H  C  D  Q  G  C  N  S  A  E  C  E  W  D  G  L

4651/1551
4621/1541
4681/1561
GAC TGT CGT GAG CAT GTA CCC GAG AGG CTG GCC GCC GGC ACG CTG GTG GTG GTG GTG CTG ATG CCG CAG CAG CAG CTG CGC AAC AGC TCC TTC CAC TTC CTG CGG GAG CTC AGC CGC GTG
D  C  A  E  H  V  P  E  R  L  A  A  G  T  L  V  V  V  V  L  M  P  P  E  Q  L  R  N  S  S  F  H  F  L  R  E  L  S  R  V

4771/1591
4741/1581
4801/1601
CTG CAC ACC AAC GTG GTC TTC AAG CGT GAC GCA CAC GGT CAG CAG ATG ATC TTC CCC TAC TAC GGC CGC GAG GAG GAG CTG CGC AAG CAC CCC ATC AAG CGT GCC GCC GAG GGC TGG GCC
L  H  T  N  V  V  F  K  R  D  A  H  G  Q  Q  M  I  F  P  Y  Y  G  R  E  E  E  L  R  K  H  P  I  K  R  A  A  E  G  W  A

4861/1621
4981/1661
4921/1641
GCA CCT GAC CCC GCC CTG CTG CTG GGC CAG GTG AAG GCC TCG CTG CTC CCT GGT GGC AGC GAG GGT CGG CGG CGG CGG AGG AGG CTG GAC CCC ATG GAC GTC CGC GGC TCC ATC GTC TAC CTG GAG
A  P  D  A  L  L  L  G  Q  V  K  A  S  L  L  P  G  G  S  E  G  G  R  R  R  R  R  E  L  D  P  M  D  V  R  G  S  I  V  Y  L  E

5041/1691
ATT GAC AAC CGG TGT GTG CAG GCC TCC TCG CAG TTC CAG TCC AGT ACC GAC GTG GCC GCC TTC CTG GGA GCG CTC GCC AGC CTC GGC AGC CTC AAC ATC CCC TAC AAG ATC GAG
 I   D   N   R   Q   C   V   Q   A   S   S   Q   C   F   Q   S   A   T   D   V   A   A   F   L   G   A   L   A   S   L   G   S   L   N   I   P   Y   K   I   E

5161/1721                                                                                                   5221/1741
GCC GTG CAG AGT GAG ACC GTG GAG CCG CCC CCG CCC GCC CAG CTG CAC TTC ATG TAC GTG GCG GCG GCC TTT GTG CTG CTG TTC TTC GTG GGC GTG CTG CTC TCC CGC AAG
 A   V   Q   S   E   T   V   E   P   P   P   P   A   Q   L   H   F   M   Y   V   A   A   A   F   V   L   L   F   F   V   G   C   G   V   L   L   S   R   K

5281/1761                                                        5371/1791
CGC CGG CGG CAT GGC CAG CTC TGG TTC CCT GAG GGC TTC AAA GTG TCT GAG GCC AGC AAG AAG AAG CGG AGG CGC GAG CCC CTC GGC GAG GAC TCC GTG GGC CTC AAG CCG CTG AAC
 R   R   R   Q   H   G   Q   L   W   F   P   E   G   F   K   V   S   E   A   S   K   K   K   R   R   E   P   L   G   E   D   S   V   G   L   K   P   L   K   N

5401/1801                                                                                                   5461/1821
CCT TCA GAC GGT GCC CTC ATG GAC GAC AAC CAG AAT GAG TGG GGG GAC GAG GAC CTG GAG ACC AAG AAG TTC CGG TTC GAG GAG CCC GTG GTT CTG CCT GAC GAC CTG GAC GAC CAG ACA GAC
 A   S   D   G   A   L   M   D   D   N   Q   N   E   W   G   D   E   D   L   E   T   K   K   F   R   F   E   E   P   V   V   L   P   D   D   L   D   D   Q   T   D

5521/1841                                                                                                   5581/1861
CAC CGG CAG TGG ACT CAG CAG CAC CTG GAT GCC GCC GCT GAC CTG CGC ATG TCT GCC ATG GCC CCC ACA CCG CCC CAG GGT GAG GTT GAC GCC GAC TGC ATG GAC GTC AAT GTC CGG GGT CCT
 H   R   Q   W   T   Q   Q   H   L   D   A   A   A   D   L   R   M   S   A   M   A   P   T   P   P   Q   G   E   V   D   A   D   C   M   D   V   N   V   R   G   P

5641/1881                                                                                                   5731/1911
GAT GGC TTC ACC CCG CTC ATG ATC GCC TCC TGC AGC GGG GGG CTG GAG ACG GGC AAC AGC GAA GAG GAG GAC GCG CCG GCC GTC ATC TCC GAC TTC ATC TAC CAG GGC GCC AGC
 D   G   F   T   P   L   M   I   A   S   C   S   G   G   G   L   E   T   G   N   S   E   E   E   E   D   A   P   A   V   I   S   D   F   I   Y   Q   G   A   S

FIG. 5H

5761/1921                  5791/1931                               5821/1941                                                5851/1951
CTG CAC AAC CAG ACA GAC CGC ACG GAG GAG ACC CCC TTG CAC CTG CTG GCC GCC CGC TAC TCA CCC GAT CCC GCC AAG CCC CTG GAG GCC ACC CTC GAG CTA GAT GCC AAC ATC CAG GAC AAC
L   H   N   Q   T   D   R   T   G   E   T   A   L   H   L   L   A   A   R   Y   S   R   S   D   A   A   K   R   L   L   E   A   S   A   D   A   N   I   Q   D   N

5881/1961                  5911/1971                               5941/1981                                                5971/1991
ATG GGC CGC ACC CCG CTG CAT GCG GCC CCT GTG TCT GCC GAC GCA CAA GGT GTC TTC CAG ATC CTG ATC CGA AAC CGA GCC ACA GAC CTG GAT GCC GCC AGG ATG CAT GAT GGT ACG ACG CCA CTG
M   G   R   T   P   L   H   A   A   V   S   A   D   A   Q   G   V   F   Q   I   L   I   R   N   R   A   T   D   L   D   A   R   M   H   D   G   T   T   P   L

6001/2001                  6031/2011                               6061/2021                                                6091/2031
ATC CTG GCC CCT GCC CTG GTG GAC GAG GGC ATG CTG GAG GAC CTC ATC AAC TCA CAC GCC GAC GTC AAC GCC GTA GAT GAC CTG GGC AAG TCC GCC CTG CAC TGG TCC GCC CTG CAC GTG AAC
I   L   A   A   R   L   A   V   E   G   M   L   E   D   L   I   N   S   H   A   D   V   N   A   V   D   D   L   G   K   S   A   L   H   W   A   A   A   V   N

6121/2041                  6151/2051                               6181/2061                                                6211/2071
AAT GTG GAT GCC GCA GTT GTG CTC CTG AAG AAC GGT GCT AAC AAA GAT ATG CAG AAC AAC AGG GAG GAG ACA CCC CTG TTT CTG GCC GCC CGG GAG GGC AGC TAC GAG ACC GAG GCC AAG GTG
N   V   D   A   A   V   V   L   L   K   N   G   A   N   K   D   M   Q   N   N   R   E   E   T   P   L   F   L   A   A   R   E   G   S   Y   E   T   A   K   V

6241/2081                  6271/2091                               6301/2101                                                6331/2111
CTG CTG GAC CAC TTT GCC AAC CGG GAC ATC ACG GAT CAT ATG GAC CGG CTG CCG GAC ATC GCA CAG GAG CGG ATG CAT CAC GAC ATC GTG AGG CTG CTG GAC GAG TAC AAC CTG GTG
L   L   D   H   F   A   N   R   D   I   T   D   H   M   D   R   L   P   R   D   I   A   Q   E   R   M   H   H   D   I   V   R   L   L   D   E   Y   N   L   V

6361/2121                  6391/2131                               6421/2141                                                6451/2151
CGC AGC CCG CAG CTG CAC GGA GCC CCC CTG GGG GGC ACC CCC ACG CTG TCG CCC CCC CTC TGC TCC CCC AAC GGC TAC CTG GGC AGC CTC AAG CCC GGC GTG CAG GGG AAG AAG GTC CGC
R   S   P   Q   L   H   G   A   P   L   G   G   T   P   T   L   S   P   P   L   C   S   P   N   G   Y   L   G   S   L   K   P   G   V   Q   G   K   K   V   R

FIG. 5I

```
6481/2161                         6511/2171                              6541/2181                              6571/2191
AAG CCC AGC AGC AAA GGC CTG TGT GGA ACC AAG GAG CTC AAG GAC CTC AAG GCC CCG AGG AAG AAG TCC CAG GAC AAG GGC AAC TCC CGC ATG CTC TCG CCC
 K   P   S   S   K   G   L   A   C   G   S   K   E   A   K   D   L   K   A   R   R   K   K   S   Q   D   K   G   L   L   D   S   S   G   M   L   S   P

6601/2201                         6631/2211                              6661/2221                              6691/2231
GTG GAC TCC CTG GAG TCA CCC CAT GGC TAC CTG TCA GAG GTG GCC TCC CCG CTG CTG CCA CTG CTG CCG TCT CCG TTC CAG CAG TCC CCG GTC AAC CAC CTC CCG GGA ATG CCG GAC
 V   D   S   L   E   S   P   H   G   Y   L   S   D   V   A   S   P   P   L   L   P   L   L   P   S   P   F   Q   Q   S   P   V   N   H   L   P   G   M   P   D

6721/2241                         6751/2251                              6781/2261                              6811/2271
ACC CAC CTG GGC ATC GGG CAC CTG AAC GTC GCG GCG AAG CCG GAG ATG GCG GCG GCG CTG GGT GGC GGC GGC CGG CTG GCC TTT GAG ACT GGA CCT GGT CCC CGC CTG CCT GTG GCC
 T   H   L   G   I   G   H   L   N   V   A   A   K   P   E   M   A   A   A   L   G   G   G   G   R   L   A   F   E   T   G   P   P   R   L   S   H   L   P   V   A

6841/2281                         6871/2291                              6901/2301                              6931/2311
TCT GCC ACC ACC GTC CTG GGG AGT TCC TCC GGC GCC GGA GCG GCC CTG AAT TTC ACT GTG GGG GGC TCC ACC AGT TTG AAT GGT CAA TGC GAG TGG CTG TCC CGG CAG AGC GGC ATG GTG
 S   A   T   T   V   L   G   S   S   S   G   A   G   A   A   L   N   F   T   V   G   G   S   T   S   L   N   G   Q   C   E   W   L   S   R   L   Q   S   G   M   V

6961/2321                         6991/2331                              7021/2341                              7051/2351
CCG AAC CAA TAC AAC CCT CTG CGG GGA AGT GTG GCA CCA GGC CCC CTG AGC ACA CAG GCC CCC TCC CTG CAG CAT GGA ATG GTA GGC CCG CTG CAC AGT TCC TTG GCC GCC AGT GCC CTG
 P   N   Q   Y   N   P   L   R   G   S   V   A   P   G   P   L   S   T   Q   A   P   S   L   Q   H   G   M   V   G   P   L   H   S   S   L   A   A   S   A   L

7081/2361                         7111/2371                              7141/2381
TCC CAG ATG ATG AGC TAC CAG GGC CTG CCC AGC ACC CGG CTG GCC ACC CAG CCT CAC CTG GTG CAG ACC CAG CAG GTG CAG CCA CAA AAC TTA CAG ATG CAG CAG AAC CTG CAG CCA
 S   Q   M   M   S   Y   Q   G   L   P   S   T   R   L   A   T   Q   P   H   L   V   Q   T   Q   Q   V   Q   P   Q   N   L   Q   M   Q   Q   N   L   Q   P
```

FIG. 5J

7201/2401        7251/2421                    7291/2431
ACA AAC ATC CAG CAG CAA ACC CTG CAG CCG CCA CCA CCA CCG CAC CTT GCC GTG TCA GCA GCC ACC GCC CTG GCC CCG AGC TTC CTG AGT GGA GAG CCG AGC
 A   N   I   Q   Q   Q   T   L   Q   P   P   P   P   Q   H   L   G   V   S   S   A   A   S   G   H   L   G   R   S   F   L   S   G   E   P   S

7321/2441                           7351/2451                           7381/2461                           7411/2471
CAG GCA GAC GTG CAG CCC CTG GGA CCA TCA CTG GCC GTG CAC ACT ATT CTG CCC CAG GAG TCC CCT GCC CTG CCA TCG TCG CTG CCA TCC GTC CCA CCA GTG ACC GCA GCC
 Q   A   D   V   Q   P   L   G   P   S   S   L   A   V   H   T   I   L   P   Q   E   S   P   A   L   P   T   S   S   L   P   P   S   V   P   P   V   T   A   A

7441/2481                           7471/2491                           7501/2501                           7531/2511
CAG TTC CTG AAG CCC CCC TCG CAG CAC AGC TAC TCC TGG CCT GTG GAC AAC ACC CCC AGC CAC CAG CTA CAG GTG CCC GAG CAC CCC TTC CTC ACC CCG TCC CCT GAG TCC CCT GAC CAG
 Q   F   L   T   P   P   S   Q   H   S   Y   S   S   P   V   D   N   T   P   S   H   Q   L   Q   V   P   E   H   P   F   L   T   P   S   P   E   S   P   D   Q

7561/2521                           7621/2541                           7651/2551
TGG TCC AGC TCG TCC CCG CAT TCC AAC GTC TCC GAC TGG TCC GAG GGT GTC TCC AGC CCT CCG ACC AGC ATG CAG TCC CAG ATC GCC AGG ATT CCG GAG GCC TTC AAG TAA
 W   S   S   S   S   P   H   S   N   V   S   D   W   S   E   G   V   S   S   P   P   T   S   M   Q   S   Q   I   A   R   I   P   E   A   F   K   *

FIG. 5K

NOTCH1 exon 27 seq
5030 T/A
5032 INS<AGCACACTT>
5036 T/C
5042 T/A
5042 T/C
5093 C/A
5156 T/C
5157 INS<TCC>
5104 G/C
5129 T/C NOTCH1 exon 27 mut
1677 V/D
1678 INS STL
1679 L/P
1681 I/N
1681 I/T
1698 T/N
1719 I/T
7120 INS P
1702 A/P
1710 L/P 5165 INS<CCCGGTTGGGCAGCCTCAACATCCCTACAAGATCGAGGCCG> (SEQ ID NO:146) 1722 V/A. 1723 INS RLGSLNIPYKIEAV(SEQ ID NO:137)

Exon 26 seq
4802 T/C
4781 T/C
4796 G/C
4724 T/C
4735 DEL(GTG)
4778 T/C
4757 T/C
4825 C/A
4815 DEL(GGT)

4825 DEL (CGTGACGCA) INS<ACG>
4857 DEL (TACTAC) INS<CCTGGGGGA>

Exon 26 Mutation
1601 L/P
1594 L/P
1599 R/P
1575 L/P
1579 DEL V
1593 F/S
1586 L/P
1609 R/S
1606 DEL V

1609 R/T. 1610 DEL D. 1611 DEL A
1620 Y/P. 1621 Y/G. 1622 INS G

FIG. 6A

4751 INS<CCC>
4821 DEL(CAAGC) INS<GG>
4779 INS<AGC>
4779 INS<TAAGGAGGA>
4777 DEL(TTCC) INS<ACTGCG>
4781 T/C, 4829 A/T
4821 INS<ATCAATGCCCCC> (SEQ ID NO:147)

1584 E/A, 1585 INS Q
1607 F/L, 1608 K/G, 1609 INS R
1593 F/L, 1594 INS A
1594 INS K, 1595 INS E, 1596 INS D
1593 F/T, 1594 INS A
1594 L/P, 1610 D/V
1608 INS S, 1609 INS M, 1610 INS P, 1611 INS P

Exon 34 Seq
7195 C/T
7183 C/T
7180 C/T
7025 INS<GAGCACAGGCCCCCT> (SEQ IS NO:148)
7428 DEL(C)
7422 INS<GG>
7405 INS<GG>
7403 C/A
7389 DEL (C)
7378 C/T
7330 INS<TTAAGTAGAGACTT> (SEQ ID NO:149)
7330 DEL (G) INS<TGT>
7329 DEL (C) INS<GGGCCGTGGACG> (SEQ ID NO:150)
7331 DEL(T) INS<GTGGAGGGGGGATGG> (SEQ ID NO:151)
7317 INS<AGAAC>,7518 T/G
7316 INS<GGGTT>
7321 C/T Exon 34 Mutation
2399 STOP
2395 STOP
2394 STOP
2342 STOP
2477 *STOP
2474 AHP*STOP
2469 GCHPRWSHP*STOP (SEQ ID NO:154)
2468 *STOP
2464 PCPRRCHPRWSHP*STOP (SEQ ID NO:155)
2460 *STOP
2444 LSRDLCSHWAPAAWRCTLFCPRRAPPCPRRCHPRWSH*STOP (SEQ ID NO:156)
2442 CCSHWAPAAWRCTLFCPRRAPPCPRRCHPRWSHP*STOP (SEQ ID NO:157)
2442 EGRGRCSHWAPAAWRCTLFCPRRAPPCPRRCHPRWSHP*STOP (SEQ ID NO:158)
2444 GGGGMGSHWAPAAWRCTLFCPRRAPPCPRRCHPRMSHP*STOP (SEQ ID NO:159)
2440 ERARQTCSHWAPAAWRCTLFCPRRAPPCPRRCHPRWSHP*STOP (SEQ ID NO:160)
2439 RVRARQTCSHWAPAAWRCTLFCPRRAPPCPRRCHPRWSHP*STOP (SEQ ID NO:161)
2441 *STOP

FIG. 6B

7299 INS <TGCCC>
7262 INS <CC>
7233 INS<CC>
7216C/T
7210 C/T

7548 DEL(GTCCCCTGAC), 7561 T/C (SEQ ID NO:152)
7542 INS<GAGGGTC>
7544 DEL(CT)
7539 INS <C>
7522 C/T, 7529 DEL(TCCTCACCCC) (SEQ ID NO:153)
INS<GA>,
7519 G/T
7480 DEL (CCTGTG) INS<GGGC>
7478 C/A
7195 C/T

2434 APS*STOP
2421 AA*STOP
2412 RHHHHHSRTLVA*STOP (SEQ ID NO:162)
2406 STOP
2404 STOP
2516 DSGPARPRIPTSPTGPRASPALPPACSPRSPAFRRPSSKRRAPRSPGF
LSQAFGRLCALCGCQGRPEEPS*STOP (SEQ IS NO:163)
2515 SVP*STOP
2515 RVP*STOP
2514 VP*STOP
2508 H/Y, 2510*STOP
2507 *STOP
2494 GRQHPQPPATGA *STOP (SEQ ID NO:164)
2493 STOP
2399 STOP

FIG. 6C

SEQUENCE LISTING

```
<160> NUMBER OF SEQ ID NOS: 164

<210> SEQ ID NO 1
<211> LENGTH: 2556
<212> TYPE: PRT
<213> ORGANISM: Homo sapiens

<400> SEQUENCE: 1

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
                20                  25                  30

Asn Gly Gly Lys Cys Glu Ala Ala Asn Gly Thr Glu Ala Cys Val Cys
            35                  40                  45

Gly Gly Ala Phe Val Gly Pro Arg Cys Gln Asp Pro Asn Pro Cys Leu
        50                  55                  60

Ser Thr Pro Cys Lys Asn Ala Gly Thr Cys His Val Val Asp Arg Arg
65                  70                  75                  80
```

```
Gly Val Ala Asp Tyr Ala Cys Ser Cys Ala Leu Gly Phe Ser Gly Pro
                85                  90                  95
Leu Cys Leu Thr Pro Leu Asp Asn Ala Cys Leu Thr Asn Pro Cys Arg
               100                 105                 110
Asn Gly Gly Thr Cys Asp Leu Leu Thr Leu Thr Glu Tyr Lys Cys Arg
               115                 120                 125
Cys Pro Pro Gly Trp Ser Gly Lys Ser Cys Gln Gln Ala Asp Pro Cys
           130                 135                 140
Ala Ser Asn Pro Cys Ala Asn Gly Gly Gln Cys Leu Pro Phe Glu Ala
145                 150                 155                 160
Ser Tyr Ile Cys His Cys Pro Pro Ser Phe His Gly Pro Thr Cys Arg
                165                 170                 175
Gln Asp Val Asn Glu Cys Gly Gln Lys Pro Gly Leu Cys Arg His Gly
            180                 185                 190
Gly Thr Cys His Asn Glu Val Gly Ser Tyr Arg Cys Val Cys Arg Ala
            195                 200                 205
Thr His Thr Gly Pro Asn Cys Glu Arg Pro Tyr Val Pro Cys Ser Pro
210                 215                 220
Ser Pro Cys Gln Asn Gly Gly Thr Cys Arg Pro Thr Gly Asp Val Thr
225                 230                 235                 240
His Glu Cys Ala Cys Leu Pro Gly Phe Thr Gly Gln Asn Cys Glu Glu
                245                 250                 255
Asn Ile Asp Asp Cys Pro Gly Asn Asn Cys Lys Asn Gly Gly Ala Cys
                260                 265                 270
Val Asp Gly Val Asn Thr Tyr Asn Cys Arg Cys Pro Pro Glu Trp Thr
            275                 280                 285
Gly Gln Tyr Cys Thr Glu Asp Val Asp Glu Cys Gln Leu Met Pro Asn
            290                 295                 300
Ala Cys Gln Asn Gly Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe His Gly Ala Thr Cys His Asp
            340                 345                 350
Arg Val Ala Ser Phe Tyr Cys Glu Cys Pro His Gly Arg Thr Gly Leu
            355                 360                 365
Leu Cys His Leu Asn Asp Ala Cys Ile Ser Asn Pro Cys Asn Glu Gly
            370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
                405                 410                 415
Ser Leu Gly Ala Asn Pro Cys Glu His Ala Gly Lys Cys Ile Asn Thr
            420                 425                 430
Leu Gly Ser Phe Glu Cys Gln Cys Leu Gln Gly Tyr Thr Gly Pro Arg
            435                 440                 445
Cys Glu Ile Asp Val Asn Glu Cys Val Ser Asn Pro Cys Gln Asn Asp
450                 455                 460
Ala Thr Cys Leu Asp Gln Ile Gly Glu Phe Gln Cys Ile Cys Met Pro
465                 470                 475                 480
Gly Tyr Glu Gly Val His Cys Glu Val Asn Thr Asp Glu Cys Ala Ser
                485                 490                 495
Ser Pro Cys Leu His Asn Gly Arg Cys Leu Asp Lys Ile Asn Glu Phe
            500                 505                 510
```

```
Gln Cys Glu Cys Pro Thr Gly Phe Thr Gly His Leu Cys Gln Tyr Asp
            515                 520                 525
Val Asp Glu Cys Ala Ser Thr Pro Cys Lys Asn Gly Ala Lys Cys Leu
530                 535                 540
Asp Gly Pro Asn Thr Tyr Thr Cys Val Cys Thr Glu Gly Tyr Thr Gly
545                 550                 555                 560
Thr His Cys Glu Val Asp Ile Asp Glu Cys Asp Pro Asp Pro Cys His
                565                 570                 575
Tyr Gly Ser Cys Lys Asp Gly Val Ala Thr Phe Thr Cys Leu Cys Arg
            580                 585                 590
Pro Gly Tyr Thr Gly His His Cys Glu Thr Asn Ile Asn Glu Cys Ser
            595                 600                 605
Ser Gln Pro Cys Arg His Gly Gly Thr Cys Gln Asp Arg Asp Asn Ala
            610                 615                 620
Tyr Leu Cys Phe Cys Leu Lys Gly Thr Thr Gly Pro Asn Cys Glu Ile
625                 630                 635                 640
Asn Leu Asp Asp Cys Ala Ser Ser Pro Cys Asp Ser Gly Thr Cys Leu
                645                 650                 655
Asp Lys Ile Asp Gly Tyr Glu Cys Ala Cys Glu Pro Gly Tyr Thr Gly
            660                 665                 670
Ser Met Cys Asn Ile Asn Ile Asp Glu Cys Ala Gly Asn Pro Cys His
            675                 680                 685
Asn Gly Gly Thr Cys Glu Asp Gly Ile Asn Gly Phe Thr Cys Arg Cys
            690                 695                 700
Pro Glu Gly Tyr His Asp Pro Thr Cys Leu Ser Glu Val Asn Glu Cys
705                 710                 715                 720
Asn Ser Asn Pro Cys Val His Gly Ala Cys Arg Asp Ser Leu Asn Gly
                725                 730                 735
Tyr Lys Cys Asp Cys Asp Pro Gly Trp Ser Gly Thr Asn Cys Asp Ile
                740                 745                 750
Asn Asn Asn Glu Cys Glu Ser Asn Pro Cys Val Asn Gly Gly Thr Cys
            755                 760                 765
Lys Asp Met Thr Ser Gly Tyr Val Cys Thr Cys Arg Glu Gly Phe Ser
770                 775                 780
Gly Pro Asn Cys Gln Thr Asn Ile Asn Glu Cys Ala Ser Asn Pro Cys
785                 790                 795                 800
Leu Asn Gln Gly Thr Cys Ile Asp Asp Val Ala Gly Tyr Lys Cys Asn
                805                 810                 815
Cys Leu Leu Pro Tyr Thr Gly Ala Thr Cys Glu Val Val Leu Ala Pro
                820                 825                 830
Cys Ala Pro Ser Pro Cys Arg Asn Gly Gly Glu Cys Arg Gln Ser Glu
            835                 840                 845
Asp Tyr Glu Ser Phe Ser Cys Val Cys Pro Thr Gly Trp Gln Ala Gly
            850                 855                 860
Gln Thr Cys Glu Val Asp Ile Asn Glu Cys Val Leu Ser Pro Cys Arg
865                 870                 875                 880
His Gly Ala Ser Cys Gln Asn Thr His Gly Gly Tyr Arg Cys His Cys
                885                 890                 895
Gln Ala Gly Tyr Ser Gly Arg Asn Cys Glu Thr Asp Ile Asp Asp Cys
            900                 905                 910
Arg Pro Asn Pro Cys His Asn Gly Gly Ser Cys Thr Asp Gly Ile Asn
            915                 920                 925
Thr Ala Phe Cys Asp Cys Leu Pro Gly Phe Arg Gly Thr Phe Cys Glu
```

-continued

```
                 930                 935                 940
Glu Asp Ile Asn Glu Cys Ala Ser Asp Pro Cys Arg Asn Gly Ala Asn
945                 950                 955                 960

Cys Thr Asp Cys Val Asp Ser Tyr Thr Cys Thr Cys Pro Ala Gly Phe
                965                 970                 975

Ser Gly Ile His Cys Glu Asn Asn Thr Pro Asp Cys Thr Glu Ser Ser
                980                 985                 990

Cys Phe Asn Gly Gly Thr Cys Val Asp Gly Ile Asn Ser Phe Thr Cys
            995                1000                1005

Leu Cys Pro Pro Gly Phe Thr Gly Ser Tyr Cys Gln His Asp Val
    1010                1015                1020

Asn Glu Cys Asp Ser Gln Pro Cys Leu His Gly Thr Cys Gln
    1025                1030                1035

Asp Gly Cys Gly Ser Tyr Arg Cys Thr Cys Pro Gln Gly Tyr Thr
    1040                1045                1050

Gly Pro Asn Cys Gln Asn Leu Val His Trp Cys Asp Ser Ser Pro
    1055                1060                1065

Cys Lys Asn Gly Gly Lys Cys Trp Gln Thr His Thr Gln Tyr Arg
    1070                1075                1080

Cys Glu Cys Pro Ser Gly Trp Thr Gly Leu Tyr Cys Asp Val Pro
    1085                1090                1095

Ser Val Ser Cys Glu Val Ala Ala Gln Arg Gln Gly Val Asp Val
    1100                1105                1110

Ala Arg Leu Cys Gln His Gly Gly Leu Cys Val Asp Ala Gly Asn
    1115                1120                1125

Thr His His Cys Arg Cys Gln Ala Gly Tyr Thr Gly Ser Tyr Cys
    1130                1135                1140

Glu Asp Leu Val Asp Glu Cys Ser Pro Ser Pro Cys Gln Asn Gly
    1145                1150                1155

Ala Thr Cys Thr Asp Tyr Leu Gly Gly Tyr Ser Cys Lys Cys Val
    1160                1165                1170

Ala Gly Tyr His Gly Val Asn Cys Ser Glu Glu Ile Asp Glu Cys
    1175                1180                1185

Leu Ser His Pro Cys Gln Asn Gly Gly Thr Cys Leu Asp Leu Pro
    1190                1195                1200

Asn Thr Tyr Lys Cys Ser Cys Pro Arg Gly Thr Gln Gly Val His
    1205                1210                1215

Cys Glu Ile Asn Val Asp Asp Cys Asn Pro Pro Val Asp Pro Val
    1220                1225                1230

Ser Arg Ser Pro Lys Cys Phe Asn Asn Gly Thr Cys Val Asp Gln
    1235                1240                1245

Val Gly Gly Tyr Ser Cys Thr Cys Pro Pro Gly Phe Val Gly Glu
    1250                1255                1260

Arg Cys Glu Gly Asp Val Asn Glu Cys Leu Ser Asn Pro Cys Asp
    1265                1270                1275

Ala Arg Gly Thr Gln Asn Cys Val Gln Arg Val Asn Asp Phe His
    1280                1285                1290

Cys Glu Cys Arg Ala Gly His Thr Gly Arg Arg Cys Glu Ser Val
    1295                1300                1305

Ile Asn Gly Cys Lys Gly Lys Pro Cys Lys Asn Gly Gly Thr Cys
    1310                1315                1320

Ala Val Ala Ser Asn Thr Ala Arg Gly Phe Ile Cys Lys Cys Pro
    1325                1330                1335
```

-continued

```
Ala Gly Phe Glu Gly Ala Thr Cys Glu Asn Asp Ala Arg Thr Cys
    1340                1345                1350

Gly Ser Leu Arg Cys Leu Asn Gly Gly Thr Cys Ile Ser Gly Pro
    1355                1360                1365

Arg Ser Pro Thr Cys Leu Cys Leu Gly Pro Phe Thr Gly Pro Glu
    1370                1375                1380

Cys Gln Phe Pro Ala Ser Ser Pro Cys Leu Gly Gly Asn Pro Cys
    1385                1390                1395

Tyr Asn Gln Gly Thr Cys Glu Pro Thr Ser Glu Ser Pro Phe Tyr
    1400                1405                1410

Arg Cys Leu Cys Pro Ala Lys Phe Asn Gly Leu Leu Cys His Ile
    1415                1420                1425

Leu Asp Tyr Ser Phe Gly Gly Gly Ala Gly Arg Asp Ile Pro Pro
    1430                1435                1440

Pro Leu Ile Glu Glu Ala Cys Glu Leu Pro Glu Cys Gln Glu Asp
    1445                1450                1455

Ala Gly Asn Lys Val Cys Ser Leu Gln Cys Asn Asn His Ala Cys
    1460                1465                1470

Gly Trp Asp Gly Gly Asp Cys Ser Leu Asn Phe Asn Asp Pro Trp
    1475                1480                1485

Lys Asn Cys Thr Gln Ser Leu Gln Cys Trp Lys Tyr Phe Ser Asp
    1490                1495                1500

Gly His Cys Asp Ser Gln Cys Asn Ser Ala Gly Cys Leu Phe Asp
    1505                1510                1515

Gly Phe Asp Cys Gln Arg Ala Glu Gly Gln Cys Asn Pro Leu Tyr
    1520                1525                1530

Asp Gln Tyr Cys Lys Asp His Phe Ser Asp Gly His Cys Asp Gln
    1535                1540                1545

Gly Cys Asn Ser Ala Glu Cys Glu Trp Asp Gly Leu Asp Cys Ala
    1550                1555                1560

Glu His Val Pro Glu Arg Leu Ala Ala Gly Thr Leu Val Val Val
    1565                1570                1575

Val Leu Met Pro Pro Glu Gln Leu Arg Asn Ser Ser Phe His Phe
    1580                1585                1590

Leu Arg Glu Leu Ser Arg Val Leu His Thr Asn Val Val Phe Lys
    1595                1600                1605

Arg Asp Ala His Gly Gln Gln Met Ile Phe Pro Tyr Tyr Gly Arg
    1610                1615                1620

Glu Glu Glu Leu Arg Lys His Pro Ile Lys Arg Ala Ala Glu Gly
    1625                1630                1635

Trp Ala Ala Pro Asp Ala Leu Leu Gly Gln Val Lys Ala Ser Leu
    1640                1645                1650

Leu Pro Gly Gly Ser Glu Gly Gly Arg Arg Arg Glu Leu Asp
    1655                1660                1665

Pro Met Asp Val Arg Gly Ser Ile Val Tyr Leu Glu Ile Asp Asn
    1670                1675                1680

Arg Gln Cys Val Gln Ala Ser Ser Gln Cys Phe Gln Ser Ala Thr
    1685                1690                1695

Asp Val Ala Ala Phe Leu Gly Ala Leu Ala Ser Leu Gly Ser Leu
    1700                1705                1710

Asn Ile Pro Tyr Lys Ile Glu Ala Val Gln Ser Glu Thr Val Glu
    1715                1720                1725

Pro Pro Pro Pro Ala Gln Leu His Phe Met Tyr Val Ala Ala Ala
    1730                1735                1740
```

```
Ala Phe Val Leu Leu Phe Phe Val Gly Cys Gly Val Leu Leu Ser
    1745            1750                1755

Arg Lys Arg Arg Arg Gln His Gly Gln Leu Trp Phe Pro Glu Gly
    1760            1765                1770

Phe Lys Val Ser Glu Ala Ser Lys Lys Lys Arg Arg Glu Pro Leu
    1775            1780                1785

Gly Glu Asp Ser Val Gly Leu Lys Pro Leu Lys Asn Ala Ser Asp
    1790            1795                1800

Gly Ala Leu Met Asp Asp Asn Gln Asn Glu Trp Gly Asp Glu Asp
    1805            1810                1815

Leu Glu Thr Lys Lys Phe Arg Phe Glu Glu Pro Val Val Leu Pro
    1820            1825                1830

Asp Leu Asp Asp Gln Thr Asp His Arg Gln Trp Thr Gln Gln His
    1835            1840                1845

Leu Asp Ala Ala Asp Leu Arg Met Ser Ala Met Ala Pro Thr Pro
    1850            1855                1860

Pro Gln Gly Glu Val Asp Ala Asp Cys Met Asp Val Asn Val Arg
    1865            1870                1875

Gly Pro Asp Gly Phe Thr Pro Leu Met Ile Ala Ser Cys Ser Gly
    1880            1885                1890

Gly Gly Leu Glu Thr Gly Asn Ser Glu Glu Glu Glu Asp Ala Pro
    1895            1900                1905

Ala Val Ile Ser Asp Phe Ile Tyr Gln Gly Ala Ser Leu His Asn
    1910            1915                1920

Gln Thr Asp Arg Thr Gly Glu Thr Ala Leu His Leu Ala Ala Arg
    1925            1930                1935

Tyr Ser Arg Ser Asp Ala Ala Lys Arg Leu Leu Glu Ala Ser Ala
    1940            1945                1950

Asp Ala Asn Ile Gln Asp Asn Met Gly Arg Thr Pro Leu His Ala
    1955            1960                1965

Ala Val Ser Ala Asp Ala Gln Gly Val Phe Gln Ile Leu Ile Arg
    1970            1975                1980

Asn Arg Ala Thr Asp Leu Asp Ala Arg Met His Asp Gly Thr Thr
    1985            1990                1995

Pro Leu Ile Leu Ala Ala Arg Leu Ala Val Glu Gly Met Leu Glu
    2000            2005                2010

Asp Leu Ile Asn Ser His Ala Asp Val Asn Ala Val Asp Asp Leu
    2015            2020                2025

Gly Lys Ser Ala Leu His Trp Ala Ala Ala Val Asn Asn Val Asp
    2030            2035                2040

Ala Ala Val Val Leu Leu Lys Asn Gly Ala Asn Lys Asp Met Gln
    2045            2050                2055

Asn Asn Arg Glu Glu Thr Pro Leu Phe Leu Ala Ala Arg Glu Gly
    2060            2065                2070

Ser Tyr Glu Thr Ala Lys Val Leu Leu Asp His Phe Ala Asn Arg
    2075            2080                2085

Asp Ile Thr Asp His Met Asp Arg Leu Pro Arg Asp Ile Ala Gln
    2090            2095                2100

Glu Arg Met His His Asp Ile Val Arg Leu Leu Asp Glu Tyr Asn
    2105            2110                2115

Leu Val Arg Ser Pro Gln Leu His Gly Ala Pro Leu Gly Gly Thr
    2120            2125                2130

Pro Thr Leu Ser Pro Pro Leu Cys Ser Pro Asn Gly Tyr Leu Gly
```

-continued

```
                2135                2140                2145

Ser Leu Lys Pro Gly Val Gln Gly Lys Lys Val Arg Lys Pro Ser
    2150                2155                2160

Ser Lys Gly Leu Ala Cys Gly Ser Lys Glu Ala Lys Asp Leu Lys
    2165                2170                2175

Ala Arg Arg Lys Lys Ser Gln Asp Gly Lys Gly Cys Leu Leu Asp
    2180                2185                2190

Ser Ser Gly Met Leu Ser Pro Val Asp Ser Leu Glu Ser Pro His
    2195                2200                2205

Gly Tyr Leu Ser Asp Val Ala Ser Pro Pro Leu Leu Pro Ser Pro
    2210                2215                2220

Phe Gln Gln Ser Pro Ser Val Pro Leu Asn His Leu Pro Gly Met
    2225                2230                2235

Pro Asp Thr His Leu Gly Ile Gly His Leu Asn Val Ala Ala Lys
    2240                2245                2250

Pro Glu Met Ala Ala Leu Gly Gly Gly Arg Leu Ala Phe Glu
    2255                2260                2265

Thr Gly Pro Pro Arg Leu Ser His Leu Pro Val Ala Ser Gly Thr
    2270                2275                2280

Ser Thr Val Leu Gly Ser Ser Gly Gly Ala Leu Asn Phe Thr
    2285                2290                2295

Val Gly Gly Ser Thr Ser Leu Asn Gly Gln Cys Glu Trp Leu Ser
    2300                2305                2310

Arg Leu Gln Ser Gly Met Val Pro Asn Gln Tyr Asn Pro Leu Arg
    2315                2320                2325

Gly Ser Val Ala Pro Gly Pro Leu Ser Thr Gln Ala Pro Ser Leu
    2330                2335                2340

Gln His Gly Met Val Gly Pro Leu His Ser Ser Leu Ala Ala Ser
    2345                2350                2355

Ala Leu Ser Gln Met Met Ser Tyr Gln Gly Leu Pro Ser Thr Arg
    2360                2365                2370

Leu Ala Thr Gln Pro His Leu Val Gln Thr Gln Val Gln Pro
    2375                2380                2385

Gln Asn Leu Gln Met Gln Gln Gln Asn Leu Gln Pro Ala Asn Ile
    2390                2395                2400

Gln Gln Gln Gln Ser Leu Gln Pro Pro Pro Pro Pro Gln Pro
    2405                2410                2415

His Leu Gly Val Ser Ser Ala Ala Ser Gly His Leu Gly Arg Ser
    2420                2425                2430

Phe Leu Ser Gly Glu Pro Ser Gln Ala Asp Val Gln Pro Leu Gly
    2435                2440                2445

Pro Ser Ser Leu Ala Val His Thr Ile Leu Pro Gln Glu Ser Pro
    2450                2455                2460

Ala Leu Pro Thr Ser Leu Pro Ser Ser Leu Val Pro Pro Val Thr
    2465                2470                2475

Ala Ala Gln Phe Leu Thr Pro Pro Ser Gln His Ser Tyr Ser Ser
    2480                2485                2490

Pro Val Asp Asn Thr Pro Ser His Gln Leu Gln Val Pro Glu His
    2495                2500                2505

Pro Phe Leu Thr Pro Ser Pro Glu Ser Pro Asp Gln Trp Ser Ser
    2510                2515                2520

Ser Ser Pro His Ser Asn Val Ser Asp Trp Ser Glu Gly Val Ser
    2525                2530                2535
```

```
Ser Pro Pro Thr Ser Met Gln Ser Gln Ile Ala Arg Ile Pro Glu
    2540                2545                2550

Ala Phe Lys
    2555

<210> SEQ ID NO 2
<211> LENGTH: 2471
<212> TYPE: PRT
<213> ORGANISM: Homo sapiens

<400> SEQUENCE: 2

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
            20                  25                  30

Glu Pro Cys Val Asn Glu Gly Met Cys Val Thr Tyr His Asn Gly Thr
        35                  40                  45

Gly Tyr Cys Lys Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350
```

-continued

```
Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Gly Ala Thr Cys Ile Asn Gly Val Asn Gly Phe
    690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asp Asn Leu Val Asn Gly Tyr Arg Cys Thr Cys Lys
    770                 775                 780
```

-continued

```
Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
            805                 810                 815

Tyr Thr Cys His Cys Val Leu Pro Tyr Thr Gly Lys Asn Cys Gln Thr
                820                 825                 830

Val Leu Ala Pro Cys Ser Pro Asn Pro Cys Glu Asn Ala Ala Val Cys
            835                 840                 845

Lys Glu Ser Pro Asn Phe Glu Ser Tyr Thr Cys Leu Cys Ala Pro Gly
850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
                885                 890                 895

Cys Glu Cys Pro Pro Gly Phe Ser Gly Met Asp Cys Glu Glu Asp Ile
                900                 905                 910

Asp Asp Cys Leu Ala Asn Pro Cys Gln Asn Gly Gly Ser Cys Met Asp
            915                 920                 925

Gly Val Asn Thr Phe Ser Cys Leu Cys Leu Pro Gly Phe Thr Gly Asp
            930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
                965                 970                 975

Ala Gly Phe Asp Gly Val His Cys Glu Asn Asn Ile Asn Glu Cys Thr
                980                 985                 990

Glu Ser Ser Cys Phe Asn Gly Gly Thr Cys Val Asp Gly Ile Asn Ser
            995                 1000                1005

Phe Ser Cys Leu Cys Pro Val Gly Phe Thr Gly Ser Phe Cys Leu
    1010                1015                1020

His Glu Ile Asn Glu Cys Ser Ser His Pro Cys Leu Asn Glu Gly
    1025                1030                1035

Thr Cys Val Asp Gly Leu Gly Thr Tyr Arg Cys Ser Cys Pro Leu
    1040                1045                1050

Gly Tyr Thr Gly Lys Asn Cys Gln Thr Leu Val Asn Leu Cys Ser
    1055                1060                1065

Arg Ser Pro Cys Lys Asn Lys Gly Thr Cys Val Gln Lys Lys Ala
    1070                1075                1080

Glu Ser Gln Cys Leu Cys Pro Ser Gly Trp Ala Gly Ala Tyr Cys
    1085                1090                1095

Asp Val Pro Asn Val Ser Cys Asp Ile Ala Ala Ser Arg Arg Gly
    1100                1105                1110

Val Leu Val Glu His Leu Cys Gln His Ser Gly Val Cys Ile Asn
    1115                1120                1125

Ala Gly Asn Thr His Tyr Cys Gln Cys Pro Leu Gly Tyr Thr Gly
    1130                1135                1140

Ser Tyr Cys Glu Glu Gln Leu Asp Glu Cys Ala Ser Asn Pro Cys
    1145                1150                1155

Gln His Gly Ala Thr Cys Ser Asp Phe Ile Gly Gly Tyr Arg Cys
    1160                1165                1170

Glu Cys Val Pro Gly Tyr Gln Gly Val Asn Cys Glu Tyr Glu Val
    1175                1180                1185

Asp Glu Cys Gln Asn Gln Pro Cys Gln Asn Gly Gly Thr Cys Ile
```

```
                1190                1195               1200

Asp Leu Val Asn His Phe Lys Cys Ser Cys Pro Pro Gly Thr Arg
    1205                1210               1215

Gly Leu Leu Cys Glu Glu Asn Ile Asp Asp Cys Ala Arg Gly Pro
    1220                1225               1230

His Cys Leu Asn Gly Gly Gln Cys Met Asp Arg Ile Gly Gly Tyr
    1235                1240               1245

Ser Cys Arg Cys Leu Pro Gly Phe Ala Gly Glu Arg Cys Glu Gly
    1250                1255               1260

Asp Ile Asn Glu Cys Leu Ser Asn Pro Cys Ser Ser Glu Gly Ser
    1265                1270               1275

Leu Asp Cys Ile Gln Leu Thr Asn Asp Tyr Leu Cys Val Cys Arg
    1280                1285               1290

Ser Ala Phe Thr Gly Arg His Cys Glu Thr Phe Val Asp Val Cys
    1295                1300               1305

Pro Gln Met Pro Cys Leu Asn Gly Gly Thr Cys Ala Val Ala Ser
    1310                1315               1320

Asn Met Pro Asp Gly Phe Ile Cys Arg Cys Pro Pro Gly Phe Ser
    1325                1330               1335

Gly Ala Arg Cys Gln Ser Ser Cys Gly Gln Val Lys Cys Arg Lys
    1340                1345               1350

Gly Glu Gln Cys Val His Thr Ala Ser Gly Pro Arg Cys Phe Cys
    1355                1360               1365

Pro Ser Pro Arg Asp Cys Glu Ser Gly Cys Ala Ser Ser Pro Cys
    1370                1375               1380

Gln His Gly Gly Ser Cys His Pro Gln Arg Gln Pro Pro Tyr Tyr
    1385                1390               1395

Ser Cys Gln Cys Ala Pro Pro Phe Ser Gly Ser Arg Cys Glu Leu
    1400                1405               1410

Tyr Thr Ala Pro Pro Ser Thr Pro Pro Ala Thr Cys Leu Ser Gln
    1415                1420               1425

Tyr Cys Ala Asp Lys Ala Arg Asp Gly Val Cys Asp Glu Ala Cys
    1430                1435               1440

Asn Ser His Ala Cys Gln Trp Asp Gly Gly Asp Cys Ser Leu Thr
    1445                1450               1455

Met Glu Asn Pro Trp Ala Asn Cys Ser Ser Pro Leu Pro Cys Trp
    1460                1465               1470

Asp Tyr Ile Asn Asn Gln Cys Asp Glu Leu Cys Asn Thr Val Glu
    1475                1480               1485

Cys Leu Phe Asp Asn Phe Glu Cys Gln Gly Asn Ser Lys Thr Cys
    1490                1495               1500

Lys Tyr Asp Lys Tyr Cys Ala Asp His Phe Lys Asp Asn His Cys
    1505                1510               1515

Asp Gln Gly Cys Asn Ser Glu Glu Cys Gly Trp Asp Gly Leu Asp
    1520                1525               1530

Cys Ala Ala Asp Gln Pro Glu Asn Leu Ala Glu Gly Thr Leu Val
    1535                1540               1545

Ile Val Val Leu Met Pro Pro Glu Gln Leu Leu Gln Asp Ala Arg
    1550                1555               1560

Ser Phe Leu Arg Ala Leu Gly Thr Leu Leu His Thr Asn Leu Arg
    1565                1570               1575

Ile Lys Arg Asp Ser Gln Gly Glu Leu Met Val Tyr Pro Tyr Tyr
    1580                1585               1590
```

```
Gly Glu Lys Ser Ala Ala Met Lys Lys Gln Arg Met Thr Arg Arg
1595                1600                1605

Ser Leu Pro Gly Glu Gln Glu Gln Glu Val Ala Gly Ser Lys Val
1610                1615                1620

Phe Leu Glu Ile Asp Asn Arg Gln Cys Val Gln Asp Ser Asp His
1625                1630                1635

Cys Phe Lys Asn Thr Asp Ala Ala Ala Leu Leu Ala Ser His
1640                1645                1650

Ala Ile Gln Gly Thr Leu Ser Tyr Pro Leu Val Ser Val Val Ser
1655                1660                1665

Glu Ser Leu Thr Pro Glu Arg Thr Gln Leu Leu Tyr Leu Leu Ala
1670                1675                1680

Val Ala Val Val Ile Ile Leu Phe Ile Ile Leu Leu Gly Val Ile
1685                1690                1695

Met Ala Lys Arg Lys Arg Lys His Gly Ser Leu Trp Leu Pro Glu
1700                1705                1710

Gly Phe Thr Leu Arg Arg Asp Ala Ser Asn His Lys Arg Arg Glu
1715                1720                1725

Pro Val Gly Gln Asp Ala Val Gly Leu Lys Asn Leu Ser Val Gln
1730                1735                1740

Val Ser Glu Ala Asn Leu Ile Gly Thr Gly Thr Ser Glu His Trp
1745                1750                1755

Val Asp Asp Glu Gly Pro Gln Pro Lys Lys Val Lys Ala Glu Asp
1760                1765                1770

Glu Ala Leu Leu Ser Glu Glu Asp Asp Pro Ile Asp Arg Arg Pro
1775                1780                1785

Trp Thr Gln Gln His Leu Glu Ala Ala Asp Ile Arg Arg Thr Pro
1790                1795                1800

Ser Leu Ala Leu Thr Pro Pro Gln Ala Glu Gln Glu Val Asp Val
1805                1810                1815

Leu Asp Val Asn Val Arg Gly Pro Asp Gly Cys Thr Pro Leu Met
1820                1825                1830

Leu Ala Ser Leu Arg Gly Gly Ser Ser Asp Leu Ser Asp Glu Asp
1835                1840                1845

Glu Asp Ala Glu Asp Ser Ser Ala Asn Ile Ile Thr Asp Leu Val
1850                1855                1860

Tyr Gln Gly Ala Ser Leu Gln Ala Gln Thr Asp Arg Thr Gly Glu
1865                1870                1875

Met Ala Leu His Leu Ala Ala Arg Tyr Ser Arg Ala Asp Ala Ala
1880                1885                1890

Lys Arg Leu Leu Asp Ala Gly Ala Asp Ala Asn Ala Gln Asp Asn
1895                1900                1905

Met Gly Arg Cys Pro Leu His Ala Ala Val Ala Ala Asp Ala Gln
1910                1915                1920

Gly Val Phe Gln Ile Leu Ile Arg Asn Arg Val Thr Asp Leu Asp
1925                1930                1935

Ala Arg Met Asn Asp Gly Thr Thr Pro Leu Ile Leu Ala Ala Arg
1940                1945                1950

Leu Ala Val Glu Gly Met Val Ala Glu Leu Ile Asn Cys Gln Ala
1955                1960                1965

Asp Val Asn Ala Val Asp Asp His Gly Lys Ser Ala Leu His Trp
1970                1975                1980

Ala Ala Ala Val Asn Asn Val Glu Ala Thr Leu Leu Leu Leu Lys
1985                1990                1995
```

-continued

```
Asn Gly Ala Asn Arg Asp Met Gln Asp Asn Lys Glu Glu Thr Pro
    2000                2005                2010
Leu Phe Leu Ala Ala Arg Glu Gly Ser Tyr Glu Ala Ala Lys Ile
    2015                2020                2025
Leu Leu Asp His Phe Ala Asn Arg Asp Ile Thr Asp His Met Asp
    2030                2035                2040
Arg Leu Pro Arg Asp Val Ala Arg Asp Arg Met His His Asp Ile
    2045                2050                2055
Val Arg Leu Leu Asp Glu Tyr Asn Val Thr Pro Ser Pro Pro Gly
    2060                2065                2070
Thr Val Leu Thr Ser Ala Leu Ser Pro Val Ile Cys Gly Pro Asn
    2075                2080                2085
Arg Ser Phe Leu Ser Leu Lys His Thr Pro Met Gly Lys Lys Ser
    2090                2095                2100
Arg Arg Pro Ser Ala Lys Ser Thr Met Pro Thr Ser Leu Pro Asn
    2105                2110                2115
Leu Ala Lys Glu Ala Lys Asp Ala Lys Gly Ser Arg Arg Lys Lys
    2120                2125                2130
Ser Leu Ser Glu Lys Val Gln Leu Ser Glu Ser Ser Val Thr Leu
    2135                2140                2145
Ser Pro Val Asp Ser Leu Glu Ser Pro His Thr Tyr Val Ser Asp
    2150                2155                2160
Thr Thr Ser Ser Pro Met Ile Thr Ser Pro Gly Ile Leu Gln Ala
    2165                2170                2175
Ser Pro Asn Pro Met Leu Ala Thr Ala Ala Pro Pro Ala Pro Val
    2180                2185                2190
His Ala Gln His Ala Leu Ser Phe Ser Asn Leu His Glu Met Gln
    2195                2200                2205
Pro Leu Ala His Gly Ala Ser Thr Val Leu Pro Ser Val Ser Gln
    2210                2215                2220
Leu Leu Ser His His His Ile Val Ser Pro Gly Ser Gly Ser Ala
    2225                2230                2235
Gly Ser Leu Ser Arg Leu His Pro Val Pro Val Pro Ala Asp Trp
    2240                2245                2250
Met Asn Arg Met Glu Val Asn Glu Thr Gln Tyr Asn Glu Met Phe
    2255                2260                2265
Gly Met Val Leu Ala Pro Ala Glu Gly Thr His Pro Gly Ile Ala
    2270                2275                2280
Pro Gln Ser Arg Pro Pro Glu Gly Lys His Ile Thr Thr Pro Arg
    2285                2290                2295
Glu Pro Leu Pro Pro Ile Val Thr Phe Gln Leu Ile Pro Lys Gly
    2300                2305                2310
Ser Ile Ala Gln Pro Ala Gly Ala Pro Gln Pro Gln Ser Thr Cys
    2315                2320                2325
Pro Pro Ala Val Ala Gly Pro Leu Pro Thr Met Tyr Gln Ile Pro
    2330                2335                2340
Glu Met Ala Arg Leu Pro Ser Val Ala Phe Pro Thr Ala Met Met
    2345                2350                2355
Pro Gln Gln Asp Gly Gln Val Ala Gln Thr Ile Leu Pro Ala Tyr
    2360                2365                2370
His Pro Phe Pro Ala Ser Val Gly Lys Tyr Pro Thr Pro Pro Ser
    2375                2380                2385
Gln His Ser Tyr Ala Ser Ser Asn Ala Ala Glu Arg Thr Pro Ser
```

```
                2390                2395                2400
His  Ser  Gly  His  Leu  Gln  Gly  Glu  His  Pro  Tyr  Leu  Thr  Pro  Ser
     2405                2410                2415

Pro  Glu  Ser  Pro  Asp  Gln  Trp  Ser  Ser  Ser  Pro  His  Ser  Ala
     2420                2425                2430

Ser  Asp  Trp  Ser  Asp  Val  Thr  Thr  Ser  Pro  Thr  Pro  Gly  Gly  Ala
     2435                2440                2445

Gly  Gly  Gly  Gln  Arg  Gly  Pro  Gly  Thr  His  Met  Ser  Glu  Pro  Pro
     2450                2455                2460

His  Asn  Asn  Met  Gln  Val  Tyr  Ala
     2465                2470

<210> SEQ ID NO 3
<211> LENGTH: 2319
<212> TYPE: PRT
<213> ORGANISM: Homo sapiens

<400> SEQUENCE: 3

Met  Gly  Leu  Gly  Ala  Arg  Gly  Arg  Arg  Arg  Arg  Leu  Met  Ala
1              5                   10                  15

Leu  Pro  Pro  Pro  Pro  Pro  Met  Arg  Ala  Leu  Pro  Leu  Leu  Leu
          20                  25                  30

Leu  Ala  Gly  Leu  Gly  Ala  Ala  Pro  Pro  Cys  Leu  Asp  Gly  Ser  Pro
          35                  40                  45

Cys  Ala  Asn  Gly  Gly  Arg  Cys  Thr  His  Gln  Gln  Pro  Ser  Leu  Glu  Ala
50                  55                  60

Ala  Cys  Leu  Cys  Leu  Pro  Gly  Trp  Val  Gly  Glu  Arg  Cys  Gln  Leu  Glu
65                  70                  75                  80

Asp  Pro  Cys  His  Ser  Gly  Pro  Cys  Ala  Gly  Arg  Gly  Val  Cys  Gln  Ser
                    85                  90                  95

Ser  Val  Val  Ala  Gly  Thr  Ala  Arg  Phe  Ser  Cys  Arg  Cys  Leu  Arg  Gly
          100                 105                 110

Phe  Gln  Gly  Pro  Asp  Cys  Ser  Gln  Pro  Asp  Pro  Cys  Val  Ser  Arg  Pro
          115                 120                 125

Cys  Val  His  Gly  Ala  Pro  Cys  Ser  Val  Gly  Pro  Asp  Gly  Arg  Phe  Ala
     130                 135                 140

Cys  Ala  Cys  Pro  Pro  Gly  Tyr  Gln  Gly  Gln  Ser  Cys  Gln  Ser  Asp  Ile
145                 150                 155                 160

Asp  Glu  Cys  Arg  Ser  Gly  Thr  Thr  Cys  Arg  His  Gly  Gly  Thr  Cys  Leu
                    165                 170                 175

Asn  Thr  Pro  Gly  Ser  Phe  Arg  Cys  Gln  Cys  Pro  Leu  Gly  Tyr  Thr  Gly
          180                 185                 190

Leu  Leu  Cys  Glu  Asn  Pro  Val  Val  Pro  Cys  Ala  Pro  Ser  Pro  Cys  Arg
          195                 200                 205

Asn  Gly  Gly  Thr  Cys  Arg  Gln  Ser  Ser  Asp  Val  Thr  Tyr  Asp  Cys  Ala
     210                 215                 220

Cys  Leu  Pro  Gly  Phe  Glu  Gly  Gln  Asn  Cys  Glu  Val  Asn  Val  Asp  Asp
225                 230                 235                 240

Cys  Pro  Gly  His  Arg  Cys  Leu  Asn  Gly  Gly  Thr  Cys  Val  Asp  Gly  Val
                    245                 250                 255

Asn  Thr  Tyr  Asn  Cys  Gln  Cys  Pro  Pro  Glu  Trp  Thr  Gly  Gln  Phe  Cys
          260                 265                 270

Thr  Glu  Asp  Val  Asp  Glu  Cys  Gln  Leu  Gln  Pro  Asn  Ala  Cys  His  Asn
          275                 280                 285

Gly  Gly  Thr  Cys  Phe  Asn  Leu  Leu  Gly  Gly  His  Ser  Cys  Val  Cys  Val
```

```
                 290                 295                 300
Asn Gly Trp Thr Gly Glu Ser Cys Ser Gln Asn Ile Asp Asp Cys Ala
305                 310                 315                 320

Thr Ala Val Cys Phe His Gly Ala Thr Cys His Asp Arg Val Ala Ser
                325                 330                 335

Phe Tyr Cys Ala Cys Pro Met Gly Lys Thr Gly Leu Leu Cys His Leu
                340                 345                 350

Asp Asp Ala Cys Val Ser Asn Pro Cys His Glu Asp Ala Ile Cys Asp
                355                 360                 365

Thr Asn Pro Val Ser Gly Arg Ala Ile Cys Thr Cys Pro Pro Gly Phe
370                 375                 380

Thr Gly Gly Ala Cys Asp Gln Asp Val Asp Glu Cys Ser Ile Gly Ala
385                 390                 395                 400

Asn Pro Cys Glu His Leu Gly Arg Cys Val Asn Thr Gln Gly Ser Phe
                405                 410                 415

Leu Cys Gln Cys Gly Arg Gly Tyr Thr Gly Pro Arg Cys Glu Thr Asp
                420                 425                 430

Val Asn Glu Cys Leu Ser Gly Pro Cys Arg Asn Gln Ala Thr Cys Leu
                435                 440                 445

Asp Arg Ile Gly Gln Phe Thr Cys Ile Cys Met Ala Gly Phe Thr Gly
                450                 455                 460

Thr Tyr Cys Glu Val Asp Ile Asp Glu Cys Gln Ser Ser Pro Cys Val
465                 470                 475                 480

Asn Gly Gly Val Cys Lys Asp Arg Val Asn Gly Phe Ser Cys Thr Cys
                485                 490                 495

Pro Ser Gly Phe Ser Gly Ser Met Cys Gln Leu Asp Val Asp Glu Cys
                500                 505                 510

Ala Ser Thr Pro Cys Arg Asn Gly Ala Lys Cys Val Asp Gln Pro Asp
                515                 520                 525

Gly Tyr Glu Cys Arg Cys Ala Glu Gly Phe Glu Gly Thr Leu Cys Glu
                530                 535                 540

Arg Asn Val Asp Asp Cys Ser Pro Asp Pro Cys His His Gly Arg Cys
545                 550                 555                 560

Val Asp Gly Ile Ala Ser Phe Ser Cys Ala Cys Ala Pro Gly Tyr Thr
                565                 570                 575

Gly Ile Arg Cys Glu Ser Gln Val Asp Glu Cys Arg Ser Gln Pro Cys
                580                 585                 590

Arg Tyr Gly Gly Lys Cys Leu Asp Leu Val Asp Lys Tyr Leu Cys Arg
                595                 600                 605

Cys Pro Pro Gly Thr Thr Gly Val Asn Cys Glu Val Asn Ile Asp Asp
610                 615                 620

Cys Ala Ser Asn Pro Cys Thr Phe Gly Val Cys Arg Asp Gly Ile Asn
625                 630                 635                 640

Arg Tyr Asp Cys Val Cys Gln Pro Gly Phe Thr Gly Pro Leu Cys Asn
                645                 650                 655

Val Glu Ile Asn Glu Cys Ala Ser Ser Pro Cys Gly Glu Gly Gly Ser
                660                 665                 670

Cys Val Asp Gly Glu Asn Gly Phe His Cys Leu Cys Pro Pro Gly Ser
                675                 680                 685

Leu Pro Pro Leu Cys Leu Pro Ala Asn His Pro Cys Ala His Lys Pro
                690                 695                 700

Cys Ser His Gly Val Cys His Asp Ala Pro Gly Gly Phe Arg Cys Val
705                 710                 715                 720
```

```
Cys Glu Pro Gly Trp Ser Gly Pro Arg Cys Ser Gln Ser Leu Ala Pro
            725                 730                 735

Asp Ala Cys Glu Ser Gln Pro Cys Ala Gly Gly Thr Cys Thr Ser
        740                 745                 750

Asp Gly Ile Gly Phe Arg Cys Thr Cys Ala Pro Gly Phe Gln Gly His
            755                 760                 765

Gln Cys Glu Val Leu Ser Pro Cys Thr Pro Ser Leu Cys Glu His Gly
    770                 775                 780

Gly His Cys Glu Ser Asp Pro Asp Arg Leu Thr Val Cys Ser Cys Pro
785                 790                 795                 800

Pro Gly Trp Gln Gly Pro Arg Cys Gln Gln Asp Val Asp Glu Cys Ala
                805                 810                 815

Gly Ala Ser Pro Cys Gly Pro His Gly Thr Cys Thr Asn Leu Pro Gly
            820                 825                 830

Asn Phe Arg Cys Ile Cys His Arg Gly Tyr Thr Gly Pro Phe Cys Asp
            835                 840                 845

Gln Asp Ile Asp Asp Cys Asp Pro Asn Pro Cys Leu His Gly Gly Ser
    850                 855                 860

Cys Gln Asp Gly Val Gly Ser Phe Ser Cys Ser Cys Leu Asp Gly Phe
865                 870                 875                 880

Ala Gly Pro Arg Cys Ala Arg Asp Val Asp Glu Cys Leu Ser Ser Pro
                885                 890                 895

Cys Gly Pro Gly Thr Cys Thr Asp His Val Ala Ser Phe Thr Cys Ala
                900                 905                 910

Cys Pro Pro Gly Tyr Gly Gly Phe His Cys Glu Ile Asp Leu Pro Asp
                915                 920                 925

Cys Ser Pro Ser Ser Cys Phe Asn Gly Gly Thr Cys Val Asp Gly Val
    930                 935                 940

Ser Ser Phe Ser Cys Leu Cys Arg Pro Gly Tyr Thr Gly Thr His Cys
945                 950                 955                 960

Gln Tyr Glu Ala Asp Pro Cys Phe Ser Arg Pro Cys Leu His Gly Gly
                965                 970                 975

Ile Cys Asn Pro Thr His Pro Gly Phe Glu Cys Thr Cys Arg Glu Gly
            980                 985                 990

Phe Thr Gly Ser Gln Cys Gln Asn Pro Val Asp Trp Cys Ser Gln Ala
            995                1000                1005

Pro Cys Gln Asn Gly Gly Arg Cys Val Gln Thr Gly Ala Tyr Cys
    1010                1015                1020

Ile Cys Pro Pro Gly Trp Ser Gly Arg Leu Cys Asp Ile Gln Ser
    1025                1030                1035

Leu Pro Cys Thr Glu Ala Ala Ala Gln Met Gly Val Arg Leu Glu
    1040                1045                1050

Gln Leu Cys Gln Glu Gly Gly Lys Cys Ile Asp Lys Gly Arg Ser
    1055                1060                1065

His Tyr Cys Val Cys Pro Glu Gly Arg Thr Gly Ser His Cys Glu
    1070                1075                1080

His Glu Val Asp Pro Cys Thr Ala Gln Pro Cys Gln His Gly Gly
    1085                1090                1095

Thr Cys Arg Gly Tyr Met Gly Gly Tyr Val Cys Glu Cys Pro Ala
    1100                1105                1110

Gly Tyr Ala Gly Asp Ser Cys Glu Asp Asn Ile Asp Glu Cys Ala
    1115                1120                1125

Ser Gln Pro Cys Gln Asn Gly Gly Ser Cys Ile Asp Leu Val Ala
    1130                1135                1140
```

```
Arg Tyr Leu Cys Ser Cys Pro Pro Gly Thr Leu Gly Val Leu Cys
    1145            1150              1155

Glu Ile Asn Glu Asp Asp Cys Asp Leu Gly Pro Ser Leu Asp Ser
    1160            1165              1170

Gly Val Gln Cys Leu His Asn Gly Thr Cys Val Asp Leu Val Gly
    1175            1180              1185

Gly Phe Arg Cys Asn Cys Pro Pro Gly Tyr Thr Gly Leu His Cys
    1190            1195              1200

Glu Ala Asp Ile Asn Glu Cys Arg Pro Gly Ala Cys His Ala Ala
    1205            1210              1215

His Thr Arg Asp Cys Leu Gln Asp Pro Gly Gly His Phe Arg Cys
    1220            1225              1230

Val Cys His Pro Gly Phe Thr Gly Pro Arg Cys Gln Ile Ala Leu
    1235            1240              1245

Ser Pro Cys Glu Ser Gln Pro Cys Gln His Gly Gly Gln Cys Arg
    1250            1255              1260

His Ser Leu Gly Arg Gly Gly Leu Thr Phe Thr Cys His Cys
    1265            1270              1275

Val Pro Pro Phe Trp Gly Leu Arg Cys Glu Arg Val Ala Arg Ser
    1280            1285              1290

Cys Arg Glu Leu Gln Cys Pro Val Gly Ile Pro Cys Gln Gln Thr
    1295            1300              1305

Ala Arg Gly Pro Arg Cys Ala Cys Pro Pro Gly Leu Ser Gly Pro
    1310            1315              1320

Ser Cys Arg Val Ser Arg Ala Ser Pro Ser Gly Ala Thr Asn Ala
    1325            1330              1335

Ser Cys Ala Ser Ala Pro Cys Leu His Gly Gly Ser Cys Leu Pro
    1340            1345              1350

Val Gln Ser Val Pro Phe Phe Arg Cys Val Cys Ala Pro Gly Trp
    1355            1360              1365

Gly Gly Pro Arg Cys Glu Thr Pro Ser Ala Ala Pro Glu Val Pro
    1370            1375              1380

Glu Glu Pro Arg Cys Pro Arg Ala Ala Cys Gln Ala Lys Arg Gly
    1385            1390              1395

Asp Gln Asn Cys Asp Arg Glu Cys Asn Thr Pro Gly Cys Gly Trp
    1400            1405              1410

Asp Gly Gly Asp Cys Ser Leu Asn Val Asp Asp Pro Trp Arg Gln
    1415            1420              1425

Cys Glu Ala Leu Gln Cys Trp Arg Leu Phe Asn Asn Ser Arg Cys
    1430            1435              1440

Asp Pro Ala Cys Ser Ser Pro Ala Cys Leu Tyr Asp Asn Phe Asp
    1445            1450              1455

Cys Tyr Ser Gly Gly Arg Asp Arg Thr Cys Asn Pro Val Tyr Glu
    1460            1465              1470

Lys Tyr Cys Ala Asp His Phe Ala Asp Gly Arg Cys Asp Gln Gly
    1475            1480              1485

Cys Asn Thr Glu Glu Cys Gly Trp Asp Gly Leu Asp Cys Ala Ser
    1490            1495              1500

Glu Val Pro Ala Leu Leu Ala Arg Gly Val Leu Val Leu Thr Val
    1505            1510              1515

Leu Leu Pro Pro Glu Glu Leu Leu Arg Ser Ser Ala Asp Phe Leu
    1520            1525              1530

Gln Arg Leu Ser Ala Ile Leu Arg Thr Ser Leu Arg Phe Arg Leu
```

```
            1535                1540                1545

Asp Ala Arg Gly Gln Ala Met Val Phe Pro Tyr His Arg Pro Ser
    1550                1555                1560

Pro Gly Ser Glu Ser Arg Val Arg Arg Glu Leu Gly Pro Glu Val
    1565                1570                1575

Ile Gly Ser Val Val Met Leu Glu Ile Asp Asn Arg Leu Cys Leu
    1580                1585                1590

Gln Ser Ala Glu Asn Asp His Cys Phe Pro Asp Ala Gln Ser Ala
    1595                1600                1605

Ala Asp Tyr Leu Gly Ala Leu Ser Ala Val Glu Arg Leu Asp Phe
    1610                1615                1620

Pro Tyr Pro Leu Arg Asp Val Arg Gly Glu Pro Leu Glu Ala Pro
    1625                1630                1635

Glu Gln Ser Val Pro Leu Leu Pro Leu Leu Val Ala Gly Ala Val
    1640                1645                1650

Phe Leu Leu Ile Ile Phe Ile Leu Gly Val Met Val Ala Arg Arg
    1655                1660                1665

Lys Arg Glu His Ser Thr Leu Trp Phe Pro Glu Gly Phe Ala Leu
    1670                1675                1680

His Lys Asp Ile Ala Ala Gly His Lys Gly Arg Arg Glu Pro Val
    1685                1690                1695

Gly Gln Asp Ala Leu Gly Met Lys Asn Met Ala Lys Gly Glu Ser
    1700                1705                1710

Leu Met Gly Glu Val Val Thr Asp Leu Asn Asp Ser Glu Cys Pro
    1715                1720                1725

Glu Ala Lys Arg Leu Lys Val Glu Glu Pro Gly Met Gly Ala Glu
    1730                1735                1740

Glu Pro Glu Asp Cys Arg Gln Trp Thr Gln His His Leu Val Ala
    1745                1750                1755

Ala Asp Ile Arg Val Ala Pro Ala Thr Ala Leu Thr Pro Pro Gln
    1760                1765                1770

Gly Asp Ala Asp Ala Asp Gly Val Asp Val Asn Val Arg Gly Pro
    1775                1780                1785

Asp Gly Phe Thr Pro Leu Met Leu Ala Ser Phe Cys Gly Gly Ala
    1790                1795                1800

Leu Glu Pro Met Pro Ala Glu Asp Glu Ala Asp Asp Thr Ser
    1805                1810                1815

Ala Ser Ile Ile Ser Asp Leu Ile Cys Gln Gly Ala Gln Leu Gly
    1820                1825                1830

Ala Arg Thr Asp Arg Thr Gly Glu Thr Ala Leu His Leu Ala Ala
    1835                1840                1845

Arg Tyr Ala Arg Ala Asp Ala Ala Lys Arg Leu Leu Asp Ala Gly
    1850                1855                1860

Ala Asp Thr Asn Ala Gln Asp His Ser Gly Arg Thr Pro Leu His
    1865                1870                1875

Thr Ala Val Thr Ala Asp Ala Gln Gly Val Phe Gln Ile Leu Ile
    1880                1885                1890

Arg Asn Arg Ser Thr Asp Leu Asp Ala Arg Met Ala Asp Gly Ser
    1895                1900                1905

Thr Ala Leu Ile Leu Ala Ala Arg Leu Ala Val Glu Gly Met Val
    1910                1915                1920

Glu Glu Leu Ile Ala Ser His Ala Asp Val Asn Ala Val Asp Glu
    1925                1930                1935
```

```
Leu Gly Lys Ser Ala Leu His Trp Ala Ala Val Asn Asn Val
    1940            1945            1950

Glu Ala Thr Leu Ala Leu Leu Lys Asn Gly Ala Asn Lys Asp Met
    1955            1960            1965

Gln Asp Ser Lys Glu Glu Thr Pro Leu Phe Leu Ala Ala Arg Glu
    1970            1975            1980

Gly Ser Tyr Glu Ala Ala Lys Leu Leu Leu Asp His Leu Ala Asn
    1985            1990            1995

Arg Glu Ile Thr Asp His Leu Asp Arg Leu Pro Arg Asp Val Ala
    2000            2005            2010

Gln Glu Arg Leu His Gln Asp Ile Val Arg Leu Leu Asp Gln Pro
    2015            2020            2025

Ser Gly Pro Arg Ser Pro Ser Gly Pro His Gly Leu Gly Pro Leu
    2030            2035            2040

Leu Cys Pro Pro Gly Ala Phe Leu Pro Gly Leu Lys Ala Val Gln
    2045            2050            2055

Ser Gly Thr Lys Lys Ser Arg Arg Pro Pro Gly Lys Thr Gly Leu
    2060            2065            2070

Gly Pro Gln Gly Thr Arg Gly Arg Gly Lys Lys Leu Thr Leu Ala
    2075            2080            2085

Cys Pro Gly Pro Leu Ala Asp Ser Ser Val Thr Leu Ser Pro Val
    2090            2095            2100

Asp Ser Leu Asp Ser Pro Arg Pro Phe Ser Gly Pro Pro Ala Ser
    2105            2110            2115

Pro Gly Gly Phe Pro Leu Glu Gly Pro Tyr Ala Thr Thr Ala Thr
    2120            2125            2130

Ala Val Ser Leu Ala Gln Leu Gly Ala Ser Arg Ala Gly Pro Leu
    2135            2140            2145

Gly Arg Gln Pro Pro Gly Gly Cys Val Leu Ser Phe Gly Leu Leu
    2150            2155            2160

Asn Pro Val Ala Val Pro Leu Asp Trp Ala Arg Leu Pro Pro Pro
    2165            2170            2175

Ala Pro Pro Gly Pro Ser Phe Leu Leu Pro Leu Ala Pro Gly Pro
    2180            2185            2190

Gln Leu Leu Asn Pro Gly Ala Pro Val Ser Pro Gln Glu Arg Pro
    2195            2200            2205

Pro Pro Tyr Leu Ala Ala Pro Gly His Gly Glu Glu Tyr Pro Ala
    2210            2215            2220

Ala Gly Thr Arg Ser Ser Pro Thr Lys Ala Arg Phe Leu Arg Val
    2225            2230            2235

Pro Ser Glu His Pro Tyr Leu Thr Pro Ser Pro Glu Ser Pro Glu
    2240            2245            2250

His Trp Ala Ser Pro Ser Pro Ser Leu Ser Asp Trp Ser Asp
    2255            2260            2265

Ser Thr Pro Ser Pro Ala Thr Ala Thr Asn Ala Thr Ala Ser Gly
    2270            2275            2280

Ala Leu Pro Ala Gln Pro His Pro Ile Ser Val Pro Ser Leu Pro
    2285            2290            2295

Gln Ser Gln Thr Gln Leu Gly Pro Gln Pro Glu Val Thr Pro Lys
    2300            2305            2310

Arg Gln Val Met Ala Glx
    2315

<210> SEQ ID NO 4
```

<211> LENGTH: 2002
<212> TYPE: PRT
<213> ORGANISM: Homo sapiens

<400> SEQUENCE: 4

```
Met Gln Pro Pro Ser Leu Leu Leu Leu Leu Leu Leu Leu Leu Leu Cys
1               5                   10                  15

Val Ser Val Arg Pro Arg Gly Leu Leu Cys Gly Ser Phe Pro Glu
            20                  25                  30

Pro Cys Ala Asn Gly Gly Thr Cys Leu Ser Leu Ser Leu Gly Gln Gly
            35                  40                  45

Thr Cys Gln Cys Ala Pro Gly Phe Leu Gly Glu Thr Cys Gln Phe Pro
    50                  55                  60

Asp Pro Cys Gln Asn Ala Gln Leu Cys Gln Asn Gly Gly Ser Cys Gln
65                  70                  75                  80

Ala Leu Leu Pro Ala Pro Leu Gly Leu Pro Ser Ser Pro Ser Pro Leu
                85                  90                  95

Thr Pro Ser Phe Leu Cys Thr Cys Leu Pro Gly Phe Thr Gly Glu Arg
            100                 105                 110

Cys Gln Ala Lys Leu Glu Asp Pro Cys Pro Pro Ser Phe Cys Ser Lys
        115                 120                 125

Arg Gly Arg Cys His Ile Gln Ala Ser Gly Arg Pro Gln Cys Ser Cys
    130                 135                 140

Met Pro Gly Trp Thr Gly Glu Gln Cys Gln Leu Arg Asp Phe Cys Ser
145                 150                 155                 160

Ala Asn Pro Cys Val Asn Gly Gly Val Cys Leu Ala Thr Tyr Pro Gln
                165                 170                 175

Ile Gln Cys His Cys Pro Pro Gly Phe Glu Gly His Ala Cys Glu Arg
            180                 185                 190

Asp Val Asn Glu Cys Phe Gln Asp Pro Gly Pro Cys Pro Lys Gly Thr
        195                 200                 205

Ser Cys His Asn Thr Leu Gly Ser Phe Gln Cys Leu Cys Pro Val Gly
    210                 215                 220

Gln Glu Gly Pro Arg Cys Glu Leu Arg Ala Gly Pro Cys Pro Pro Arg
225                 230                 235                 240

Gly Cys Ser Asn Gly Gly Thr Cys Gln Leu Met Pro Glu Lys Asp Ser
                245                 250                 255

Thr Phe His Leu Cys Leu Cys Pro Pro Gly Phe Ile Gly Pro Gly Cys
            260                 265                 270

Glu Val Asn Pro Asp Asn Cys Val Ser His Gln Cys Gln Asn Gly Gly
        275                 280                 285

Thr Cys Gln Asp Gly Leu Asp Thr Tyr Thr Cys Leu Cys Pro Glu Thr
    290                 295                 300

Trp Thr Gly Trp Asp Cys Ser Glu Asp Val Asp Glu Cys Glu Ala Gln
305                 310                 315                 320

Gly Pro Pro His Cys Arg Asn Gly Gly Thr Cys Gln Asn Ser Ala Gly
                325                 330                 335

Ser Phe His Cys Val Cys Val Ser Gly Trp Gly Gly Thr Ser Cys Glu
            340                 345                 350

Glu Asn Leu Asp Asp Cys Ile Ala Ala Thr Cys Ala Pro Gly Ser Thr
        355                 360                 365

Cys Ile Asp Arg Val Gly Ser Phe Ser Cys Leu Cys Pro Pro Gly Arg
    370                 375                 380

Thr Gly Leu Leu Cys His Leu Glu Asp Met Cys Leu Ser Gln Pro Cys
385                 390                 395                 400
```

His Gly Asp Ala Gln Cys Ser Thr Asn Pro Leu Thr Gly Ser Thr Leu
             405                 410                 415

Cys Leu Cys Gln Pro Gly Tyr Ser Gly Pro Thr Cys His Gln Asp Leu
         420                 425                 430

Asp Glu Cys Leu Met Ala Gln Gln Gly Pro Ser Pro Cys Glu His Gly
             435                 440                 445

Gly Ser Cys Leu Asn Thr Pro Gly Ser Phe Asn Cys Leu Cys Pro Pro
         450                 455                 460

Gly Tyr Thr Gly Ser Arg Cys Glu Ala Asp His Asn Glu Cys Leu Ser
465                 470                 475                 480

Gln Pro Cys His Pro Gly Ser Thr Cys Leu Asp Leu Leu Ala Thr Phe
             485                 490                 495

His Cys Leu Cys Pro Pro Gly Leu Glu Gly Gln Leu Cys Glu Val Glu
             500                 505                 510

Thr Asn Glu Cys Ala Ser Ala Pro Cys Leu Asn His Ala Asp Cys His
             515                 520                 525

Asp Leu Leu Asn Gly Phe Gln Cys Ile Cys Leu Pro Gly Phe Ser Gly
         530                 535                 540

Thr Arg Cys Glu Glu Asp Ile Asp Glu Cys Arg Ser Ser Pro Cys Ala
545                 550                 555                 560

Asn Gly Gly Gln Cys Gln Asp Gln Pro Gly Ala Phe His Cys Lys Cys
                 565                 570                 575

Leu Pro Gly Phe Glu Gly Pro Arg Cys Gln Thr Glu Val Asp Glu Cys
             580                 585                 590

Leu Ser Asp Pro Cys Pro Val Gly Ala Ser Cys Leu Asp Leu Pro Gly
         595                 600                 605

Ala Phe Phe Cys Leu Cys Pro Ser Gly Phe Thr Gly Gln Leu Cys Glu
         610                 615                 620

Val Pro Leu Cys Ala Pro Asn Leu Cys Gln Pro Lys Gln Ile Cys Lys
625                 630                 635                 640

Asp Gln Lys Asp Lys Ala Asn Cys Leu Cys Pro Asp Gly Ser Pro Gly
                 645                 650                 655

Cys Ala Pro Pro Glu Asp Asn Cys Thr Cys His His Gly His Cys Gln
             660                 665                 670

Arg Ser Ser Cys Val Cys Asp Val Gly Trp Thr Gly Pro Glu Cys Glu
         675                 680                 685

Ala Glu Leu Gly Gly Cys Ile Ser Ala Pro Cys Ala His Gly Gly Thr
         690                 695                 700

Cys Tyr Pro Gln Pro Ser Gly Tyr Asn Cys Thr Cys Pro Thr Gly Tyr
705                 710                 715                 720

Thr Gly Pro Thr Cys Ser Glu Glu Met Thr Ala Cys His Ser Gly Pro
                 725                 730                 735

Cys Leu Asn Gly Gly Ser Cys Asn Pro Ser Pro Gly Gly Tyr Tyr Cys
             740                 745                 750

Thr Cys Pro Pro Ser His Thr Gly Pro Gln Cys Gln Thr Ser Thr Asp
         755                 760                 765

Tyr Cys Val Ser Ala Pro Cys Phe Asn Gly Gly Thr Cys Val Asn Arg
         770                 775                 780

Pro Gly Thr Phe Ser Cys Leu Cys Ala Met Gly Phe Gln Gly Pro Arg
785                 790                 795                 800

Cys Glu Gly Lys Leu Arg Pro Ser Cys Ala Asp Ser Pro Cys Arg Asn
                 805                 810                 815

Arg Ala Thr Cys Gln Asp Ser Pro Gln Gly Pro Arg Cys Leu Cys Pro

```
                820             825             830
Thr Gly Tyr Thr Gly Gly Ser Cys Gln Thr Leu Met Asp Leu Cys Ala
        835             840             845

Gln Lys Pro Cys Pro Arg Asn Ser His Cys Leu Gln Thr Gly Pro Ser
    850             855             860

Phe His Cys Leu Cys Leu Gln Gly Trp Thr Gly Pro Leu Cys Asn Leu
865             870             875             880

Pro Leu Ser Ser Cys Gln Lys Ala Ala Leu Ser Gln Gly Ile Asp Val
            885             890             895

Ser Ser Leu Cys His Asn Gly Gly Leu Cys Val Asp Ser Gly Pro Ser
        900             905             910

Tyr Phe Cys His Cys Pro Pro Gly Phe Gln Gly Ser Leu Cys Gln Asp
    915             920             925

His Val Asn Pro Cys Glu Ser Arg Pro Cys Gln Asn Gly Ala Thr Cys
930             935             940

Met Ala Gln Pro Ser Gly Tyr Leu Cys Gln Cys Ala Pro Gly Tyr Asp
945             950             955             960

Gly Gln Asn Cys Ser Lys Glu Leu Asp Ala Cys Gln Ser Gln Pro Cys
            965             970             975

His Asn His Gly Thr Cys Thr Pro Lys Pro Gly Gly Phe His Cys Ala
        980             985             990

Cys Pro Pro Gly Phe Val Gly Leu Arg Cys Glu Gly Asp Val Asp Glu
    995             1000            1005

Cys Leu Asp Gln Pro Cys His Pro Thr Gly Thr Ala Ala Cys His
    1010            1015            1020

Ser Leu Ala Asn Ala Phe Tyr Cys Gln Cys Leu Pro Gly His Thr
    1025            1030            1035

Gly Gln Trp Cys Glu Val Glu Ile Asp Pro Cys His Ser Gln Pro
    1040            1045            1050

Cys Phe His Gly Gly Thr Cys Glu Ala Thr Ala Gly Ser Pro Leu
    1055            1060            1065

Gly Phe Ile Cys His Cys Pro Lys Gly Phe Glu Gly Pro Thr Cys
    1070            1075            1080

Ser His Arg Ala Pro Ser Cys Gly Phe His His Cys His His Gly
    1085            1090            1095

Gly Leu Cys Leu Pro Ser Pro Lys Pro Gly Phe Pro Pro Arg Cys
    1100            1105            1110

Ala Cys Leu Ser Gly Tyr Gly Gly Pro Asp Cys Leu Thr Pro Pro
    1115            1120            1125

Ala Pro Lys Gly Cys Gly Pro Pro Ser Pro Cys Leu Tyr Asn Gly
    1130            1135            1140

Ser Cys Ser Glu Thr Thr Gly Leu Gly Gly Pro Gly Phe Arg Cys
    1145            1150            1155

Ser Cys Pro His Ser Ser Pro Gly Pro Arg Cys Gln Lys Pro Gly
    1160            1165            1170

Ala Lys Gly Cys Glu Gly Arg Ser Gly Asp Gly Ala Cys Asp Ala
    1175            1180            1185

Gly Cys Ser Gly Pro Gly Gly Asn Trp Asp Gly Gly Asp Cys Ser
    1190            1195            1200

Leu Gly Val Pro Asp Pro Trp Lys Gly Cys Pro Ser His Ser Arg
    1205            1210            1215

Cys Trp Leu Leu Phe Arg Asp Gly Gln Cys His Pro Gln Cys Asp
    1220            1225            1230
```

-continued

```
Ser Glu Glu Cys Leu Phe Asp Gly Tyr Asp Cys Glu Thr Pro Pro
1235                1240                1245

Ala Cys Thr Pro Ala Tyr Asp Gln Tyr Cys His Asp His Phe His
1250                1255                1260

Asn Gly His Cys Glu Lys Gly Cys Asn Thr Ala Glu Cys Gly Trp
1265                1270                1275

Asp Gly Gly Asp Cys Arg Pro Glu Asp Gly Asp Pro Glu Trp Gly
1280                1285                1290

Pro Ser Leu Ala Leu Leu Val Val Leu Ser Pro Ala Leu Asp
1295                1300                1305

Gln Gln Leu Phe Ala Leu Ala Arg Val Leu Ser Leu Thr Leu Arg
1310                1315                1320

Val Gly Leu Trp Val Arg Lys Asp Arg Asp Gly Arg Asp Met Val
1325                1330                1335

Tyr Pro Tyr Pro Gly Ala Arg Ala Glu Glu Lys Leu Gly Gly Thr
1340                1345                1350

Arg Asp Pro Thr Tyr Gln Glu Arg Ala Ala Pro Gln Thr Gln Pro
1355                1360                1365

Leu Gly Lys Glu Thr Asp Ser Leu Ser Ala Gly Phe Val Val Val
1370                1375                1380

Met Gly Val Asp Leu Ser Arg Cys Gly Pro Asp His Pro Ala Ser
1385                1390                1395

Arg Cys Pro Trp Asp Pro Gly Leu Leu Leu Arg Phe Leu Ala Ala
1400                1405                1410

Met Ala Ala Val Gly Ala Leu Glu Pro Leu Leu Pro Gly Pro Leu
1415                1420                1425

Leu Ala Val His Pro His Ala Gly Thr Ala Pro Pro Ala Asn Gln
1430                1435                1440

Leu Pro Trp Pro Val Leu Cys Ser Pro Val Ala Gly Val Ile Leu
1445                1450                1455

Leu Ala Leu Gly Ala Leu Leu Val Leu Gln Leu Ile Arg Arg Arg
1460                1465                1470

Arg Arg Glu His Gly Ala Leu Trp Leu Pro Pro Gly Phe Thr Arg
1475                1480                1485

Arg Pro Arg Thr Gln Ser Ala Pro His Arg Arg Pro Pro Leu
1490                1495                1500

Gly Glu Asp Ser Ile Gly Leu Lys Ala Leu Lys Pro Lys Ala Glu
1505                1510                1515

Val Asp Glu Asp Gly Val Val Met Cys Ser Gly Pro Glu Glu Gly
1520                1525                1530

Glu Glu Val Gly Gln Ala Glu Glu Thr Gly Pro Pro Ser Thr Cys
1535                1540                1545

Gln Leu Trp Ser Leu Ser Gly Gly Cys Gly Ala Leu Pro Gln Ala
1550                1555                1560

Ala Met Leu Thr Pro Pro Gln Glu Ser Glu Met Glu Ala Pro Asp
1565                1570                1575

Leu Asp Thr Arg Gly Pro Asp Gly Val Thr Pro Leu Met Ser Ala
1580                1585                1590

Val Cys Cys Gly Glu Val Gln Ser Gly Thr Phe Gln Gly Ala Trp
1595                1600                1605

Leu Gly Cys Pro Glu Pro Trp Glu Pro Leu Leu Asp Gly Gly Ala
1610                1615                1620

Cys Pro Gln Ala His Thr Val Gly Thr Gly Glu Thr Pro Leu His
1625                1630                1635
```

```
Leu Ala Ala Arg Phe Ser Arg Pro Thr Ala Ala Arg Arg Leu Leu
        1640            1645                1650

Glu Ala Gly Ala Asn Pro Asn Gln Pro Asp Arg Ala Gly Arg Thr
        1655            1660                1665

Pro Leu His Ala Ala Val Ala Ala Asp Ala Arg Glu Val Cys Gln
        1670            1675                1680

Leu Leu Leu Arg Ser Arg Gln Thr Ala Val Asp Ala Arg Thr Glu
        1685            1690                1695

Asp Gly Thr Thr Pro Leu Met Leu Ala Ala Arg Leu Ala Val Glu
        1700            1705                1710

Asp Leu Val Glu Glu Leu Ile Ala Ala Gln Ala Asp Val Gly Ala
        1715            1720                1725

Arg Asp Lys Trp Gly Lys Thr Ala Leu His Trp Ala Ala Ala Val
        1730            1735                1740

Asn Asn Ala Arg Ala Ala Arg Ser Leu Leu Gln Ala Gly Ala Asp
        1745            1750                1755

Lys Asp Ala Gln Asp Asn Arg Glu Gln Thr Pro Leu Phe Leu Ala
        1760            1765                1770

Ala Arg Glu Gly Ala Val Glu Val Ala Gln Leu Leu Leu Gly Leu
        1775            1780                1785

Gly Ala Ala Arg Glu Leu Arg Asp Gln Ala Gly Leu Ala Pro Ala
        1790            1795                1800

Asp Val Ala His Gln Arg Asn His Trp Asp Leu Leu Thr Leu Leu
        1805            1810                1815

Glu Gly Ala Gly Pro Pro Glu Ala Arg His Lys Ala Thr Pro Gly
        1820            1825                1830

Arg Glu Ala Gly Pro Phe Pro Arg Ala Arg Thr Val Ser Val Ser
        1835            1840                1845

Val Pro Pro His Gly Gly Gly Ala Leu Pro Arg Cys Arg Thr Leu
        1850            1855                1860

Ser Ala Gly Ala Gly Pro Arg Gly Gly Gly Ala Cys Leu Gln Ala
        1865            1870                1875

Arg Thr Trp Ser Val Asp Leu Ala Ala Arg Gly Gly Gly Ala Tyr
        1880            1885                1890

Ser His Cys Arg Ser Leu Ser Gly Val Gly Ala Gly Gly Gly Pro
        1895            1900                1905

Thr Pro Arg Gly Arg Arg Phe Ser Ala Gly Met Arg Gly Pro Arg
        1910            1915                1920

Pro Asn Pro Ala Ile Met Arg Gly Arg Tyr Gly Val Ala Ala Gly
        1925            1930                1935

Arg Gly Gly Arg Val Ser Thr Asp Asp Trp Pro Cys Asp Trp Val
        1940            1945                1950

Ala Leu Gly Ala Cys Gly Ser Ala Ser Asn Ile Pro Ile Pro Pro
        1955            1960                1965

Pro Cys Leu Thr Pro Ser Pro Glu Arg Gly Ser Pro Gln Leu Asp
        1970            1975                1980

Cys Gly Pro Pro Ala Leu Gln Glu Met Pro Ile Asn Gln Gly Gly
        1985            1990                1995

Glu Gly Lys Lys
        2000

<210> SEQ ID NO 5
<211> LENGTH: 48
<212> TYPE: PRT
```

-continued

<213> ORGANISM: Homo sapiens

<400> SEQUENCE: 5

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
            20                  25                  30

Thr Asn Val Val Phe Lys Arg Asp Ala His Gly Gln Gln Met Ile Phe
        35                  40                  45

<210> SEQ ID NO 6
<211> LENGTH: 48
<212> TYPE: PRT
<213> ORGANISM: Rattus rattus

<400> SEQUENCE: 6

Ala Ala Gly Thr Leu Val Leu Val Val Leu Leu Pro Pro Asp Gln Leu
1               5                   10                  15

Arg Asn Asn Ser Phe His Phe Leu Arg Asp Val Ser His Val Leu His
            20                  25                  30

Thr Asn Val Val Phe Lys Arg Asp Ala His Gly Gln Gln Met Ile Phe
        35                  40                  45

<210> SEQ ID NO 7
<211> LENGTH: 48
<212> TYPE: PRT
<213> ORGANISM: Mus musculus

<400> SEQUENCE: 7

Ala Ala Gly Thr Leu Val Leu Val Val Leu Leu Pro Pro Asp Gln Leu
1               5                   10                  15

Arg Asn Asn Ser Phe His Phe Leu Arg Glu Leu Ser His Val Leu His
            20                  25                  30

Thr Asn Val Val Phe Lys Arg Asp Ala His Gly Gln Gln Met Ile Phe
        35                  40                  45

<210> SEQ ID NO 8
<211> LENGTH: 48
<212> TYPE: PRT
<213> ORGANISM: Gallus gallus

<400> SEQUENCE: 8

Ala Asp Gly Thr Leu Val Val Val Val Leu Ile Thr Pro Glu Asn Leu
1               5                   10                  15

Lys Asn Asn Ser Phe Asn Phe Leu Arg Glu Leu Ser Arg Val Leu His
            20                  25                  30

Thr Asn Val Val Phe Lys Lys Asn Ala His Gly Gln Gln Met Ile Phe
        35                  40                  45

<210> SEQ ID NO 9
<211> LENGTH: 48
<212> TYPE: PRT
<213> ORGANISM: Xenopus laevis

<400> SEQUENCE: 9

Ala Glu Gly Thr Leu Val Leu Val Val Leu Met Pro Pro Glu Arg Leu
1               5                   10                  15

Lys Asn Asn Ser Val Asn Phe Leu Arg Glu Leu Ser Arg Val Leu His
            20                  25                  30

Thr Asn Val Val Phe Lys Lys Asp Ala His Gly Gln Gln Met Ile Phe
        35                  40                  45

```
<210> SEQ ID NO 10
<211> LENGTH: 48
<212> TYPE: PRT
<213> ORGANISM: Danio rerio

<400> SEQUENCE: 10

Ala Val Gly Leu Leu Val Val Val His Ile His Pro Asp Gln Leu
 1               5                  10                  15

Arg Asn Asn Ser Phe Gly Phe Leu Arg Glu Leu Ser Arg Val Leu His
                 20                  25                  30

Thr Asn Val Val Phe Arg Arg Asp Ala His Gly Gln Gln Met Ile Phe
                 35                  40                  45

<210> SEQ ID NO 11
<211> LENGTH: 48
<212> TYPE: PRT
<213> ORGANISM: artificial sequence
<220> FEATURE:
<223> OTHER INFORMATION: consensus sequence
<220> FEATURE:
<221> NAME/KEY: misc_feature
<222> LOCATION: (2)..(2)
<223> OTHER INFORMATION: Xaa=Val, Glu, Asp or Ala
<220> FEATURE:
<221> NAME/KEY: misc_feature
<222> LOCATION: (4)..(4)
<223> OTHER INFORMATION: Xaa=Leu or Thr
<220> FEATURE:
<221> NAME/KEY: misc_feature
<222> LOCATION: (7)..(7)
<223> OTHER INFORMATION: Xaa=Val or Leu
<220> FEATURE:
<221> NAME/KEY: misc_feature
<222> LOCATION: (10)..(10)
<223> OTHER INFORMATION: Xaa=His or Leu
<220> FEATURE:
<221> NAME/KEY: misc_feature
<222> LOCATION: (11)..(11)
<223> OTHER INFORMATION: Xaa=Ile, Met or Leu
<220> FEATURE:
<221> NAME/KEY: misc_feature
<222> LOCATION: (12)..(12)
<223> OTHER INFORMATION: Xaa=His, Pro or Thr
<220> FEATURE:
<221> NAME/KEY: misc_feature
<222> LOCATION: (14)..(14)
<223> OTHER INFORMATION: Xaa=Asp or Glu
<220> FEATURE:
<221> NAME/KEY: misc_feature
<222> LOCATION: (15)..(15)
<223> OTHER INFORMATION: Xaa=Gln, Arg or Asn
<220> FEATURE:
<221> NAME/KEY: misc_feature
<222> LOCATION: (17)..(17)
<223> OTHER INFORMATION: Xaa=Arg or Lys
<220> FEATURE:
<221> NAME/KEY: misc_feature
<222> LOCATION: (19)..(19)
<223> OTHER INFORMATION: Xaa=Asn or Ser
<220> FEATURE:
<221> NAME/KEY: misc_feature
<222> LOCATION: (21)..(21)
<223> OTHER INFORMATION: Xaa=Phe or Val
<220> FEATURE:
<221> NAME/KEY: misc_feature
<222> LOCATION: (22)..(22)
<223> OTHER INFORMATION: Xaa=Gly, Asn or His
<220> FEATURE:
<221> NAME/KEY: misc_feature
<222> LOCATION: (26)..(26)
<223> OTHER INFORMATION: Xaa=Asp or Glu
<220> FEATURE:
<221> NAME/KEY: misc_feature
<222> LOCATION: (27)..(27)
```

<223> OTHER INFORMATION: Xaa=Leu or Val
<220> FEATURE:
<221> NAME/KEY: misc_feature
<222> LOCATION: (29)..(29)
<223> OTHER INFORMATION: Xaa=Arg or His
<220> FEATURE:
<221> NAME/KEY: misc_feature
<222> LOCATION: (38)..(38)
<223> OTHER INFORMATION: Xaa=Arg or Lys
<220> FEATURE:
<221> NAME/KEY: misc_feature
<222> LOCATION: (39)..(39)
<223> OTHER INFORMATION: Xaa=Arg or Lys

<400> SEQUENCE: 11

Ala Xaa Gly Xaa Leu Val Xaa Val Val Xaa Xaa Xaa Pro Xaa Xaa Leu
1               5                   10                  15

Xaa Asn Xaa Ser Xaa Xaa Phe Leu Arg Xaa Xaa Ser Xaa Val Leu His
            20                  25                  30

Thr Asn Val Val Phe Xaa Xaa Asp Ala His Gly Gln Gln Met Ile Phe
        35                  40                  45

<210> SEQ ID NO 12
<211> LENGTH: 48
<212> TYPE: PRT
<213> ORGANISM: Homo sapiens

<400> SEQUENCE: 12

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Pro His
            20                  25                  30

Thr Asn Val Val Phe Lys Arg Asp Ala His Gly Gln Gln Met Ile Phe
        35                  40                  45

<210> SEQ ID NO 13
<211> LENGTH: 48
<212> TYPE: PRT
<213> ORGANISM: Homo sapiens

<400> SEQUENCE: 13

Ala Ala Gly Thr Leu Val Val Val Leu Met Pro Pro Glu Gln Leu
1               5                   10                  15

Arg Asn Ser Ser Phe His Phe Pro Arg Glu Leu Ser Arg Val Leu His
            20                  25                  30

Thr Asn Val Val Phe Lys Arg Asp Ala His Gly Gln Gln Met Ile Phe
        35                  40                  45

<210> SEQ ID NO 14
<211> LENGTH: 48
<212> TYPE: PRT
<213> ORGANISM: Homo sapiens

<400> SEQUENCE: 14

Ala Ala Gly Thr Leu Val Val Val Leu Met Pro Pro Glu Gln Leu
1               5                   10                  15

Arg Asn Ser Ser Phe His Phe Pro Arg Glu Leu Ser Arg Val Leu His
            20                  25                  30

Thr Asn Val Val Phe Lys Arg Val Ala His Gly Gln Gln Met Ile Phe
        35                  40                  45

<210> SEQ ID NO 15
<211> LENGTH: 48
<212> TYPE: PRT

<213> ORGANISM: Homo sapiens

<400> SEQUENCE: 15

Ala Ala Gly Thr Leu Val Val Val Leu Met Pro Pro Glu Gln Leu
1               5                   10                  15

Arg Asn Ser Ser Phe His Phe Leu Arg Glu Leu Ser Pro Val Leu His
                20                  25                  30

Thr Asn Val Val Phe Lys Arg Asp Ala His Gly Gln Gln Met Ile Phe
            35                  40                  45

<210> SEQ ID NO 16
<211> LENGTH: 48
<212> TYPE: PRT
<213> ORGANISM: Homo sapiens

<400> SEQUENCE: 16

Ala Ala Gly Thr Pro Val Val Val Leu Met Pro Pro Glu Gln Leu
1               5                   10                  15

Arg Asn Ser Ser Phe His Phe Leu Arg Glu Leu Ser Arg Val Leu His
                20                  25                  30

Thr Asn Val Val Phe Lys Arg Asp Ala His Gly Gln Gln Met Ile Phe
            35                  40                  45

<210> SEQ ID NO 17
<211> LENGTH: 47
<212> TYPE: PRT
<213> ORGANISM: Homo sapiens

<400> SEQUENCE: 17

Ala Ala Gly Thr Leu Val Val Val Leu Met Pro Pro Glu Gln Leu Arg
1               5                   10                  15

Asn Ser Ser Phe His Phe Leu Arg Glu Leu Ser Arg Val Leu His Thr
                20                  25                  30

Asn Val Val Phe Lys Arg Asp Ala His Gly Gln Gln Met Ile Phe
            35                  40                  45

<210> SEQ ID NO 18
<211> LENGTH: 48
<212> TYPE: PRT
<213> ORGANISM: Homo sapiens

<400> SEQUENCE: 18

Ala Ala Gly Thr Leu Val Val Val Leu Met Pro Pro Glu Gln Leu
1               5                   10                  15

Arg Asn Ser Ser Phe His Ser Leu Arg Glu Leu Ser Arg Val Leu His
                20                  25                  30

Thr Asn Val Val Phe Lys Arg Asp Ala His Gly Gln Gln Met Ile Phe
            35                  40                  45

<210> SEQ ID NO 19
<211> LENGTH: 48
<212> TYPE: PRT
<213> ORGANISM: Homo sapiens

<400> SEQUENCE: 19

Ala Ala Gly Thr Leu Val Val Val Leu Met Pro Pro Glu Gln Pro
1               5                   10                  15

Arg Asn Ser Ser Phe His Phe Leu Arg Glu Leu Ser Arg Val Leu His
                20                  25                  30

Thr Asn Val Val Phe Lys Arg Asp Ala His Gly Gln Gln Met Ile Phe
            35                  40                  45

<210> SEQ ID NO 20
<211> LENGTH: 48
<212> TYPE: PRT
<213> ORGANISM: Homo sapiens

<400> SEQUENCE: 20

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
            20                  25                  30

Thr Asn Val Val Phe Lys Ser Asp Ala His Gly Gln Gln Met Ile Phe
        35                  40                  45

<210> SEQ ID NO 21
<211> LENGTH: 47
<212> TYPE: PRT
<213> ORGANISM: Homo sapiens

<400> SEQUENCE: 21

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
            20                  25                  30

Thr Asn Val Phe Lys Arg Asp Ala His Gly Gln Gln Met Ile Phe
        35                  40                  45

<210> SEQ ID NO 22
<211> LENGTH: 46
<212> TYPE: PRT
<213> ORGANISM: Homo sapiens

<400> SEQUENCE: 22

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
            20                  25                  30

Thr Asn Val Val Phe Lys Thr His Gly Gln Gln Met Ile Phe
        35                  40                  45

<210> SEQ ID NO 23
<211> LENGTH: 53
<212> TYPE: PRT
<213> ORGANISM: Homo sapiens

<400> SEQUENCE: 23

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
            20                  25                  30

Thr Asn Val Val Phe Lys Arg Asp Ala His Gly Gln Gln Met Ile Phe
        35                  40                  45

Pro Pro Gly Gly Gly
        50

<210> SEQ ID NO 24
<211> LENGTH: 53
<212> TYPE: PRT
<213> ORGANISM: Homo sapiens

<400> SEQUENCE: 24

Ala Ala Gly Thr Leu Val Val Val Leu Met Pro Pro Ala Gln Gln
1               5                   10                  15

Leu Arg Asn Ser Ser Phe His Phe Leu Arg Glu Leu Ser Arg Val Leu
            20                  25                  30

His Thr Asn Val Val Phe Lys Arg Asp Ala His Gly Gln Gln Met Ile
        35                  40                  45

Phe Pro Tyr Tyr Gly
    50

<210> SEQ ID NO 25
<211> LENGTH: 53
<212> TYPE: PRT
<213> ORGANISM: Homo sapiens

<400> SEQUENCE: 25

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
            20                  25                  30

Thr Asn Val Val Leu Gly Arg Arg Asp Ala His Gly Gln Gln Met Ile
        35                  40                  45

Phe Pro Tyr Tyr Gly
    50

<210> SEQ ID NO 26
<211> LENGTH: 53
<212> TYPE: PRT
<213> ORGANISM: Homo sapiens

<400> SEQUENCE: 26

Ala Ala Gly Thr Leu Val Val Val Leu Met Pro Pro Glu Gln Leu
1               5                   10                  15

Arg Asn Ser Ser Phe His Leu Ala Leu Arg Glu Leu Ser Arg Val Leu
            20                  25                  30

His Thr Asn Val Val Phe Lys Arg Asp Ala His Gly Gln Gln Met Ile
        35                  40                  45

Phe Pro Tyr Tyr Gly
    50

<210> SEQ ID NO 27
<211> LENGTH: 55
<212> TYPE: PRT
<213> ORGANISM: Homo sapiens

<400> SEQUENCE: 27

Ala Ala Gly Thr Leu Val Val Val Leu Met Pro Pro Glu Gln Leu
1               5                   10                  15

Arg Asn Ser Ser Phe His Phe Leu Arg Glu Lys Glu Asp Leu Ser Arg
            20                  25                  30

Val Leu His Thr Asn Val Val Phe Lys Arg Asp Ala His Gly Gln Gln
        35                  40                  45

Met Ile Phe Pro Tyr Tyr Gly
    50                  55

<210> SEQ ID NO 28
<211> LENGTH: 56
<212> TYPE: PRT
<213> ORGANISM: Homo sapiens

<400> SEQUENCE: 28

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
                20                  25                  30

Thr Asn Val Val Phe Lys Ser Met Pro Pro Arg Asp Ala His Gly Gln
            35                  40                  45

Gln Met Ile Phe Pro Tyr Tyr Gly
    50                  55

<210> SEQ ID NO 29
<211> LENGTH: 53
<212> TYPE: PRT
<213> ORGANISM: Homo sapiens

<400> SEQUENCE: 29

Ala Ala Gly Thr Leu Val Val Val Leu Met Pro Pro Glu Gln Leu
1               5                   10                  15

Arg Asn Ser Ser Phe His Thr Ala Leu Arg Glu Leu Ser Arg Val Leu
                20                  25                  30

His Thr Asn Val Val Phe Lys Arg Asp Ala His Gly Gln Gln Met Ile
            35                  40                  45

Phe Pro Tyr Tyr Gly
    50

<210> SEQ ID NO 30
<211> LENGTH: 88
<212> TYPE: PRT
<213> ORGANISM: Homo sapiens

<400> SEQUENCE: 30

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
                20                  25                  30

Leu Gln His Gly Met Val Gly Pro Leu His Ser Ser Leu Ala Ala Ser
            35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu
                85

<210> SEQ ID NO 31
<211> LENGTH: 84
<212> TYPE: PRT
<213> ORGANISM: Homo sapiens

<400> SEQUENCE: 31

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
                20                  25                  30

Leu Gln His Gly Met Val Gly Pro Leu His Ser Ser Leu Ala Ala Ser
            35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln

<210> SEQ ID NO 32
<211> LENGTH: 83
<212> TYPE: PRT
<213> ORGANISM: Homo sapiens

<400> SEQUENCE: 32

```
Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
50                  55                  60

Ala Thr Gln Pro His Leu Val Gln Thr Gln Gln Val Gln Pro Gln Asn
65                  70                  75                  80

Leu Gln Met
```

<210> SEQ ID NO 33
<211> LENGTH: 31
<212> TYPE: PRT
<213> ORGANISM: Homo sapiens

<400> SEQUENCE: 33

```
Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro
            20                  25                  30
```

<210> SEQ ID NO 34
<211> LENGTH: 166
<212> TYPE: PRT
<213> ORGANISM: Homo sapiens

<400> SEQUENCE: 34

```
Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
50                  55                  60

Ala Thr Gln Pro His Leu Val Gln Thr Gln Gln Val Gln Pro Gln Asn
65                  70                  75                  80

Leu Gln Met Gln Gln Asn Leu Gln Pro Ala Asn Ile Gln Gln
                85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
        115                 120                 125

Pro Ser Gln Ala Asp Val Gln Pro Leu Gly Pro Ser Ser Leu Ala Val
130                 135                 140

His Thr Ile Leu Pro Gln Glu Ser Pro Ala Leu Pro Thr Ser Leu Pro
145                 150                 155                 160
```

```
Ser Ser Leu Val Pro Pro
                165

<210> SEQ ID NO 35
<211> LENGTH: 167
<212> TYPE: PRT
<213> ORGANISM: Homo sapiens

<400> SEQUENCE: 35

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
        115                 120                 125

Pro Ser Gln Ala Asp Val Gln Pro Leu Gly Pro Ser Ser Leu Ala Val
    130                 135                 140

His Thr Ile Leu Pro Gln Glu Ser Pro Ala Leu Pro Thr Ser Leu Pro
145                 150                 155                 160

Ser Ser Leu Val Ala His Pro
                165

<210> SEQ ID NO 36
<211> LENGTH: 167
<212> TYPE: PRT
<213> ORGANISM: Homo sapiens

<400> SEQUENCE: 36

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
        115                 120                 125

Pro Ser Gln Ala Asp Val Gln Pro Leu Gly Pro Ser Ser Leu Ala Val
    130                 135                 140

His Thr Ile Leu Pro Gln Glu Ser Pro Ala Leu Pro Thr Ser Gly Cys
```

```
                145                 150                 155                 160
His Pro Arg Trp Ser His Pro
                165

<210> SEQ ID NO 37
<211> LENGTH: 156
<212> TYPE: PRT
<213> ORGANISM: Homo sapiens

<400> SEQUENCE: 37

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Gln Pro His Leu Gly Val
            100                 105                 110

Ser Ser Ala Ala Ser Gly His Leu Gly Arg Ser Phe Leu Ser Gly Glu
        115                 120                 125

Pro Ser Gln Ala Asp Val Gln Pro Leu Gly Pro Ser Ser Leu Ala Val
    130                 135                 140

His Thr Ile Leu Pro Gln Glu Ser Pro Ala Leu Pro
145                 150                 155

<210> SEQ ID NO 38
<211> LENGTH: 166
<212> TYPE: PRT
<213> ORGANISM: Homo sapiens

<400> SEQUENCE: 38

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Gln Pro His Leu Gly Val
            100                 105                 110

Ser Ser Ala Ala Ser Gly His Leu Gly Arg Ser Phe Leu Ser Gly Glu
        115                 120                 125

Pro Ser Gln Ala Asp Val Gln Pro Leu Gly Pro Ser Ser Leu Ala Val
    130                 135                 140

His Thr Ile Leu Pro Gln Glu Ser Pro Pro Cys Pro Arg Arg Cys His
145                 150                 155                 160
```

```
Pro Arg Trp Ser His Pro
            165

<210> SEQ ID NO 39
<211> LENGTH: 150
<212> TYPE: PRT
<213> ORGANISM: Homo sapiens

<400> SEQUENCE: 39

Trp Leu Ser Arg Leu Gln Ser Gly Met Val Pro Asn Gln Tyr Asn Pro
1               5                  10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
        115                 120                 125

Pro Ser Gln Ala Asp Val Gln Pro Leu Gly Pro Ser Ser Leu Ala Val
    130                 135                 140

His Thr Ile Leu Pro Gln
145                 150

<210> SEQ ID NO 40
<211> LENGTH: 170
<212> TYPE: PRT
<213> ORGANISM: Homo sapiens

<400> SEQUENCE: 40

Trp Leu Ser Arg Leu Gln Ser Gly Met Val Pro Asn Gln Tyr Asn Pro
1               5                  10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
        115                 120                 125

Pro Ser Gln Ala Asp Leu Ser Arg Asp Leu Cys Ser His Trp Ala Pro
    130                 135                 140

Ala Ala Trp Arg Cys Thr Leu Phe Cys Pro Arg Arg Ala Pro Pro Cys
145                 150                 155                 160
```

Pro Arg Arg Cys His Pro Arg Trp Ser His
                165                 170

<210> SEQ ID NO 41
<211> LENGTH: 167
<212> TYPE: PRT
<213> ORGANISM: Homo sapiens

<400> SEQUENCE: 41

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
        115                 120                 125

Pro Ser Gln Ala Asp Cys Cys Ser His Trp Ala Pro Ala Ala Trp Arg
    130                 135                 140

Cys Thr Leu Phe Cys Pro Arg Arg Ala Pro Pro Cys Pro Arg Arg Cys
145                 150                 155                 160

His Pro Arg Trp Ser His Pro
                165

<210> SEQ ID NO 42
<211> LENGTH: 170
<212> TYPE: PRT
<213> ORGANISM: Homo sapiens

<400> SEQUENCE: 42

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
        115                 120                 125

Pro Ser Gln Ala Glu Gly Arg Gly Arg Cys Ser His Trp Ala Pro Ala
    130                 135                 140

Ala Trp Arg Cys Thr Leu Phe Cys Pro Arg Arg Ala Pro Pro Cys Pro

```
                145                 150                 155                 160
Arg Arg Cys His Pro Arg Trp Ser His Pro
                165                 170

<210> SEQ ID NO 43
<211> LENGTH: 169
<212> TYPE: PRT
<213> ORGANISM: Homo sapiens

<400> SEQUENCE: 43

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
                20                  25                  30

Leu Gln His Gly Met Val Gly Pro Leu His Ser Ser Leu Ala Ala Ser
            35                  40                  45

Ala Leu Ser Gln Met Met Ser Tyr Gln Gly Leu Pro Ser Thr Arg Leu
        50                  55                  60

Ala Thr Gln Pro His Leu Val Gln Thr Gln Gln Val Gln Pro Gln Asn
65                  70                  75                  80

Leu Gln Met Gln Gln Asn Leu Gln Pro Ala Asn Ile Gln Gln Gln
                85                  90                  95

Gln Ser Leu Gln Pro Pro Pro Pro Pro Gln Pro His Leu Gly Val
                100                 105                 110

Ser Ser Ala Ala Ser Gly His Leu Gly Arg Ser Phe Leu Ser Gly Glu
            115                 120                 125

Pro Ser Gln Gly Gly Gly Met Gly Ser His Trp Ala Pro Ala Ala
        130                 135                 140

Trp Arg Cys Thr Leu Phe Cys Pro Arg Ala Pro Pro Cys Pro Arg
145                 150                 155                 160

Arg Cys His Pro Arg Trp Ser His Pro
                165

<210> SEQ ID NO 44
<211> LENGTH: 167
<212> TYPE: PRT
<213> ORGANISM: Homo sapiens

<400> SEQUENCE: 44

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
                20                  25                  30

Leu Gln His Gly Met Val Gly Pro Leu His Ser Ser Leu Ala Ala Ser
            35                  40                  45

Ala Leu Ser Gln Met Met Ser Tyr Gln Gly Leu Pro Ser Thr Arg Leu
        50                  55                  60

Ala Thr Gln Pro His Leu Val Gln Thr Gln Gln Val Gln Pro Gln Asn
65                  70                  75                  80

Leu Gln Met Gln Gln Asn Leu Gln Pro Ala Asn Ile Gln Gln Gln
                85                  90                  95

Gln Ser Leu Gln Pro Pro Pro Pro Pro Gln Pro His Leu Gly Val
                100                 105                 110

Ser Ser Ala Ala Ser Gly His Leu Gly Arg Ser Phe Leu Ser Gly Glu
            115                 120                 125

Glu Arg Ala Arg Gln Thr Cys Ser His Trp Ala Pro Ala Ala Trp Arg
        130                 135                 140
```

Cys Thr Leu Phe Cys Pro Arg Arg Ala Pro Pro Cys Pro Arg Arg Cys
145                 150                 155                 160

His Pro Arg Trp Ser His Pro
                165

<210> SEQ ID NO 45
<211> LENGTH: 168
<212> TYPE: PRT
<213> ORGANISM: Homo sapiens

<400> SEQUENCE: 45

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
                20                  25                  30

Leu Gln His Gly Met Val Gly Pro Leu His Ser Ser Leu Ala Ala Ser
            35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Pro Gln Pro His Leu Gly Val
                100                 105                 110

Ser Ser Ala Ala Ser Gly His Leu Gly Arg Ser Phe Leu Ser Gly Glu
            115                 120                 125

Arg Val Arg Ala Arg Gln Thr Cys Ser His Trp Ala Pro Ala Ala Trp
130                 135                 140

Arg Cys Thr Leu Phe Cys Pro Arg Arg Ala Pro Pro Cys Pro Arg Arg
145                 150                 155                 160

Cys His Pro Arg Trp Ser His Pro
                165

<210> SEQ ID NO 46
<211> LENGTH: 128
<212> TYPE: PRT
<213> ORGANISM: Homo sapiens

<400> SEQUENCE: 46

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
                20                  25                  30

Leu Gln His Gly Met Val Gly Pro Leu His Ser Ser Leu Ala Ala Ser
            35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Pro Gln Pro His Leu Gly Val
                100                 105                 110

Ser Ser Ala Ala Ser Gly His Leu Gly Arg Ser Phe Leu Ser Gly Glu
            115                 120                 125

```
<210> SEQ ID NO 47
<211> LENGTH: 126
<212> TYPE: PRT
<213> ORGANISM: Homo sapiens

<400> SEQUENCE: 47

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Ala Pro Ser
            115                 120                 125

<210> SEQ ID NO 48
<211> LENGTH: 112
<212> TYPE: PRT
<213> ORGANISM: Homo sapiens

<400> SEQUENCE: 48

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Pro Gln Pro His Leu Ala Ala
            100                 105                 110

<210> SEQ ID NO 49
<211> LENGTH: 113
<212> TYPE: PRT
<213> ORGANISM: Homo sapiens

<400> SEQUENCE: 49

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60
```

```
Ala Thr Gln Pro His Leu Val Gln Thr Gln Gln Val Gln Pro Gln Asn
 65                  70                  75                  80

Leu Gln Met Gln Gln Gln Asn Leu Gln Pro Ala Asn Ile Gln Gln Gln
                 85                  90                  95

Gln Ser Leu Gln Pro Arg His His His His Ser Arg Thr Leu Val
            100                 105                 110

Ala
```

<210> SEQ ID NO 50
<211> LENGTH: 96
<212> TYPE: PRT
<213> ORGANISM: Homo sapiens

<400> SEQUENCE: 50

```
Trp Leu Ser Arg Leu Gln Ser Gly Met Val Pro Asn Gln Tyr Asn Pro
 1               5                  10                  15

Leu Arg Gly Ser Val Ala Pro Gly Pro Leu Ser Thr Gln Ala Pro Ser
                20                  25                  30

Leu Gln His Gly Met Val Gly Pro Leu His Ser Ser Leu Ala Ala Ser
            35                  40                  45

Ala Leu Ser Gln Met Met Ser Tyr Gln Gly Leu Pro Ser Thr Arg Leu
        50                  55                  60

Ala Thr Gln Pro His Leu Val Gln Thr Gln Gln Val Gln Pro Gln Asn
 65                  70                  75                  80

Leu Gln Met Gln Gln Gln Asn Leu Gln Pro Ala Asn Ile Gln Gln Gln
                 85                  90                  95
```

<210> SEQ ID NO 51
<211> LENGTH: 93
<212> TYPE: PRT
<213> ORGANISM: Homo sapiens

<400> SEQUENCE: 51

```
Trp Leu Ser Arg Leu Gln Ser Gly Met Val Pro Asn Gln Tyr Asn Pro
 1               5                  10                  15

Leu Arg Gly Ser Val Ala Pro Gly Pro Leu Ser Thr Gln Ala Pro Ser
                20                  25                  30

Leu Gln His Gly Met Val Gly Pro Leu His Ser Ser Leu Ala Ala Ser
            35                  40                  45

Ala Leu Ser Gln Met Met Ser Tyr Gln Gly Leu Pro Ser Thr Arg Leu
        50                  55                  60

Ala Thr Gln Pro His Leu Val Gln Thr Gln Gln Val Gln Pro Gln Asn
 65                  70                  75                  80

Leu Gln Met Gln Gln Gln Asn Leu Gln Pro Ala Asn Ile
                 85                  90
```

<210> SEQ ID NO 52
<211> LENGTH: 275
<212> TYPE: PRT
<213> ORGANISM: Homo sapiens

<400> SEQUENCE: 52

```
Trp Leu Ser Arg Leu Gln Ser Gly Met Val Pro Asn Gln Tyr Asn Pro
 1               5                  10                  15

Leu Arg Gly Ser Val Ala Pro Gly Pro Leu Ser Thr Gln Ala Pro Ser
                20                  25                  30

Leu Gln His Gly Met Val Gly Pro Leu His Ser Ser Leu Ala Ala Ser
            35                  40                  45
```

```
Ala Leu Ser Gln Met Met Ser Tyr Gln Gly Leu Pro Ser Thr Arg Leu
 50                  55                  60

Ala Thr Gln Pro His Leu Val Gln Thr Gln Gln Val Gln Pro Gln Asn
 65                  70                  75                  80

Leu Gln Met Gln Gln Gln Asn Leu Gln Pro Ala Asn Ile Gln Gln Gln
                 85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
            115                 120                 125

Pro Ser Gln Ala Asp Val Gln Pro Leu Gly Pro Ser Ser Leu Ala Val
            130                 135                 140

His Thr Ile Leu Pro Gln Glu Ser Pro Ala Leu Pro Thr Ser Leu Pro
145                 150                 155                 160

Ser Ser Leu Val Pro Val Thr Ala Ala Gln Phe Leu Thr Pro Pro
            165                 170                 175

Ser Gln His Ser Tyr Ser Ser Pro Val Asp Asn Thr Pro Ser His Gln
            180                 185                 190

Leu Gln Val Pro Glu His Pro Phe Leu Thr Pro Ser Pro Asp Ser Gly
            195                 200                 205

Pro Ala Arg Pro Arg Ile Pro Thr Ser Pro Thr Gly Pro Arg Ala Ser
210                 215                 220

Pro Ala Leu Pro Pro Ala Cys Ser Pro Arg Ser Pro Ala Phe Arg Arg
225                 230                 235                 240

Pro Ser Ser Lys Arg Arg Ala Pro Arg Asp Pro Gly Phe Leu Ser Gln
                245                 250                 255

Ala Phe Gly Arg Leu Cys Ala Leu Cys Gly Cys Gln Gly Arg Pro Glu
            260                 265                 270

Glu Pro Phe
        275

<210> SEQ ID NO 53
<211> LENGTH: 207
<212> TYPE: PRT
<213> ORGANISM: Homo sapiens

<400> SEQUENCE: 53

Trp Leu Ser Arg Leu Gln Ser Gly Met Val Pro Asn Gln Tyr Asn Pro
 1                   5                  10                  15

Leu Arg Gly Ser Val Ala Pro Gly Pro Leu Ser Thr Gln Ala Pro Ser
                 20                  25                  30

Leu Gln His Gly Met Val Gly Pro Leu His Ser Ser Leu Ala Ala Ser
             35                  40                  45

Ala Leu Ser Gln Met Met Ser Tyr Gln Gly Leu Pro Ser Thr Arg Leu
 50                  55                  60

Ala Thr Gln Pro His Leu Val Gln Thr Gln Gln Val Gln Pro Gln Asn
 65                  70                  75                  80

Leu Gln Met Gln Gln Gln Asn Leu Gln Pro Ala Asn Ile Gln Gln Gln
                 85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
            115                 120                 125

Pro Ser Gln Ala Asp Val Gln Pro Leu Gly Pro Ser Ser Leu Ala Val
            130                 135                 140
```

```
His Thr Ile Leu Pro Gln Glu Ser Pro Ala Leu Pro Thr Ser Leu Pro
145                 150                 155                 160

Ser Ser Leu Val Pro Pro Val Thr Ala Ala Gln Phe Leu Thr Pro Pro
                165                 170                 175

Ser Gln His Ser Tyr Ser Ser Pro Val Asp Asn Thr Pro Ser His Gln
            180                 185                 190

Leu Gln Val Pro Glu His Pro Phe Leu Thr Pro Ser Ser Val Pro
        195                 200                 205
```

<210> SEQ ID NO 54
<211> LENGTH: 207
<212> TYPE: PRT
<213> ORGANISM: Homo sapiens

<400> SEQUENCE: 54

```
Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
50                  55                  60

Ala Thr Gln Pro His Leu Val Gln Thr Gln Gln Val Gln Pro Gln Asn
65                  70                  75                  80

Leu Gln Met Gln Gln Asn Leu Gln Pro Ala Asn Ile Gln Gln Gln
                85                  90                  95

Gln Ser Leu Gln Pro Pro Pro Pro Gln Pro His Leu Gly Val
            100                 105                 110

Ser Ser Ala Ala Ser Gly His Leu Gly Arg Ser Phe Leu Ser Gly Glu
            115                 120                 125

Pro Ser Gln Ala Asp Val Gln Pro Leu Gly Pro Ser Ser Leu Ala Val
        130                 135                 140

His Thr Ile Leu Pro Gln Glu Ser Pro Ala Leu Pro Thr Ser Leu Pro
145                 150                 155                 160

Ser Ser Leu Val Pro Pro Val Thr Ala Ala Gln Phe Leu Thr Pro Pro
                165                 170                 175

Ser Gln His Ser Tyr Ser Ser Pro Val Asp Asn Thr Pro Ser His Gln
            180                 185                 190

Leu Gln Val Pro Glu His Pro Phe Leu Thr Pro Ser Arg Val Pro
        195                 200                 205
```

<210> SEQ ID NO 55
<211> LENGTH: 205
<212> TYPE: PRT
<213> ORGANISM: Homo sapiens

<400> SEQUENCE: 55

```
Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
50                  55                  60
```

```
Ala Thr Gln Pro His Leu Val Gln Thr Gln Gln Val Gln Pro Gln Asn
 65                  70                  75                  80

Leu Gln Met Gln Gln Gln Asn Leu Gln Pro Ala Asn Ile Gln Gln Gln
                 85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
            115                 120                 125

Pro Ser Gln Ala Asp Val Gln Pro Leu Gly Pro Ser Ser Leu Ala Val
            130                 135                 140

His Thr Ile Leu Pro Gln Glu Ser Pro Ala Leu Pro Thr Ser Leu Pro
145                 150                 155                 160

Ser Ser Leu Val Pro Pro Val Thr Ala Ala Gln Phe Leu Thr Pro Pro
                165                 170                 175

Ser Gln His Ser Tyr Ser Ser Pro Val Asp Asn Thr Pro Ser His Gln
                180                 185                 190

Leu Gln Val Pro Glu His Pro Phe Leu Thr Pro Val Pro
                195                 200                 205

<210> SEQ ID NO 56
<211> LENGTH: 199
<212> TYPE: PRT
<213> ORGANISM: Homo sapiens

<400> SEQUENCE: 56

Trp Leu Ser Arg Leu Gln Ser Gly Met Val Pro Asn Gln Tyr Asn Pro
  1               5                  10                  15

Leu Arg Gly Ser Val Ala Pro Gly Pro Leu Ser Thr Gln Ala Pro Ser
                 20                  25                  30

Leu Gln His Gly Met Val Gly Pro Leu His Ser Ser Leu Ala Ala Ser
             35                  40                  45

Ala Leu Ser Gln Met Met Ser Tyr Gln Gly Leu Pro Ser Thr Arg Leu
 50                  55                  60

Ala Thr Gln Pro His Leu Val Gln Thr Gln Gln Val Gln Pro Gln Asn
 65                  70                  75                  80

Leu Gln Met Gln Gln Gln Asn Leu Gln Pro Ala Asn Ile Gln Gln Gln
                 85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
            115                 120                 125

Pro Ser Gln Ala Asp Val Gln Pro Leu Gly Pro Ser Ser Leu Ala Val
            130                 135                 140

His Thr Ile Leu Pro Gln Glu Ser Pro Ala Leu Pro Thr Ser Leu Pro
145                 150                 155                 160

Ser Ser Leu Val Pro Pro Val Thr Ala Ala Gln Phe Leu Thr Pro Pro
                165                 170                 175

Ser Gln His Ser Tyr Ser Ser Pro Val Asp Asn Thr Pro Ser His Gln
                180                 185                 190

Leu Gln Val Pro Glu Tyr Pro
                195

<210> SEQ ID NO 57
<211> LENGTH: 196
<212> TYPE: PRT
<213> ORGANISM: Homo sapiens
```

```
<400> SEQUENCE: 57

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Asn Leu Gln Pro Ala Asn Ile Gln Gln Gln
                85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
        115                 120                 125

Pro Ser Gln Ala Asp Val Gln Pro Leu Gly Pro Ser Ser Leu Ala Val
    130                 135                 140

His Thr Ile Leu Pro Gln Glu Ser Pro Ala Leu Pro Thr Ser Leu Pro
145                 150                 155                 160

Ser Ser Leu Val Pro Pro Val Thr Ala Ala Gln Phe Leu Thr Pro Pro
                165                 170                 175

Ser Gln His Ser Tyr Ser Ser Pro Val Asp Asn Thr Pro Ser His Gln
            180                 185                 190

Leu Gln Val Pro
        195

<210> SEQ ID NO 58
<211> LENGTH: 195
<212> TYPE: PRT
<213> ORGANISM: Homo sapiens

<400> SEQUENCE: 58

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Asn Leu Gln Pro Ala Asn Ile Gln Gln Gln
                85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
        115                 120                 125

Pro Ser Gln Ala Asp Val Gln Pro Leu Gly Pro Ser Ser Leu Ala Val
    130                 135                 140

His Thr Ile Leu Pro Gln Glu Ser Pro Ala Leu Pro Thr Ser Leu Pro
145                 150                 155                 160

Ser Ser Leu Val Pro Pro Val Thr Ala Ala Gln Phe Leu Thr Pro Pro
```

```
                    165                 170                 175

Ser Gln His Ser Tyr Ser Ser Gly Arg Gln His Pro Gln Pro Pro Ala
            180                 185                 190

Thr Gly Ala
        195

<210> SEQ ID NO 59
<211> LENGTH: 182
<212> TYPE: PRT
<213> ORGANISM: Homo sapiens

<400> SEQUENCE: 59

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Gln Pro His Leu Gly Val
            100                 105                 110

Ser Ser Ala Ala Ser Gly His Leu Gly Arg Ser Phe Leu Ser Gly Glu
        115                 120                 125

Pro Ser Gln Ala Asp Val Gln Pro Leu Gly Pro Ser Ser Leu Ala Val
    130                 135                 140

His Thr Ile Leu Pro Gln Glu Ser Pro Ala Leu Pro Thr Ser Leu Pro
145                 150                 155                 160

Ser Ser Leu Val Pro Pro Val Thr Ala Ala Gln Phe Leu Thr Pro Pro
                165                 170                 175

Ser Gln His Ser Tyr Ser
            180

<210> SEQ ID NO 60
<211> LENGTH: 66
<212> TYPE: PRT
<213> ORGANISM: Homo sapiens

<400> SEQUENCE: 60

Tyr Ser Ser Pro Val Asp Asn Thr Pro Ser His Gln Leu Gln Val Pro
1               5                   10                  15

Glu His Pro Phe Leu Thr Pro Ser Pro Glu Ser Pro Asp Gln Trp Ser
            20                  25                  30

Ser Ser Ser Pro His Ser Asn Val Ser Asp Trp Ser Glu Gly Val Ser
        35                  40                  45

Ser Pro Pro Thr Ser Met Gln Ser Gln Ile Ala Arg Ile Pro Glu Ala
    50                  55                  60

Phe Lys
65

<210> SEQ ID NO 61
<211> LENGTH: 57
<212> TYPE: PRT
<213> ORGANISM: Danio rerio
```

```
<400> SEQUENCE: 61

Gly Ser Ile Val Tyr Leu Glu Ile Asp Asn Arg Leu Cys Ser Gln Gly
1               5                   10                  15

Ser Asp Asp Cys Phe Arg Asn Ala Asp Ser Ala Ala Glu Tyr Leu Gly
            20                  25                  30

Ala Leu Ser Ala Arg Glu Met Leu Arg Phe Pro Tyr Pro Ile Lys Glu
        35                  40                  45

Val Thr Ser Glu Lys Arg Glu Pro Ser
    50                  55

<210> SEQ ID NO 62
<211> LENGTH: 59
<212> TYPE: PRT
<213> ORGANISM: Homo sapiens

<400> SEQUENCE: 62

Gly Ser Val Val Met Leu Glu Ile Asp Asn Arg Leu Cys Leu Gln Ser
1               5                   10                  15

Ala Glu Asn Asp His Cys Phe Pro Asp Ala Gln Ser Ala Ala Asp Tyr
            20                  25                  30

Leu Gly Ala Leu Ser Ala Val Glu Arg Leu Asp Phe Pro Tyr Pro Leu
        35                  40                  45

Arg Asp Val Arg Gly Glu Pro Leu Glu Ala Pro
    50                  55

<210> SEQ ID NO 63
<211> LENGTH: 57
<212> TYPE: PRT
<213> ORGANISM: Mus musculus

<400> SEQUENCE: 63

Gly Ser Ile Val Tyr Leu Glu Ile Asp Asn Arg Gln Cys Val Gln Ser
1               5                   10                  15

Ser Ser Gln Cys Phe Gln Ser Ala Thr Asp Val Ala Ala Phe Leu Gly
            20                  25                  30

Ala Leu Ala Ser Leu Gly Ser Leu Asn Ile Pro Tyr Lys Ile Glu Ala
        35                  40                  45

Val Lys Ser Glu Pro Val Glu Pro Pro
    50                  55

<210> SEQ ID NO 64
<211> LENGTH: 57
<212> TYPE: PRT
<213> ORGANISM: Rattus rattus

<400> SEQUENCE: 64

Gly Ser Ile Val Tyr Leu Glu Ile Asp Asn Arg Gln Cys Val Gln Ser
1               5                   10                  15

Ser Ser Gln Cys Phe Gln Ser Ala Thr Asp Val Ala Ala Phe Leu Gly
            20                  25                  30

Ala Leu Ala Ser Leu Gly Ser Leu Asn Ile Pro Tyr Lys Ile Glu Ala
        35                  40                  45

Val Lys Ser Glu Thr Val Glu Pro Pro
    50                  55

<210> SEQ ID NO 65
<211> LENGTH: 57
<212> TYPE: PRT
<213> ORGANISM: Homo sapiens
```

<400> SEQUENCE: 65

Gly Ser Ile Val Tyr Leu Glu Ile Asp Asn Arg Gln Cys Val Gln Ala
1               5                   10                  15

Ser Ser Gln Cys Phe Gln Ser Ala Thr Asp Val Ala Ala Phe Leu Gly
            20                  25                  30

Ala Leu Ala Ser Leu Gly Ser Leu Asn Ile Pro Tyr Lys Ile Glu Ala
        35                  40                  45

Val Gln Ser Glu Thr Val Glu Pro Pro
    50                  55

<210> SEQ ID NO 66
<211> LENGTH: 57
<212> TYPE: PRT
<213> ORGANISM: Gallus gallus

<400> SEQUENCE: 66

Gly Ser Ile Val Tyr Leu Glu Ile Asp Asn Arg Gln Cys Ile Gln Ser
1               5                   10                  15

Ser Ser Gln Cys Phe Gln Ser Ala Thr Asp Val Ala Ala Phe Leu Gly
            20                  25                  30

Ala Leu Ala Ser Leu Gly Asn Leu Asn Ile Pro Tyr Lys Ile Glu Ala
        35                  40                  45

Val Lys Ser Glu Thr Ala Glu Pro Ala
    50                  55

<210> SEQ ID NO 67
<211> LENGTH: 58
<212> TYPE: PRT
<213> ORGANISM: Xenopus laevis

<400> SEQUENCE: 67

Gly Ser Ile Val Tyr Leu Glu Ile Asp Asn Arg Gln Cys Tyr Lys Ser
1               5                   10                  15

Ser Ser Gln Cys Phe Asn Ser Ala Thr Asp Val Ala Ala Phe Leu Gly
            20                  25                  30

Ala Leu Ala Ser Leu Gly Ser Leu Asp Thr Leu Ser Tyr Lys Ile Glu
        35                  40                  45

Ala Val Lys Ser Glu Asn Met Glu Thr Pro
    50                  55

<210> SEQ ID NO 68
<211> LENGTH: 55
<212> TYPE: PRT
<213> ORGANISM: Homo sapiens

<400> SEQUENCE: 68

Gly Ser Lys Val Phe Leu Glu Ile Asp Asn Arg Gln Cys Val Gln Asp
1               5                   10                  15

Ser Asp His Cys Phe Lys Asn Thr Asp Ala Ala Ala Leu Leu Ala
            20                  25                  30

Ser His Ala Ile Gln Gly Thr Leu Ser Tyr Pro Leu Val Ser Val Val
        35                  40                  45

Ser Glu Ser Leu Thr Pro Glu
    50                  55

<210> SEQ ID NO 69
<211> LENGTH: 60
<212> TYPE: PRT
<213> ORGANISM: artificial sequence

```
<220> FEATURE:
<223> OTHER INFORMATION: consensus sequence
<220> FEATURE:
<221> NAME/KEY: misc_feature
<222> LOCATION: (3)..(3)
<223> OTHER INFORMATION: Xaa=Lys, Ile or Val
<220> FEATURE:
<221> NAME/KEY: misc_feature
<222> LOCATION: (5)..(5)
<223> OTHER INFORMATION: Xaa=Phe, Tyr or Met
<220> FEATURE:
<221> NAME/KEY: misc_feature
<222> LOCATION: (12)..(12)
<223> OTHER INFORMATION: Xaa=Gln or Leu
<220> FEATURE:
<221> NAME/KEY: misc_feature
<222> LOCATION: (14)..(14)
<223> OTHER INFORMATION: Xaa=Val, Tyr, Ile, Leu or Ser
<220> FEATURE:
<221> NAME/KEY: misc_feature
<222> LOCATION: (15)..(15)
<223> OTHER INFORMATION: Xaa=Gln or Lys
<220> FEATURE:
<221> NAME/KEY: misc_feature
<222> LOCATION: (18)..(18)
<223> OTHER INFORMATION: Xaa=Asp, Ser, Ala, Glu or Gly
<220> FEATURE:
<221> NAME/KEY: misc_feature
<222> LOCATION: (19)..(19)
<223> OTHER INFORMATION: Xaa=Ser or Asn
<220> FEATURE:
<221> NAME/KEY: misc_feature
<222> LOCATION: (20)..(20)
<223> OTHER INFORMATION: Xaa=Asp or Ser
<220> FEATURE:
<221> NAME/KEY: misc_feature
<222> LOCATION: (21)..(21)
<223> OTHER INFORMATION: Xaa=His, Gln or Asp
<220> FEATURE:
<221> NAME/KEY: misc_feature
<222> LOCATION: (24)..(24)
<223> OTHER INFORMATION: Xaa=Lys, Asn, Pro, Gln or Arg
<220> FEATURE:
<221> NAME/KEY: misc_feature
<222> LOCATION: (25)..(25)
<223> OTHER INFORMATION: Xaa=Asn, Ser or Asp
<220> FEATURE:
<221> NAME/KEY: misc_feature
<222> LOCATION: (26)..(26)
<223> OTHER INFORMATION: Xaa=Thr or Ala
<220> FEATURE:
<221> NAME/KEY: misc_feature
<222> LOCATION: (27)..(27)
<223> OTHER INFORMATION: Xaa=Asp, Thr or Gln
<220> FEATURE:
<221> NAME/KEY: misc_feature
<222> LOCATION: (28)..(28)
<223> OTHER INFORMATION: Xaa=Ala, Asp or Ser
<220> FEATURE:
<221> NAME/KEY: misc_feature
<222> LOCATION: (29)..(29)
<223> OTHER INFORMATION: Xaa=Ala or Val
<220> FEATURE:
<221> NAME/KEY: misc_feature
<222> LOCATION: (31)..(31)
<223> OTHER INFORMATION: Xaa=Ala, Asp or Glu
<220> FEATURE:
<221> NAME/KEY: misc_feature
<222> LOCATION: (32)..(32)
<223> OTHER INFORMATION: Xaa=Leu, Phe or Tyr
<220> FEATURE:
<221> NAME/KEY: misc_feature
<222> LOCATION: (34)..(34)
<223> OTHER INFORMATION: Xaa=Ala or Gly
<220> FEATURE:
<221> NAME/KEY: misc_feature
<222> LOCATION: (35)..(35)
<223> OTHER INFORMATION: Xaa=Ser or Ala
<220> FEATURE:
<221> NAME/KEY: misc_feature
```

```
<222> LOCATION: (36)..(36)
<223> OTHER INFORMATION: Xaa=His or Leu
<220> FEATURE:
<221> NAME/KEY: misc_feature
<222> LOCATION: (37)..(37)
<223> OTHER INFORMATION: Xaa=Ala or Ser
<220> FEATURE:
<221> NAME/KEY: misc_feature
<222> LOCATION: (38)..(38)
<223> OTHER INFORMATION: Xaa=Ile, Ser or Ala
<220> FEATURE:
<221> NAME/KEY: misc_feature
<222> LOCATION: (39)..(39)
<223> OTHER INFORMATION: Xaa=Gln, Leu, Val or Arg
<220> FEATURE:
<221> NAME/KEY: misc_feature
<222> LOCATION: (40)..(40)
<223> OTHER INFORMATION: Xaa=Gly or Glu
<220> FEATURE:
<221> NAME/KEY: misc_feature
<222> LOCATION: (41)..(41)
<223> OTHER INFORMATION: Xaa=Thr, Ser, Asn, Arg or Met
<220> FEATURE:
<221> NAME/KEY: misc_feature
<222> LOCATION: (43)..(43)
<223> OTHER INFORMATION: Xaa=Ser, Asp, Gln or Arg
<220> FEATURE:
<221> NAME/KEY: misc_feature
<222> LOCATION: (45)..(45)
<223> OTHER INFORMATION: Xaa=Leu, Ile or Phe
<220> FEATURE:
<221> NAME/KEY: misc_feature
<222> LOCATION: (46)..(46)
<223> OTHER INFORMATION: Xaa=Ser or Pro
<220> FEATURE:
<221> NAME/KEY: misc_feature
<222> LOCATION: (48)..(48)
<223> OTHER INFORMATION: Xaa=Pro or Lys
<220> FEATURE:
<221> NAME/KEY: misc_feature
<222> LOCATION: (49)..(49)
<223> OTHER INFORMATION: Xaa=Leu or Ile
<220> FEATURE:
<221> NAME/KEY: misc_feature
<222> LOCATION: (50)..(50)
<223> OTHER INFORMATION: Xaa=Val, Glu, Arg or Lys
<220> FEATURE:
<221> NAME/KEY: misc_feature
<222> LOCATION: (51)..(51)
<223> OTHER INFORMATION: Xaa=Ser, Ala, Asp or Glu
<220> FEATURE:
<221> NAME/KEY: misc_feature
<222> LOCATION: (53)..(53)
<223> OTHER INFORMATION: Xaa=Val, Lys, Gln, Arg or Thr
<220> FEATURE:
<221> NAME/KEY: misc_feature
<222> LOCATION: (54)..(54)
<223> OTHER INFORMATION: Xaa=Ser or Gly
<220> FEATURE:
<221> NAME/KEY: misc_feature
<222> LOCATION: (56)..(56)
<223> OTHER INFORMATION: Xaa=Ser, Asn, Thr, Pro or Lys
<220> FEATURE:
<221> NAME/KEY: misc_feature
<222> LOCATION: (57)..(57)
<223> OTHER INFORMATION: Xaa=Leu, Met, Ala, Val or Arg
<220> FEATURE:
<221> NAME/KEY: misc_feature
<222> LOCATION: (58)..(58)
<223> OTHER INFORMATION: Xaa=Thr or Glu
<220> FEATURE:
<221> NAME/KEY: misc_feature
<222> LOCATION: (59)..(59)
<223> OTHER INFORMATION: Xaa=Pro, Thr or Ala
<220> FEATURE:
<221> NAME/KEY: misc_feature
<222> LOCATION: (60)..(60)
<223> OTHER INFORMATION: X=Glu, Pro, Ala or Ser

<400> SEQUENCE: 69
```

Gly Ser Xaa Val Xaa Leu Glu Ile Asp Asn Arg Xaa Cys Xaa Xaa Ser
1               5                   10                  15

Ala Xaa Xaa Xaa Xaa Cys Phe Xaa Xaa Xaa Xaa Xaa Ala Xaa Xaa
            20                  25                  30

Leu Xaa Xaa Xaa Xaa Xaa Xaa Xaa Leu Xaa Thr Xaa Xaa Tyr Xaa
        35                  40                  45

Xaa Xaa Xaa Val Xaa Xaa Glu Xaa Xaa Xaa Xaa Xaa
    50                  55                  60

<210> SEQ ID NO 70
<211> LENGTH: 58
<212> TYPE: PRT
<213> ORGANISM: Homo sapiens

<400> SEQUENCE: 70

Gly Ser Ile Val Tyr Leu Glu Ile Asp Asn Arg Gln Cys Val Gln Ala
1               5                   10                  15

Ser Ser Gln Cys Phe Gln Ser Ala Thr Asp Val Ala Ala Phe Leu Gly
            20                  25                  30

Ala Leu Ala Ser Leu Gly Ser Leu Asn Ile Pro Tyr Lys Ile Pro Glu
        35                  40                  45

Ala Val Gln Ser Glu Thr Val Glu Pro Pro
    50                  55

<210> SEQ ID NO 71
<211> LENGTH: 57
<212> TYPE: PRT
<213> ORGANISM: Homo sapiens

<400> SEQUENCE: 71

Gly Ser Ile Val Tyr Pro Glu Ile Asp Asn Arg Gln Cys Val Gln Ala
1               5                   10                  15

Ser Ser Gln Cys Phe Gln Ser Ala Thr Asp Val Ala Ala Phe Leu Gly
            20                  25                  30

Ala Leu Ala Ser Leu Gly Ser Leu Asn Ile Pro Tyr Lys Ile Glu Ala
        35                  40                  45

Val Gln Ser Glu Thr Val Glu Pro Pro
    50                  55

<210> SEQ ID NO 72
<211> LENGTH: 57
<212> TYPE: PRT
<213> ORGANISM: Homo sapiens

<400> SEQUENCE: 72

Gly Ser Ile Asp Tyr Leu Glu Ile Asp Asn Arg Gln Cys Val Gln Ala
1               5                   10                  15

Ser Ser Gln Cys Phe Gln Ser Ala Thr Asp Val Ala Ala Phe Leu Gly
            20                  25                  30

Ala Leu Ala Ser Leu Gly Ser Leu Asn Ile Pro Tyr Lys Ile Glu Ala
        35                  40                  45

Val Gln Ser Glu Thr Val Glu Pro Pro
    50                  55

<210> SEQ ID NO 73
<211> LENGTH: 57
<212> TYPE: PRT
<213> ORGANISM: Homo sapiens

<400> SEQUENCE: 73

Gly Ser Ile Val Tyr Leu Glu Asn Asp Asn Arg Gln Cys Val Gln Ala
1               5                   10                  15

Ser Ser Gln Cys Phe Gln Ser Ala Thr Asp Val Ala Ala Phe Leu Gly
            20                  25                  30

Ala Leu Ala Ser Leu Gly Ser Leu Asn Ile Pro Tyr Lys Ile Glu Ala
        35                  40                  45

Val Gln Ser Glu Thr Val Glu Pro Pro
    50                  55

<210> SEQ ID NO 74
<211> LENGTH: 57
<212> TYPE: PRT
<213> ORGANISM: Homo sapiens

<400> SEQUENCE: 74

Gly Ser Ile Val Tyr Leu Glu Thr Asp Asn Arg Gln Cys Val Gln Ala
1               5                   10                  15

Ser Ser Gln Cys Phe Gln Ser Ala Thr Asp Val Ala Ala Phe Leu Gly
            20                  25                  30

Ala Leu Ala Ser Leu Gly Ser Leu Asn Ile Pro Tyr Lys Ile Glu Ala
        35                  40                  45

Val Gln Ser Glu Thr Val Glu Pro Pro
    50                  55

<210> SEQ ID NO 75
<211> LENGTH: 57
<212> TYPE: PRT
<213> ORGANISM: Homo sapiens

<400> SEQUENCE: 75

Gly Ser Ile Val Tyr Leu Glu Ile Asp Asn Arg Gln Cys Val Gln Ala
1               5                   10                  15

Ser Ser Gln Cys Phe Gln Ser Ala Asn Asp Val Ala Ala Phe Leu Gly
            20                  25                  30

Ala Leu Ala Ser Leu Gly Ser Leu Asn Ile Pro Tyr Lys Ile Glu Ala
        35                  40                  45

Val Gln Ser Glu Thr Val Glu Pro Pro
    50                  55

<210> SEQ ID NO 76
<211> LENGTH: 7671
<212> TYPE: DNA
<213> ORGANISM: Homo sapiens

<400> SEQUENCE: 76
atgccgccgc tcctggcgcc cctgctctgc ctggcgctgc tgcccgcgct cgccgcacga       60
ggcccgcgat gctcccagcc cggtgagacc tgcctgaatg gcgggaagtg tgaagcggcc      120
aatggcacgg aggcctgcgt ctgtggcggg gccttcgtgg gccgcgatg ccaggacccc       180 aacccgtgcc tcagcacccc ctgcaagaac gccgggacat gccacgtggt ggaccgcaga      240
ggcgtggcag actatgcctg cagctgtgcc ctgggcttct ctgggcccct ctgcctgaca      300
cccctggaca tgcctgcct caccaacccc tgccgcaacg gggcacctg cgacctgctc       360 acgctgacgg agtacaagtg ccgctgcccg cccggctggt cagggaaatc gtgccagcag      420
gctgacccgt gcgcctccaa cccctgcgcc aacggtggcc agtgcctgcc cttcgaggcc      480
tcctacatct gccactgccc acccagcttc catggcccca cctgccggca ggatgtcaac      540
gagtgtggcc agaagcccgg gctttgccgc cacggaggca cctgccacaa cgaggtcggc      600

```
tcctaccgct gcgtctgccg cgccacccac actggcccca actgcgagcg gccctacgtg    660
ccctgcagcc cctcgccctg ccagaacggg ggcacctgcc gccccacggg cgacgtcacc    720
cacgagtgtg cctgcctgcc aggcttcacc ggccagaact gtgaggaaaa tatcgacgat    780
tgtccaggaa acaactgcaa gaacgggggt gcctgtgtgg acggcgtgaa cacctacaac    840
tgccgctgcc cgccagagtg gacaggtcag tactgtaccg aggatgtgga cgagtgccag    900
ctgatgccaa atgcctgcca gaacggcggg acctgccaca cacccacggg tggctacaac    960
tgcgtgtgtg tcaacggctg gactggtgag gactgcagcg agaacattga tgactgtgcc   1020
agcgccgcct gcttccacgg cgccacctgc catgaccgtg tggcctcctt ctactgcgag   1080
tgtccccatg gccgcacagg tctgctgtgc cacctcaacg acgcatgcat cagcaacccc   1140
tgtaacgagg gctccaactg cgacaccaac cctgtcaatg gcaaggccat ctgcacctgc   1200
ccctcggggt acacgggccc ggcctgcagc caggacgtgg atgagtgctc gctgggtgcc   1260 aaccctgcg agcatgcggg caagtgcatc aacacgctgg gctccttcga gtgccagtgt   1320
ctgcagggct cacgggcccc cgatgcgag atcgacgtca acgagtgcgt ctcgaacccg   1380
tgccagaacg acgccacctg cctggaccag attggggagt ccagtgcat ctgcatgccc   1440 ggctacgagg gtgtgcactg cgaggtcaac acagacgagt gtgccagcag ccctgcctg   1500 cacaatggcc gctgcctgga caagatcaat gagttccagt gcgagtgccc cacgggcttc   1560
actgggcatc tgtgccagta cgatgtggac gagtgtgcca gcacccctg caagaatggt   1620 gccaagtgcc tggacggacc caacacttac acctgtgtgt gcacggaagg gtacacgggg   1680
acgcactgcg aggtggacat cgatgagtgc gaccccgacc cctgccacta cggctcctgc   1740
aaggacggcc tcgccacctt cacctgcctc tgccgcccag gctacacggg ccaccactgc   1800
gagaccaaca tcaacgagtg ctccagccag ccctgccgcc acgggggcac ctgccaggac   1860
cgcgacaacg cctacctctg cttctgcctg aaggggacca caggacccaa ctgcgagatc   1920
aacctggatg actgtgccag cagcccctgc gactcgggca cctgtctgga caagatcgat   1980
ggctacgagt gtgcctgtga gccgggctac acagggagca tgtgtaacat caacatcgat   2040
gagtgtgcgg gcaaccctg ccacaacggg ggcacctgcg aggacggcat caatggcttc   2100
acctgccgct gccccgaggg ctaccacgac cccacctgcc tgtctgaggt caatgagtgc   2160
aacagcaacc cctgcgtcca cggggcctgc cgggacagcc tcaacgggta caagtgcgac   2220
tgtgaccctg ggtggagtgg gaccaactgt gacatcaaca acaatgagtg tgaatccaac   2280
ccttgtgtca acggcggcac ctgcaaagac atgaccagtg gctacgtgtg cacctgccgg   2340
gagggcttca gcggtcccaa ctgccagacc aacatcaacg agtgtgcgtc caacccatgt   2400
ctgaaccagg gcacgtgtat tgacgacgtt gccgggtaca agtgcaactg cctgctgccc   2460
tacacaggtg ccacgtgtga ggtggtgctg gcccgtgtg ccccagccc ctgcagaaac   2520 ggcgggagt gcaggcaatc cgaggactat gagagcttct cctgtgtctg ccccacgggc   2580
tggcaagcag ggcagacctg tgaggtcgac atcaacgagt gcgttctgag cccgtgccgg   2640
cacggcgcat cctgccagaa cacccacggc ggctaccgct gccactgcca ggccggctac   2700
agtgggcgca actgcgagac cgacatcgac gactgccggc caacccgtg tcacaacggg   2760 ggctcctgca cagacggcat caacacggcc ttctgcgact gctgcccgg cttcggggc   2820 actttctgtg aggaggacat caacgagtgt gccagtgacc cctgccgcaa cggggccaac   2880
tgcacggact gcgtggacag ctacgcgtgc acctgccccg caggcttcag cgggatccac   2940
tgtgagaaca acacgcctga ctgcacagag agctcctgct tcaacggtgg cacctgcgtg   3000
```

-continued

```
gacggcatca actcgttcac ctgcctgtgt ccacccggct tcacgggcag ctactgccag      3060
cacgatgtca atgagtgcga ctcacagccc tgcctgcatg gcggcacctg tcaggacggc      3120
tgcggctcct acaggtgcac ctgccccag ggctacactg gccccaactg ccagaacctt       3180
gtgcactggt gtgactcctc gccctgcaag aacggcggca atgctggca gacccacacc       3240 cagtaccgct gcgagtgccc cagcggctgg accggccttt actgcgacgt gcccagcgtg      3300
tcctgtgagg tggctgcgca gcgacaaggt gttgacgttg cccgcctgtg ccagcatgga      3360
gggctctgtg tggacgcggg caacacgcac cactgccgct gccaggcggg ctacacaggc      3420
agctactgtg aggacctggt ggacgagtgc tcacccagcc cctgccagaa cggggccacc      3480
tgcacggact acctgggcgg ctactcctgc aagtgcgtgg ccggctacca cggggtgaac      3540
tgctctgagg agatcgacga gtgcctctcc cacccctgcc agaacggggg cacctgcctc      3600
gacctcccca cacctacaa gtgctcctgc ccacggggca ctcagggtgt gcactgtgag       3660
atcaacgtgg acgactgcaa tcccccccgtt gaccccgtgt cccggagccc caagtgccttt    3720 aacaacggca cctgcgtgga ccaggtgggc ggctacagct gcacctgccc gccgggcttc      3780
gtgggtgagc gctgtgaggg ggatgtcaac gagtgcctgt ccaatccctg cgacgcccgt      3840
ggcacccaga actgcgtgca gcgcgtcaat gacttccact gcgagtgccg tgctggtcac      3900
accgggcgcc gctgcgagtc cgtcatcaat ggctgcaaag gcaagccctg caagaatggg      3960
ggcacctgcg ccgtggcctc caacaccgcc cgcgggttca tctgcaagtg ccctgcgggc      4020
ttcgagggcg ccacgtgtga gaatgacgct cgtacctgcg gcagcctgcg ctgcctcaac      4080
ggcggcacat gcatctccgg cccgcgcagc cccacctgcc tgtgcctggg cccccttcacg    4140 ggccccgaat gccagttccc ggccagcagc ccctgcctgg gcggcaaccc ctgctacaac      4200
caggggacct gtgagcccac atccgagagc cccttctacc gttgcctgtg ccccgccaaa      4260
ttcaacgggt tcttgtgcca catcctggac tacagcttcg ggggtgggc cgggcgcgac       4320 atccccccgc cgctgatcga ggaggcgtgc gagctgcccg agtgccagga ggacgcgggc      4380
aacaaggtct gcagcctgca gtgcaacaac acgcgtgcg gctgggacgg cggtgactgc      4440
tccctcaact tcaatgaccc ctggaagaac tgcacgcagt ctctgcagtg ctggaagtac      4500
ttcagtgacg gccactgtga cagccagtgc aactcagccg gctgcctctt cgacggcttt      4560
gactgccagc gtgcggaagg ccagtgcaac ccctgtacg accagtactg caaggaccac      4620
ttcagcgacg ggcactgcga ccagggctgc aacagcgcgg agtgcgagtg ggacgggctg      4680
gactgtgcgg agcatgtacc cgagaggctg gcggccggca cgctggtggt ggtggtgctg      4740
atgccgccgg agcagctgcg caacagctcc ttccacttcc tgcgggagct cagccgcgtg      4800
ctgcacacca acgtggtctt caagcgtgac gcacacggcc agcagatgat cttcccctac      4860 tacgccgcg aggaggagct gcgcaagcac cccatcaagc gtgccgccga gggctgggcc      4920
gcacctgacg ccctgctggg ccaggtgaag gcctcgctgc tccctggtgg cagcgagggt      4980
gggcggcggc ggagggagct ggaccccatg acgtccgcg gctccatcgt ctacctggag      5040
attgacaacc ggcagtgtgt gcaggcctcc tcgcagtgct tccagagtgc caccgacgtg      5100
gccgcattcc tgggagcgct cgcctcgctg ggcagcctca acatccccta caagatcgag      5160
gccgtgcaga gtgagaccgt ggagccgccc ccgccgcgcg agctgcactt catgtacgtg      5220
gcggcggccg cctttgtgct tctgttcttc gtgggctgcg gggtgctgct gtcccgcaag      5280
cgccggcggc agcatggcca gctctggttc cctgagggct tcaaagtgtc tgaggccagc      5340
aagaagaagc ggcggagcc cctcggcgag gactccgtgg gcctcaagcc cctgaagaac      5400
```

```
gcttcagacg gtgccctcat ggacgacaac cagaatgagt gggggggacga ggacctggag    5460 accaagaagt tccggttcga ggagcccgtg gttctgcctg acctggacga ccagacagac    5520
caccggcagt ggactcagca gcacctggat gccgctgacc tgcgcatgtc tgccatggcc    5580
cccacaccgc cccagggtga ggttgacgcc gactgcatgg acgtcaatgt ccgcgggcct    5640
gatggcttca ccccgctcat gatcgcctcc tgcagcgggg gcggcctgga gacgggcaac    5700
agcgaggaag aggaggacgc gccggccgtc atctccgact tcatctacca gggcgccagc    5760
ctgcacaacc agacagaccg cacgggcgag accgccttgc acctggccgc ccgctactca    5820
cgctctgatg ccgccaagcg cctgctggag gccagcgcag atgccaacat ccaggacaac    5880
atgggccgca ccccgctgca tgcggctgtg tctgccgacg cacaaggtgt cttccagatc    5940
ctgatccgga accgagccac agacctggat gcccgcatgc atgatggcac gacgccactg    6000
atcctggctg cccgcctggc cgtggagggc atgctggagg acctcatcaa ctcacacgcc    6060
gacgtcaacg ccgtagatga cctgggcaag tccgccctgc actgggccgc cgccgtgaac    6120
aatgtggatg ccgcagttgt gctcctgaag aacggggcta acaaagatat gcagaacaac    6180
agggaggaga caccctgtt tctggccgcc cgggagggca gctacgagac cgccaaggtg    6240
ctgctggacc actttgccaa ccgggacatc acggatcata tggaccgcct gccgcgcgac    6300
atcgcacagg agcgcatgca tcacgacatc gtgaggctgc tggacgagta caacctggtg    6360
cgcagcccgc agctgcacgg agcccgctg ggggcacgc ccaccctgtc gccccgctc     6420 tgctcgccca acggctacct gggcagcctc aagcccggcg tgcagggcaa gaaggtccgc    6480
aagcccagca gcaaaggcct ggcctgtgga agcaaggagg ccaaggacct caaggcacgg    6540
aggaagaagt cccaggacgg caagggctgc ctgctggaca gctccggcat gctctcgccc    6600
gtggactccc tggagtcacc ccatggctac ctgtcagacg tggcctcgcc gccactgctg    6660 ccctcccccgt tccagcagtc tccgtccgtg cccctcaacc acctgcctgg gatgcccgac    6720
acccacctgg gcatcgggca cctgaacgtg gcggccaagc ccgagatggc ggcgctgggt    6780
gggggcggcc ggctggcctt tgagactggc ccacctcgtc tctcccacct gcctgtggcc    6840
tctggcacca gcaccgtcct gggctccagc agcggagggg ccctgaattt cactgtgggc    6900
gggtccacca gtttgaatgg tcaatgcgag tggctgtccc ggctgcagag cggcatggtg    6960
ccgaaccaat acaaccctct gcgggggagt gtggcaccag gcccctgag cacacaggcc    7020 ccctccctgc agcatggcat ggtaggcccg ctgcacagta gccttgctgc cagcgccctg    7080
tcccagatga tgagctacca gggcctgccc agcacccggc tggccaccca gcctcacctg    7140
gtgcagaccc agcaggtgca gccacaaaac ttacagatgc agcagcagaa cctgcagcca    7200
gcaaacatcc agcagcagca aagcctgcag ccgccaccac caccaccaca gccgcacctt    7260
ggcgtgagct cagcagccag cggccacctg ggccggagct tcctgagtgg agagccgagc    7320
caggcagacg tgcagccact gggcccagc agcctggcgg tgcacactat tctgcccag     7380 gagagccccg ccctgcccac gtcgctgcca tcctcgctgg tcccaccgt gaccgcagcc    7440 cagttcctga cgccccctc gcagcacagc tactcctcgc ctgtggacaa caccccgagc    7500
caccagctac aggtgcctga gcacccctt ctcacccgt ccctgagtc ccctgaccag      7560 tggtccagct cgtcccgca ttccaacgtc tccgactggt ccgagggcgt ctccagcct     7620 cccaccagca tgcagtccca gatcgcccgc attccggagg ccttcaagta a             7671
```

<210> SEQ ID NO 77
<211> LENGTH: 52

```
<212> TYPE: PRT
<213> ORGANISM: Homo sapiens

<400> SEQUENCE: 77

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
                20                  25                  30

Thr Asn Val Val Phe Lys Arg Asp Ala His Gly Gln Gln Met Ile Phe
            35                  40                  45

Pro Tyr Tyr Gly
    50

<210> SEQ ID NO 78
<211> LENGTH: 38
<212> TYPE: DNA
<213> ORGANISM: Homo sapiens

<400> SEQUENCE: 78
tttgaattcg ggctggactg tgcggagcat gtacccga                         38

<210> SEQ ID NO 79
<211> LENGTH: 37
<212> TYPE: DNA
<213> ORGANISM: Homo sapiens

<400> SEQUENCE: 79
tttggatcct ccggaatgcg ggcgatctgg gactgca                          37

<210> SEQ ID NO 80
<211> LENGTH: 20
<212> TYPE: DNA
<213> ORGANISM: Homo sapiens

<400> SEQUENCE: 80
agccccctgt acgaccagta                                             20

<210> SEQ ID NO 81
<211> LENGTH: 18
<212> TYPE: DNA
<213> ORGANISM: Homo sapiens

<400> SEQUENCE: 81
cttgcgcagc tcctcctc                                               18

<210> SEQ ID NO 82
<211> LENGTH: 20
<212> TYPE: DNA
<213> ORGANISM: Homo sapiens

<400> SEQUENCE: 82
gaccagtact gcaaggacca                                             20

<210> SEQ ID NO 83
<211> LENGTH: 18
<212> TYPE: DNA
<213> ORGANISM: Homo sapiens

<400> SEQUENCE: 83
tcctcgcggc cgtagtag                                               18

<210> SEQ ID NO 84
<211> LENGTH: 18
```

```
<212> TYPE: DNA
<213> ORGANISM: Homo sapiens

<400> SEQUENCE: 84
gtgctgcaca ccaacgtg                                                  18

<210> SEQ ID NO 85
<211> LENGTH: 18
<212> TYPE: DNA
<213> ORGANISM: Homo sapiens

<400> SEQUENCE: 85
gagggcccag gagagttg                                                  18

<210> SEQ ID NO 86
<211> LENGTH: 20
<212> TYPE: DNA
<213> ORGANISM: Homo sapiens

<400> SEQUENCE: 86
gcacacggcc agcagatgat                                                20

<210> SEQ ID NO 87
<211> LENGTH: 17
<212> TYPE: DNA
<213> ORGANISM: Homo sapiens

<400> SEQUENCE: 87
cgccgggtct cactcac                                                   17

<210> SEQ ID NO 88
<211> LENGTH: 18
<212> TYPE: DNA
<213> ORGANISM: Homo sapiens

<400> SEQUENCE: 88
gtggcgtcat gggcctca                                                  18

<210> SEQ ID NO 89
<211> LENGTH: 20
<212> TYPE: DNA
<213> ORGANISM: Homo sapiens

<400> SEQUENCE: 89
tagcaactgg cacaaacagc                                                20

<210> SEQ ID NO 90
<211> LENGTH: 18
<212> TYPE: DNA
<213> ORGANISM: Homo sapiens

<400> SEQUENCE: 90
catgggcctc agtgtcct                                                  18

<210> SEQ ID NO 91
<211> LENGTH: 20
<212> TYPE: DNA
<213> ORGANISM: Homo sapiens

<400> SEQUENCE: 91
gcacaaacag ccagcgtgtc                                                20

<210> SEQ ID NO 92
<211> LENGTH: 18
```

```
<212> TYPE: DNA
<213> ORGANISM: Homo sapiens

<400> SEQUENCE: 92
gcagcatggc atggtagg                                                   18

<210> SEQ ID NO 93
<211> LENGTH: 25
<212> TYPE: DNA
<213> ORGANISM: Homo sapiens

<400> SEQUENCE: 93
aacatgtgtt ttaaaaaggc tcctc                                           25

<210> SEQ ID NO 94
<211> LENGTH: 20
<212> TYPE: DNA
<213> ORGANISM: Homo sapiens

<400> SEQUENCE: 94
aaacatccag cagcagcaaa                                                 20

<210> SEQ ID NO 95
<211> LENGTH: 21
<212> TYPE: DNA
<213> ORGANISM: Homo sapiens

<400> SEQUENCE: 95
cacaggcgag gagtagctgt g                                               21

<210> SEQ ID NO 96
<211> LENGTH: 18
<212> TYPE: DNA
<213> ORGANISM: Homo sapiens

<400> SEQUENCE: 96
gtgaccgcag cccagttc                                                   18

<210> SEQ ID NO 97
<211> LENGTH: 18
<212> TYPE: DNA
<213> ORGANISM: Homo sapiens

<400> SEQUENCE: 97
aaaggaagcc ggggtctc                                                   18

<210> SEQ ID NO 98
<211> LENGTH: 21
<212> TYPE: DNA
<213> ORGANISM: Homo sapiens

<400> SEQUENCE: 98
agactggccc acctcgtctc t                                               21

<210> SEQ ID NO 99
<211> LENGTH: 20
<212> TYPE: DNA
<213> ORGANISM: Homo sapiens

<400> SEQUENCE: 99
gctctccact caggaagctc                                                 20

<210> SEQ ID NO 100
<211> LENGTH: 20
```

```
<212> TYPE: DNA
<213> ORGANISM: Homo sapiens

<400> SEQUENCE: 100
cgtctctccc acctgcctgt                                              20

<210> SEQ ID NO 101
<211> LENGTH: 18
<212> TYPE: DNA
<213> ORGANISM: Homo sapiens

<400> SEQUENCE: 101
ctgagctcac gccaaggt                                                18

<210> SEQ ID NO 102
<211> LENGTH: 48
<212> TYPE: PRT
<213> ORGANISM: Homo sapiens

<400> SEQUENCE: 102
```

Ala Ala Gly Thr Leu Val Glu Val Val Leu Met Pro Pro Glu Gln Leu
1               5                   10                  15

Arg Asn Ser Ser Phe His Phe Leu Arg Glu Leu Ser Arg Val Leu His
            20                  25                  30

Thr Asn Val Val Phe Lys Arg Asp Ala His Gly Gln Gln Met Ile Phe
        35                  40                  45

```
<210> SEQ ID NO 103
<211> LENGTH: 48
<212> TYPE: PRT
<213> ORGANISM: Homo sapiens

<400> SEQUENCE: 103
```

Ala Ala Gly Thr Leu Val Val Glu Val Leu Met Pro Pro Glu Gln Leu
1               5                   10                  15

Arg Asn Ser Ser Phe His Phe Leu Arg Glu Leu Ser Arg Val Leu His
            20                  25                  30

Thr Asn Val Val Phe Lys Arg Asp Ala His Gly Gln Gln Met Ile Phe
        35                  40                  45

```
<210> SEQ ID NO 104
<211> LENGTH: 48
<212> TYPE: PRT
<213> ORGANISM: Homo sapiens

<400> SEQUENCE: 104
```

Ala Ala Gly Thr Leu Val Val Val Gly Leu Met Pro Pro Glu Gln Leu
1               5                   10                  15

Arg Asn Ser Ser Phe His Phe Leu Arg Glu Leu Ser Arg Val Leu His
            20                  25                  30

Thr Asn Val Val Phe Lys Arg Asp Ala His Gly Gln Gln Met Ile Phe
        35                  40                  45

```
<210> SEQ ID NO 105
<211> LENGTH: 48
<212> TYPE: PRT
<213> ORGANISM: Homo sapiens

<400> SEQUENCE: 105
```

Ala Ala Gly Thr Leu Val Val Val Val Leu Met Pro Pro Glu Gln Pro
1               5                   10                  15

Arg Asn Ser Ser Phe His Phe Leu Arg Glu Leu Ser Arg Val Leu His

-continued

```
            20                  25                  30

Thr Asn Val Val Phe Lys Arg Asp Ala His Gly Gln Gln Met Ile Phe
        35                  40                  45

<210> SEQ ID NO 106
<211> LENGTH: 48
<212> TYPE: PRT
<213> ORGANISM: Homo sapiens

<400> SEQUENCE: 106

Ala Ala Gly Thr Leu Val Val Val Leu Met Pro Pro Glu Gln Gln
1               5                   10                  15

Arg Asn Ser Ser Phe His Phe Leu Arg Glu Leu Ser Arg Val Leu His
            20                  25                  30

Thr Asn Val Val Phe Lys Arg Asp Ala His Gly Gln Gln Met Ile Phe
        35                  40                  45

<210> SEQ ID NO 107
<211> LENGTH: 48
<212> TYPE: PRT
<213> ORGANISM: Homo sapiens

<400> SEQUENCE: 107

Ala Ala Gly Thr Leu Val Val Val Leu Met Pro Pro Val Gln Leu
1               5                   10                  15

Arg Asn Ser Ser Phe His Phe Leu Arg Glu Leu Ser Arg Val Leu His
            20                  25                  30

Thr Asn Val Val Phe Lys Arg Asp Ala His Gly Gln Gln Met Ile Phe
        35                  40                  45

<210> SEQ ID NO 108
<211> LENGTH: 48
<212> TYPE: PRT
<213> ORGANISM: Homo sapiens

<400> SEQUENCE: 108

Ala Ala Gly Thr Leu Val Val Val Leu Met Pro Pro Glu Gln Leu
1               5                   10                  15

Arg Asn Ser Ser Phe His Phe Leu Arg Glu Pro Ser Arg Val Leu His
            20                  25                  30

Thr Asn Val Val Phe Lys Arg Asp Ala His Gly Gln Gln Met Ile Phe
        35                  40                  45

<210> SEQ ID NO 109
<211> LENGTH: 48
<212> TYPE: PRT
<213> ORGANISM: Homo sapiens

<400> SEQUENCE: 109

Ala Ala Gly Thr Leu Val Val Val Leu Met Pro Pro Glu Gln Leu
1               5                   10                  15

Arg Asn Ser Ser Phe His Phe Leu Arg Glu His Ser Arg Val Leu His
            20                  25                  30

Thr Asn Val Val Phe Lys Arg Asp Ala His Gly Gln Gln Met Ile Phe
        35                  40                  45

<210> SEQ ID NO 110
<211> LENGTH: 48
<212> TYPE: PRT
<213> ORGANISM: Homo sapiens

<400> SEQUENCE: 110
```

Ala Ala Gly Thr Leu Val Val Val Leu Met Pro Pro Glu Gln Leu
1               5                   10                  15

Arg Asn Ser Ser Phe His Phe Leu Arg Glu Leu Ile Arg Val Leu His
                20                  25                  30

Thr Asn Val Val Phe Lys Arg Asp Ala His Gly Gln Gln Met Ile Phe
                35                  40                  45

<210> SEQ ID NO 111
<211> LENGTH: 48
<212> TYPE: PRT
<213> ORGANISM: Homo sapiens

<400> SEQUENCE: 111

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
                20                  25                  30

Asn Asn Val Val Phe Lys Arg Asp Ala His Gly Gln Gln Met Ile Phe
                35                  40                  45

<210> SEQ ID NO 112
<211> LENGTH: 48
<212> TYPE: PRT
<213> ORGANISM: Homo sapiens

<400> SEQUENCE: 112

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
                20                  25                  30

Thr Asn Glu Val Phe Lys Arg Asp Ala His Gly Gln Gln Met Ile Phe
                35                  40                  45

<210> SEQ ID NO 113
<211> LENGTH: 48
<212> TYPE: PRT
<213> ORGANISM: Homo sapiens

<400> SEQUENCE: 113

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
                20                  25                  30

Thr Asn Gly Val Phe Lys Arg Asp Ala His Gly Gln Gln Met Ile Phe
                35                  40                  45

<210> SEQ ID NO 114
<211> LENGTH: 48
<212> TYPE: PRT
<213> ORGANISM: Homo sapiens

<400> SEQUENCE: 114

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
                20                  25                  30

Thr Asn Val Val Phe Lys Ser Asp Ala His Gly Gln Gln Met Ile Phe
                35                  40                  45

<210> SEQ ID NO 115

```
<211> LENGTH: 48
<212> TYPE: PRT
<213> ORGANISM: Homo sapiens

<400> SEQUENCE: 115

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
            20                  25                  30

Thr Asn Val Val Phe Lys Arg Asp Ala His Gly Gln Gln Met Asn Phe
        35                  40                  45

<210> SEQ ID NO 116
<211> LENGTH: 48
<212> TYPE: PRT
<213> ORGANISM: Homo sapiens

<400> SEQUENCE: 116

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
            20                  25                  30

Thr Asn Val Val Phe Lys Arg Asp Ala His Gly Gln Gln Met Thr Phe
        35                  40                  45

<210> SEQ ID NO 117
<211> LENGTH: 48
<212> TYPE: PRT
<213> ORGANISM: Homo sapiens

<400> SEQUENCE: 117

Ala Ala Gly Thr Leu Val Val Val Leu Met Pro Pro Glu Gln Leu
1               5                   10                  15

Arg Asn Ser Ser Phe Arg Ser Leu Arg Glu Leu Ser Arg Val Leu His
            20                  25                  30

Thr Asn Val Val Phe Lys Arg Asp Ala His Gly Gln Gln Met Ile Phe
        35                  40                  45

<210> SEQ ID NO 118
<211> LENGTH: 47
<212> TYPE: PRT
<213> ORGANISM: Homo sapiens

<400> SEQUENCE: 118

Ala Ala Gly Thr Leu Val Val Val Leu Met Pro Glu Gln Leu Arg
1               5                   10                  15

Asn Ser Ser Phe His Phe Leu Arg Glu Leu Ser Arg Val Leu His Thr
            20                  25                  30

Asn Val Val Phe Lys Arg Asp Ala His Gly Gln Gln Met Ile Phe
        35                  40                  45

<210> SEQ ID NO 119
<211> LENGTH: 53
<212> TYPE: PRT
<213> ORGANISM: Homo sapiens

<400> SEQUENCE: 119

Ala Ala Gly Thr Leu Val Val Val Leu Met Pro Pro Glu Gln Leu
1               5                   10                  15

Arg Asn Ser Ser Phe His Phe Ala Leu Arg Glu Leu Ser Arg Val Leu
            20                  25                  30
```

His Thr Asn Val Val Phe Lys Arg Asp Ala His Gly Gln Gln Met Ile
            35                  40                  45

Phe Pro Tyr Tyr Gly
    50

<210> SEQ ID NO 120
<211> LENGTH: 53
<212> TYPE: PRT
<213> ORGANISM: Homo sapiens

<400> SEQUENCE: 120

Ala Ala Gly Thr Leu Val Val Val Leu Met Pro Pro Glu Gln Leu
1               5                   10                  15

Arg Asn Ser Ser Phe His Leu Tyr Leu Arg Glu Leu Ser Arg Val Leu
                20                  25                  30

His Thr Asn Val Val Phe Lys Arg Asp Ala His Gly Gln Gln Met Ile
            35                  40                  45

Phe Pro Tyr Tyr Gly
    50

<210> SEQ ID NO 121
<211> LENGTH: 54
<212> TYPE: PRT
<213> ORGANISM: Homo sapiens

<400> SEQUENCE: 121

Ala Ala Gly Thr Leu Val Val Val Leu Met Pro Pro Glu Gln Leu
1               5                   10                  15

Arg Asn Ser Ser Phe His Ser His Leu Lys Arg Glu Leu Ser Arg Val
                20                  25                  30

Leu His Thr Asn Val Val Phe Lys Arg Asp Ala His Gly Gln Gln Met
            35                  40                  45

Ile Phe Pro Tyr Tyr Gly
    50

<210> SEQ ID NO 122
<211> LENGTH: 56
<212> TYPE: PRT
<213> ORGANISM: Homo sapiens

<400> SEQUENCE: 122

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
                20                  25                  30

Thr Asn Val Leu Pro Pro Pro Ala Phe Lys Arg Asp Ala His Gly Gln
            35                  40                  45

Gln Met Ile Phe Pro Tyr Tyr Gly
    50                  55

<210> SEQ ID NO 123
<211> LENGTH: 54
<212> TYPE: PRT
<213> ORGANISM: Homo sapiens

<400> SEQUENCE: 123

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
                20                  25                  30

-continued

Thr Asn Val Leu Gly Arg Phe Lys Arg Asp Ala His Gly Gln Gln Met
            35                  40                  45

Ile Phe Pro Tyr Tyr Gly
    50

<210> SEQ ID NO 124
<211> LENGTH: 57
<212> TYPE: PRT
<213> ORGANISM: Homo sapiens

<400> SEQUENCE: 124

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
                20                  25                  30

Thr Asn Val Val Phe Glu Arg Ala Arg Ser Lys Arg Asp Ala His Gly
            35                  40                  45

Gln Gln Met Ile Phe Pro Tyr Tyr Gly
    50                  55

<210> SEQ ID NO 125
<211> LENGTH: 53
<212> TYPE: PRT
<213> ORGANISM: Homo sapiens

<400> SEQUENCE: 125

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
                20                  25                  30

Thr Asn Val Val Phe His Lys Arg Asp Ala His Gly Gln Gln Met Ile
            35                  40                  45

Phe Pro Tyr Tyr Gly
    50

<210> SEQ ID NO 126
<211> LENGTH: 53
<212> TYPE: PRT
<213> ORGANISM: Homo sapiens

<400> SEQUENCE: 126

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
                20                  25                  30

Thr Asn Val Val Phe Asp Lys Arg Asp Ala His Gly Gln Gln Met Ile
            35                  40                  45

Phe Pro Tyr Tyr Gly
    50

<210> SEQ ID NO 127
<211> LENGTH: 53
<212> TYPE: PRT
<213> ORGANISM: Homo sapiens

<400> SEQUENCE: 127

Ala Ala Gly Thr Leu Val Val Val Leu Met Pro Pro Glu Gln Leu
1               5                   10                  15

Arg Asn Ser Ser Phe His Phe Leu Arg Glu Leu Ser Arg Val Leu His
                20                  25                  30

Thr Asn Val Val Phe Lys Arg Asp Ala His Gly Gln Gln Met Ile Leu
        35                  40                  45

Gly Pro Tyr Tyr Gly
    50

<210> SEQ ID NO 128
<211> LENGTH: 57
<212> TYPE: PRT
<213> ORGANISM: Homo sapiens

<400> SEQUENCE: 128

Gly Ser Ile Val Tyr Leu Glu Ile Asp Asn Arg Gln Cys Val Gln Ala
1               5                   10                  15

Ser Ser Gln Cys Phe Gln Ser Ala Thr Asp Val Ala Ala Phe Leu Gly
            20                  25                  30

Ala Leu Ala Ser Leu Gly Ser Leu Asn Ile Pro Tyr Lys Thr Glu Ala
        35                  40                  45

Val Gln Ser Glu Thr Val Glu Pro Pro
    50                  55

<210> SEQ ID NO 129
<211> LENGTH: 57
<212> TYPE: PRT
<213> ORGANISM: Homo sapiens

<400> SEQUENCE: 129

Gly Ser Ile Val Tyr Leu Glu Ile Asp Asn Arg Gln Cys Val Gln Ala
1               5                   10                  15

Ser Ser Gln Cys Phe Gln Ser Ala Thr Asp Val Ala Pro Phe Leu Gly
            20                  25                  30

Ala Leu Ala Ser Leu Gly Ser Leu Asn Ile Pro Tyr Lys Ile Glu Ala
        35                  40                  45

Val Gln Ser Glu Thr Val Glu Pro Pro
    50                  55

<210> SEQ ID NO 130
<211> LENGTH: 57
<212> TYPE: PRT
<213> ORGANISM: Homo sapiens

<400> SEQUENCE: 130

Gly Ser Ile Val Tyr Leu Glu Ile Asp Asn Arg Gln Cys Val Gln Ala
1               5                   10                  15

Ser Ser Gln Cys Phe Gln Ser Ala Thr Asp Val Ala Ala Phe Leu Gly
            20                  25                  30

Ala Leu Ala Ser Pro Gly Ser Leu Asn Ile Pro Tyr Lys Ile Glu Ala
        35                  40                  45

Val Gln Ser Glu Thr Val Glu Pro Pro
    50                  55

<210> SEQ ID NO 131
<211> LENGTH: 57
<212> TYPE: PRT
<213> ORGANISM: Homo sapiens

<400> SEQUENCE: 131

Gly Ser Ile Val Tyr Leu Glu Ile Asp Asn Arg Gln Cys Val Gln Ala
1               5                   10                  15

Ser Ser Gln Cys Phe Gln Leu Ala Thr Asp Val Ala Ala Phe Leu Gly
            20                  25                  30

```
Ala Leu Ala Ser Leu Gly Ser Leu Asn Ile Pro Tyr Lys Ile Glu Ala
        35                  40                  45

Val Gln Ser Glu Thr Val Glu Pro Pro
 50                  55
```

<210> SEQ ID NO 132
<211> LENGTH: 60
<212> TYPE: PRT
<213> ORGANISM: Homo sapiens

<400> SEQUENCE: 132

```
Gly Ser Ile Val Ser Thr Leu Tyr Leu Glu Ile Asp Asn Arg Gln Cys
 1               5                   10                  15

Val Gln Ala Ser Ser Gln Cys Phe Gln Ser Ala Thr Asp Val Ala Ala
             20                  25                  30

Phe Leu Gly Ala Leu Ala Ser Leu Gly Ser Leu Asn Ile Pro Tyr Lys
         35                  40                  45

Ile Glu Ala Val Gln Ser Glu Thr Val Glu Pro Pro
     50                  55                  60
```

<210> SEQ ID NO 133
<211> LENGTH: 57
<212> TYPE: PRT
<213> ORGANISM: Homo sapiens

<400> SEQUENCE: 133

```
Gly Ser Ile Val Tyr Leu Glu Ile Asp Asn Arg Gln Cys Val Gln Ala
 1               5                   10                  15

Ser Ser Gln Cys Phe Gln Ser Ala Asn Asp Val Ala Ala Phe Leu Gly
             20                  25                  30

Ala Leu Ala Ser Leu Gly Ser Leu Asn Ile Pro Tyr Lys Ile Glu Ala
         35                  40                  45

Val Gln Ser Glu Thr Val Glu Pro Pro
 50                  55
```

<210> SEQ ID NO 134
<211> LENGTH: 57
<212> TYPE: PRT
<213> ORGANISM: Homo sapiens

<400> SEQUENCE: 134

```
Gly Ser Ile Val Tyr Leu Glu Asn Asp Asn Arg Gln Cys Val Gln Ala
 1               5                   10                  15

Ser Ser Gln Cys Phe Gln Ser Ala Thr Asp Val Ala Ala Phe Leu Gly
             20                  25                  30

Ala Leu Ala Ser Leu Gly Ser Leu Asn Ile Pro Tyr Lys Ile Glu Ala
         35                  40                  45

Val Gln Ser Glu Thr Val Glu Pro Pro
 50                  55
```

<210> SEQ ID NO 135
<211> LENGTH: 57
<212> TYPE: PRT
<213> ORGANISM: Homo sapiens

<400> SEQUENCE: 135

```
Gly Ser Ile Asp Tyr Leu Glu Ile Asp Asn Arg Gln Cys Val Gln Ala
 1               5                   10                  15

Ser Ser Gln Cys Phe Gln Ser Ala Thr Asp Val Ala Ala Phe Leu Gly
             20                  25                  30
```

-continued

Ala Leu Ala Ser Leu Gly Ser Leu Asn Ile Pro Tyr Lys Ile Glu Ala
            35                  40                  45

Val Gln Ser Glu Thr Val Glu Pro Pro
 50                  55

<210> SEQ ID NO 136
<211> LENGTH: 57
<212> TYPE: PRT
<213> ORGANISM: Homo sapiens

<400> SEQUENCE: 136

Gly Ser Ile Val Tyr Pro Glu Ile Asp Asn Arg Gln Cys Val Gln Ala
1               5                   10                  15

Ser Ser Gln Cys Phe Gln Ser Ala Thr Asp Val Ala Ala Phe Leu Gly
            20                  25                  30

Ala Leu Ala Ser Leu Gly Ser Leu Asn Ile Pro Tyr Lys Ile Glu Ala
            35                  40                  45

Val Gln Ser Glu Thr Val Glu Pro Pro
 50                  55

<210> SEQ ID NO 137
<211> LENGTH: 70
<212> TYPE: PRT
<213> ORGANISM: Homo sapiens

<400> SEQUENCE: 137

Gly Ser Ile Val Tyr Leu Glu Ile Asp Asn Arg Gln Cys Val Gln Ala
1               5                   10                  15

Ser Ser Gln Cys Phe Gln Ser Ala Thr Asp Val Ala Ala Phe Leu Gly
            20                  25                  30

Ala Leu Ala Ser Leu Gly Ser Leu Asn Ile Pro Tyr Lys Ile Glu Arg
            35                  40                  45

Leu Gly Ser Leu Asn Ile Pro Tyr Lys Ile Glu Ala Val Gln Ser
 50                  55                  60

Glu Thr Val Glu Pro Pro
65                  70

<210> SEQ ID NO 138
<211> LENGTH: 81
<212> TYPE: PRT
<213> ORGANISM: Homo sapiens

<400> SEQUENCE: 138

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
            35                  40                  45

Ala Leu Ser Gln Met Met Ser Tyr Gln Gly Leu Pro Ser Thr Arg Leu
 50                  55                  60

Ala Thr Gln Pro His Leu Val Thr Gln Gln Val Gln Pro Gln Asn
65                  70                  75                  80

Leu

<210> SEQ ID NO 139
<211> LENGTH: 168
<212> TYPE: PRT
<213> ORGANISM: Homo sapiens

```
<400> SEQUENCE: 139

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
            115                 120                 125

Pro Ser Gln Ala Asp Val Gln Pro Leu Gly Pro Ser Ser Leu Ala Val
        130                 135                 140

His Thr Ile Leu Pro Gln Glu Ser Pro Ala Leu Pro Thr Ser Leu Pro
145                 150                 155                 160

Ser Leu Ile Leu Trp Ser His Pro
                165

<210> SEQ ID NO 140
<211> LENGTH: 134
<212> TYPE: PRT
<213> ORGANISM: Homo sapiens

<400> SEQUENCE: 140

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Pro Gln Pro His Leu Gly Val
            100                 105                 110

Ser Ser Ala Ala Ser Gly His Leu Gly Arg Ser Phe Leu Ser Gly Glu
            115                 120                 125

Pro Ser Gln Ala Val Leu
        130

<210> SEQ ID NO 141
<211> LENGTH: 116
<212> TYPE: PRT
<213> ORGANISM: Homo sapiens

<400> SEQUENCE: 141

Trp Leu Ser Arg Leu Gln Ser Gly Met Val Pro Asn Gln Tyr Asn Pro
1               5                   10                  15
```

```
Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Cys Gly Leu Ser Pro Arg Pro His His His Ser
            100                 105                 110

Arg Thr Leu Ala
        115

<210> SEQ ID NO 142
<211> LENGTH: 99
<212> TYPE: PRT
<213> ORGANISM: Homo sapiens

<400> SEQUENCE: 142

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu

<210> SEQ ID NO 143
<211> LENGTH: 174
<212> TYPE: PRT
<213> ORGANISM: Homo sapiens

<400> SEQUENCE: 143

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
            20                  25                  30

Leu Gln His Gly Met Val Gly Pro Leu His Ser Ser Leu Ala Ala Ser
        35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Gln Pro His Leu Gly Val Ser Ser Ala Ala Ser Gly
            100                 105                 110

His Leu Gly Arg Ser Phe Leu Ser Gly Glu Pro Ser Gln Ala Asp Val
```

```
                115                 120                 125
Gln Pro Leu Gly Pro Ser Ser Leu Ala Val His Thr Ile Leu Pro Gln
        130                 135                 140

Glu Ser Pro Ala Leu Pro Thr Ser Leu Pro Ser Ser Leu Val Pro Pro
145                 150                 155                 160

Val Thr Ala Ala Gln Phe Leu Thr Pro Pro Ser Gln His Ser
                165                 170

<210> SEQ ID NO 144
<211> LENGTH: 297
<212> TYPE: PRT
<213> ORGANISM: Homo sapiens

<400> SEQUENCE: 144

Trp Leu Ser Arg Leu Gln Ser Gly Met Val Pro Asn Gln Tyr Asn Pro
1               5                   10                  15

Leu Arg Gly Ser Val Ala Pro Gly Pro Leu Ser Thr Gln Ala Pro Ser
                20                  25                  30

Leu Gln His Gly Met Val Gly Pro Leu His Ser Ser Leu Ala Ala Ser
            35                  40                  45

Ala Leu Ser Gln Met Met Ser Tyr Gln Gly Leu Pro Ser Thr Arg Leu
    50                  55                  60

Ala Thr Gln Pro His Leu Val Gln Thr Gln Gln Val Gln Pro Gln Asn
65                  70                  75                  80

Leu Gln Met Gln Gln Gln Asn Leu Gln Pro Ala Asn Ile Gln Gln Gln
                85                  90                  95

Gln Ser Leu Gln Pro Pro Pro Pro Gln Pro His Leu Gly Val
            100                 105                 110

Ser Ser Ala Ala Ser Gly His Leu Gly Arg Ser Phe Leu Ser Gly Glu
            115                 120                 125

Pro Ser Gln Ala Asp Val Gln Pro Leu Gly Pro Ser Ser Leu Ala Val
        130                 135                 140

His Thr Ile Leu Pro Gln Glu Ser Pro Ala Leu Pro Thr Ser Leu Pro
145                 150                 155                 160

Ser Ser Leu Val Pro Pro Val Thr Ala Ala Gln Phe Leu Thr Pro Pro
                165                 170                 175

Ser Gln His Ser Tyr Ser Ser Pro Val Asp Asn Thr Pro Ser His Gln
            180                 185                 190

Leu Gln Val Pro Glu His Pro Phe Leu Thr Pro Ser Pro Glu Ser Pro
        195                 200                 205

Asp Gln Trp Ser Ser Ser Pro His Pro Ala Phe Gln Arg Leu Arg
    210                 215                 220

Leu Val Arg Gly Arg Leu Gln Pro Ser His Gln His Ala Val Pro Asp
225                 230                 235                 240

Arg Pro His Ser Gly Gly Leu Gln Val Asn Gly Ala Pro His Glu Thr
                245                 250                 255

Pro Ala Ser Phe Pro Lys Pro Ser Gly Val Cys Val Arg Ser Val Asp
            260                 265                 270

Ala Arg Ala Asp Gln Arg Ser Leu Phe Lys Thr His Val Phe Ile Gln
        275                 280                 285

Asn Lys Asn Glu Asp Phe Asn Phe Phe
    290                 295

<210> SEQ ID NO 145
<211> LENGTH: 49
<212> TYPE: PRT
```

```
<213> ORGANISM: Homo sapiens

<400> SEQUENCE: 145

Ala Ala Gly Thr Leu Val Val Val Leu Met Pro Pro Glu Gln Leu
1               5                   10                  15

Arg Asn Ser Ser Phe His Phe Leu Ser Arg Glu Leu Ser Arg Val Leu
            20                  25                  30

His Thr Asn Val Val Phe Lys Arg Asp Ala His Gly Gln Gln Met Ile
        35                  40                  45

Phe

<210> SEQ ID NO 146
<211> LENGTH: 42
<212> TYPE: DNA
<213> ORGANISM: Homo sapiens

<400> SEQUENCE: 146
cccggttggg cagcctcaac atcccctaca agatcgaggc cg                          42

<210> SEQ ID NO 147
<211> LENGTH: 12
<212> TYPE: DNA
<213> ORGANISM: Homo sapiens

<400> SEQUENCE: 147
atcaatgccc cc                                                           12

<210> SEQ ID NO 148
<211> LENGTH: 17
<212> TYPE: DNA
<213> ORGANISM: Homo sapiens

<400> SEQUENCE: 148
gagcacacag gccccct                                                      17

<210> SEQ ID NO 149
<211> LENGTH: 14
<212> TYPE: DNA
<213> ORGANISM: Homo sapiens

<400> SEQUENCE: 149
ttaagtagag actt                                                         14

<210> SEQ ID NO 150
<211> LENGTH: 12
<212> TYPE: DNA
<213> ORGANISM: Homo sapiens

<400> SEQUENCE: 150
gggccgtgga cg                                                           12

<210> SEQ ID NO 151
<211> LENGTH: 15
<212> TYPE: DNA
<213> ORGANISM: Homo sapiens

<400> SEQUENCE: 151
gtggaggggg gatgg                                                        15

<210> SEQ ID NO 152
<211> LENGTH: 10
<212> TYPE: DNA
<213> ORGANISM: Homo sapiens
```

<400> SEQUENCE: 152
gtcccctgac                                                            10

<210> SEQ ID NO 153
<211> LENGTH: 10
<212> TYPE: DNA
<213> ORGANISM: Homo sapiens

<400> SEQUENCE: 153
tcctcacccc                                                            10

<210> SEQ ID NO 154
<211> LENGTH: 9
<212> TYPE: PRT
<213> ORGANISM: Homo sapiens

<400> SEQUENCE: 154

Gly Cys His Pro Arg Trp Ser His Pro
1               5

<210> SEQ ID NO 155
<211> LENGTH: 13
<212> TYPE: PRT
<213> ORGANISM: Homo sapiens

<400> SEQUENCE: 155

Pro Cys Pro Arg Arg Cys His Pro Arg Trp Ser His Pro
1               5                   10

<210> SEQ ID NO 156
<211> LENGTH: 37
<212> TYPE: PRT
<213> ORGANISM: Homo sapiens

<400> SEQUENCE: 156

Leu Ser Arg Asp Leu Cys Ser His Trp Ala Pro Ala Ala Trp Arg Cys
1               5                   10                  15

Thr Leu Phe Cys Pro Arg Arg Ala Pro Pro Cys Pro Arg Arg Cys His
            20                  25                  30

Pro Arg Trp Ser His
        35

<210> SEQ ID NO 157
<211> LENGTH: 34
<212> TYPE: PRT
<213> ORGANISM: Homo sapiens

<400> SEQUENCE: 157

Cys Cys Ser His Trp Ala Pro Ala Ala Trp Arg Cys Thr Leu Phe Cys
1               5                   10                  15

Pro Arg Arg Ala Pro Pro Cys Pro Arg Arg Cys His Pro Arg Trp Ser
            20                  25                  30

His Pro

<210> SEQ ID NO 158
<211> LENGTH: 38
<212> TYPE: PRT
<213> ORGANISM: Homo sapiens

<400> SEQUENCE: 158

Glu Gly Arg Gly Arg Cys Ser His Trp Ala Pro Ala Ala Trp Arg Cys
1               5                   10                  15

Thr Leu Phe Cys Pro Arg Arg Ala Pro Pro Cys Pro Arg Arg Cys His
            20                  25                  30

Pro Arg Trp Ser His Pro
            35

<210> SEQ ID NO 159
<211> LENGTH: 38
<212> TYPE: PRT
<213> ORGANISM: Homo sapiens

<400> SEQUENCE: 159

Gly Gly Gly Gly Met Gly Ser His Trp Ala Pro Ala Ala Trp Arg Cys
1               5                   10                  15

Thr Leu Phe Cys Pro Arg Arg Ala Pro Pro Cys Pro Arg Arg Cys His
            20                  25                  30

Pro Arg Trp Ser His Pro
            35

<210> SEQ ID NO 160
<211> LENGTH: 39
<212> TYPE: PRT
<213> ORGANISM: Homo sapiens

<400> SEQUENCE: 160

Glu Arg Ala Arg Gln Thr Cys Ser His Trp Ala Pro Ala Ala Trp Arg
1               5                   10                  15

Cys Thr Leu Phe Cys Pro Arg Arg Ala Pro Pro Cys Pro Arg Arg Cys
            20                  25                  30

His Pro Arg Trp Ser His Pro
            35

<210> SEQ ID NO 161
<211> LENGTH: 40
<212> TYPE: PRT
<213> ORGANISM: Homo sapiens

<400> SEQUENCE: 161

Arg Val Arg Ala Arg Gln Thr Cys Ser His Trp Ala Pro Ala Ala Trp
1               5                   10                  15

Arg Cys Thr Leu Phe Cys Pro Arg Arg Ala Pro Pro Cys Pro Arg Arg
            20                  25                  30

Cys His Pro Arg Trp Ser His Pro
            35                  40

<210> SEQ ID NO 162
<211> LENGTH: 12
<212> TYPE: PRT
<213> ORGANISM: Homo sapiens

<400> SEQUENCE: 162

Arg His His His His His Ser Arg Thr Leu Val Ala
1               5                   10

<210> SEQ ID NO 163
<211> LENGTH: 70
<212> TYPE: PRT
<213> ORGANISM: Homo sapiens

<400> SEQUENCE: 163

Asp Ser Gly Pro Ala Arg Pro Arg Ile Pro Thr Ser Pro Thr Gly Pro
1               5                   10                  15

-continued

```
Arg Ala Ser Pro Ala Leu Pro Pro Ala Cys Ser Pro Arg Ser Pro Ala
            20                  25                  30

Phe Arg Arg Pro Ser Ser Lys Arg Arg Ala Pro Arg Asp Pro Gly Phe
        35                  40                  45

Leu Ser Gln Ala Phe Gly Arg Leu Cys Ala Leu Cys Gly Cys Gln Gly
    50                  55                  60

Arg Pro Glu Glu Pro Ser
65                  70

<210> SEQ ID NO 164
<211> LENGTH: 12
<212> TYPE: PRT
<213> ORGANISM: Homo sapiens

<400> SEQUENCE: 164

Gly Arg Gln His Pro Gln Pro Pro Ala Thr Gly Ala
1               5                   10
```

NOTCH MUTATIONS LEADING TO INCREASED RECEPTOR SIGNALING

CROSS REFERENCE TO RELATED APPLICATIONS

The present application claims priority to, and the benefit of, U.S. provisional applications 60/598,546, filed on Aug. 4, 2004 and 60/672,053, filed on Apr. 18, 2005. The contents of these prior applications are hereby incorporated by reference in their entirety.

The present application is a continuation of U.S. application Ser. No. 11/194,913, filed on Aug. 2, 2005. U.S. Ser. No. 11/194,913 claims priority to and the benefit of U.S. provisional application 60/598,546, filed on Aug. 4, 2004 and U.S. provisional application 60/672,053, filed on Apr. 18, 2005. These previous applications are hereby incorporated by reference in their entirety.

STATEMENT OF GOVERNMENT FUNDING

The United States Government has a paid-up license in this invention and the right in limited circumstances to require the patent owner to license others under reasonable terms as provided for by the terms of NIH Grant No. R01CA082308, R01CA92433 and P01CA68484 awarded by the Department of Health and Human Services.

FIELD OF THE INVENTION

The present invention is directed to human NOTCH receptors that have undergone mutations resulting in either increased responsiveness to biological stimuli or constitutive activation independent of the need for other stimuli. The mutations occur in specific, well-defined regions of NOTCH receptors and are somatically acquired by cancer cells as part of the process of malignant transformation. The growth of these cancer cells can be slowed or stopped using agents that interfere with receptor signaling.

BACKGROUND OF THE INVENTION

NOTCH receptors 1-4 are transmembrane receptor proteins that signal through a pathway that relies on regulated proteolysis. Following ligand-binding, the receptor is sequentially: i) cleaved extracellularly by metalloproteases of the ADAM family (Brou, et al., *Mol. Cell.* 5:207-216 (2000); Mumm, et al. *Mol Cell* 5:197-206 (2000)); ii) mono-ubiquitinated on a lysine residue lying just internal to the transmembrane domain (Gupta-Rossi, et al., *J. Cell Biol.* 166:73-83 (2004)); iii) endocytosed (Gupta-Rossi, et al., *J. Cell Biol.* 166:73-83 (2004)), and iv) proteolytically cleaved by a gamma-secretase enzyme (De Strooper, et al., *Nature* 398:518-522 (1999)). This final step in the activation process permits the intracellular portion of NOTCH receptors to translocate to the cell nucleus where it interacts with transcription factors to alter gene activity. NOTCH receptor signaling appears to play an important role in the differentiation and proliferation of cells and in controlling apoptosis, three processes that are important with respect to neoplastic transformation (see U.S. Pat. No. 6,703,221).

The NOTCH-1 gene was discovered through its involvement in a (7; 9) chromosomal translocation found in fewer than 1% of T-cell acute lymphoblastic leukemias (T-ALLs) (Ellisen, et al., *Cell* 66:649-661 (1991)). NOTCH-1 is highly expressed in thymocytes (Ellisen, et al., *Cell* 66:649-661 (1991)), where it induces common lymphoid progenitors to adopt a T cell fate (Radtke, et al., *Immunity* 10:547-558). Subsequently, it promotes the assembly of pre-T cell receptor complexes which play a critical role in driving a proliferative burst that accompanies maturation of CD4−/CD8− thymocytes to the CD4+/CD8+ developmental stage (Wolfer, et al., *Immunity* 16:869-879 (2002)).

In its resting state, mature NOTCH-1 is a heterodimeric receptor comprised of a ligand-binding extracellular subunit (NEC) and a non-covalently associated transmembrane subunit (NTM) (Rand, et al., *Mol. Cell. Biol.* 20:1825-1835; Logeat, et al., *Proc. Natl. Acad. Sci. USA* 95:8108-8112 (1998)). NEC consists of a ligand-binding domain comprised of epidermal growth factor-like repeats, three iterated Lin 12/NOTCH repeats, and a conserved 103 amino acid sequence (hereafter termed HD, for heterodimerization domain) that is sufficient for association with the extracellular portion of NTM.

Physiologic activation of NOTCH receptors occurs when a ligand of the Delta-Serrate-Lag2 (DSL) family binds to the NEC subunit and initiates a cascade of successive proteolytic cleavages in the NTM subunit. The final cleavage, which is catalyzed by γ-secretase, a multiprotein complex containing presenilin-1 or -2, nicastrin, APH-1, and PEN-2 (Francis, et al., *Dev. Cell* 3:85-97 (2002); Kimberly, et al., *Proc. Natl. Acad. Sci. USA* 100:6382-6387 (2003)) releases the intracellular part of NTM (called intracellular NOTCH, or ICN) from the membrane, permitting it to translocate to the cell nucleus. There, it associates with the DNA-binding factor CSL and co-activators of the Mastermind family to form a short-lived transcriptional activation complex (Wallberg, et al., *Mol. Cell. Biol.* 22:7812-7819 (2002); Fryer, et al., *Genes Dev.* 16:1397-1411 (2002); Nam, et al., *J. Biol. Chem.* 278:21232-21239 (2003)) Degradation and turnover of the complex is apparently regulated by F-box factors of the SEL-10 family (Oberg, et al., *J. Biol. Chem.* 276:35847-35853 (2001)).

The (7; 9) translocation creates a NOTCH-T cell receptor β fusion gene that encodes N-terminally-deleted, constitutively active NOTCH-1 polypeptides similar to the ICN (Ellisen, et al., *Cell* 66:649-661 (1991); Aster, et al., *Cold Spring Harb. Symp. Quant. Biol.* 59:125-136 (1994); Das, et al., *J. Biol. Chem.*, epublished May 3, 2004)) and these truncated and constitutively active forms of NOTCH-1 induce T-ALL in mouse models (Aster, et al., *Mol. Cell. Biol.* 20:7505-7515 (2000)). NOTCH-1 is also the site of frequent retroviral insertions that cooperate with the E2A-PBX1 and cMYC transgenes in multistep pathways leading to the development of murine T-ALL (Hoemann, et al., *Mol. Cell. Biol.* 20:3831-3842 (2000); Feldman, et al., *Blood* 96:1906-1913 (2000)). Further, NOTCH inhibitors cause a $G_0/G_1$ cell cycle arrest in cell lines derived from human and murine NOTCH-1-associated T-ALLs, indicating that NOTCH signaling is required for the sustained growth of these leukemias (Weng, et al., *Mol. Cell. Biol.* 23:655-664 (2003)).

The (7; 9) translocation has only been associated with a very small percentage of patients having T-ALL. The identification of additional mutations associated with NOTCH-1 would have important implications for the pathogenesis of this type of cancer. Although mutations in NOTCH-2, NOTCH-3, and NOTCH-4 have not been identified in human cancer, it is known that abnormal increases in function of these NOTCH receptors in other mammals can cause T-ALL (NOTCH-2 and -3, Bellavia, et al., *Embo J.* 19:3337-3348 (2000); Rohn, *J. Virol.* 70:8071-8080 (1996); Weng, et al., *Mol. Cell. Biol.* 23:655-664)) and breast cancer (NOTCH-4, Callahan and Rafat, *J. Mammary Gland Biol Neoplasia* 6:23-36 (2001)). Identification of novel mutations in human tumors should be useful diagnostically in helping to identify the presence of cancer and in identifying cancer cells that respond to inhibitors of NOTCH signaling, thereby making it possible to direct rational cancer treatment with NOTCH signaling pathway inhibitors.

SUMMARY OF THE INVENTION

The present invention is based upon the discovery that mutations in two specific regions of the NOTCH-1 receptor lead to increased receptor signaling and are associated with uncontrolled cellular growth. The first is a region within the heterodimerization domain that is characterized by the presence of many amino acids that are highly conserved between species. The amino acids (residues 1571-1622 in SEQ ID NO:1, see FIGS. 1 and 3 for sequence identification numbers) are encoded by exon 26 and are found within the NEC subunit (i.e. the extracellular portion) of the NOTCH-1 protein. In intact NOTCH-1, they are non-covalently bound to amino acids encoded by exon 27 (amino acids 1674-1730) which lie on the NTM subunit (i.e., the transmembrane portion of the receptor). It is believed that mutations, especially non-conservative mutations, in these "hotspots" of the HD domain, i.e., 1571-1622 of the NEC subunit and 1674-1730 of the NTM subunit, destabilize the NOTCH-1 heterodimer. This leads to dissociation of NEC and successive metalloprotease cleavage, ubiquination, endocytosis, and cleavage by gamma-secretase, permitting nuclear translocation of the intracellular portion of NOTCH-1 and activation of target genes.

A second region involved by mutations that lead to uncontrolled cellular growth is the C-terminal portion of NOTCH-1 (amino acid 2311 to 2556), which includes the PEST region (amino acid 2423 to amino acid 2556). These mutations appear to reduce the rate at which the receptor is degraded intracellularly after activation, i.e., after it has been released due to gamma-secretase cleavage. As a result, the transcription of NOTCH-1-responsive genes continues for an inappropriately long period of time, again, leading to increased signaling and, ultimately, uncontrolled growth.

It has been discovered that mutations in the HD domain and in the PEST domain are often found in leukemic cell lines and in biological samples obtained from patients with T cell acute lymphoblastic leukemia (T-ALL). Uncontrolled growth in these cells may be arrested using agents that interfere with NOTCH signaling, such as gamma-secretase inhibitors. Overall, the experiments performed have led to the conclusion that there is a group of cancer cells that depend upon abnormal NOTCH activity to maintain uncontrolled growth and that mutations in the HD domain and in the PEST domain of NOTCH-1 may be used diagnostically to identify cancer cells likely to respond to gamma-secretase inhibitors or other factors that diminish NOTCH activity.

In its first aspect, the invention is directed to a substantially purified mutant NOTCH-1 receptor which has the amino acid sequence of wild type NOTCH-1, shown herein as SEQ ID NO:1, except for mutations within the hotspots of the HD domain. These mutations lead to increased receptor signaling relative to unmutated NOTCH-1, due to increased susceptibility to cleavage by gamma-secretase. The specific hotspot regions of SEQ ID NO:1 in which the mutations occur are amino acids 1571-1622 and/or amino acids 1674-1730.

As used herein, the term "substantially purified" means that the receptor protein (or the polynucleotide encoding the protein) has been separated from the biological components associated with NOTCH-1 as found in nature. Typically, a substantially pure protein (or polynucleotide) will comprise at least 85% of a sample, with greater percentages being preferred. Many means are available for assessing the purity of protein or nucleic acid samples, including analysis by electrophoresis, chromatography and analytical centrifugation. The term "unmutated NOTCH-1" refers to NOTCH-1 receptors having the sequence of SEQ ID NO:1 and to polynucleotides that encode receptors having this sequence. The term also includes allelic variations in these sequences that are normally found in cells and which are not associated with abnormal NOTCH-1 signaling or with abnormal, uncontrolled cellular growth.

In order to determine whether a mutation leads to increased gamma-secretase signaling, the assays described herein in the Examples section may be used. The most preferred method involves the use of cells transfected with a reporter gene, e.g., a polynucleotide encoding luciferase, that is under the control of a regulatory element turned on in response to NOTCH-1 signaling. Activation of the reporter gene upon exposure of cells to gamma-secretase can be readily measured and reflects NOTCH activity (see, e.g., Hsieh, et al., *Mol. Cell. Biol.* 16:952-959 (1996)).

Comparison of HD amino acid sequences from a variety of species has resulted in the identification of certain specific amino acid positions that are highly conserved in hotspots. Mutations in these positions, particularly non-conservative mutations, are particularly likely to destabilize the interaction between the NEC and NTM subunits of NOTCH-1. The term "non-conservative mutation" refers to a mutation in which wild type amino acids are replaced with amino acids having different chemical characteristics. Examples of a non-conservative substitution include the substitution of a proline for other amino acids within a well-structured protein domain (i.e., the HD domain), the substitution of a basic amino acid for a non-basic amino acid, the substitution of an acidic amino acid for a non-acidic amino acid, the substitution of a polar amino acid for a non-polar amino acid, etc. The distinction between conservative and non-conservative mutations is well recognized by those of skill in the art. Conserved amino acids in the HD domain where mutations are associated with increased NOTCH-1 signaling are found at positions: 1571; 1573; 1575; 1576; 1578; 1579; 1583; 1586; 1588; 1590; 1593; 1594; 1595; 1598; 1600-1607; 1610-1618; 1674; 1675; 1677; 1679-1684; 1686; 1695; 1696; 1703; 1706; 1715; 1720; 1725; and 1728. All of these positions are identified with reference to SEQ ID NO:1.

The invention includes specific mutations that are associated with the uncontrolled growth of cancer cells. With respect to the HD domain, this occurs in cases where amino acids 1571-1618 are replaced with a sequence selected from the group consisting of SEQ ID NO:12-SEQ ID NO:22, SEQ ID NO:102-118 or SEQ ID NO:145. Other mutations associated with the growth of cancer cells include the replacement of amino acids 1571-1622 with a sequence selected from the group consisting of SEQ ID NO:23-SEQ ID NO:29 or SEQ ID NO:119-127. Similarly, the sequence from amino acid 1674 to amino acid 1730 may be replaced with a sequence selected from the group consisting of SEQ ID NO:70-SEQ ID NO:75 or SEQ ID NO:128-137.

The inventors have also found that mutations in SEQ ID NO:1 occurring in the C-terminal portion of NOTCH-1, i.e., from amino acid 2311 to amino acid 2556, lead to increased NOTCH-1 signaling in response to exposure of cells to gamma-secretase. All of these mutations cause the appearance of a premature stop codon or a shift in the translational reading frame, and thus lead to the loss of some or all of the sequences corresponding to the PEST region (amino acid 2423 to 2556). It is believed that these mutations lead to a reduced rate at which receptor is degraded. Specific mutations include the replacement of the portion of SEQ ID NO:1 corresponding to amino acids 2311-2556 with a sequence selected from the group consisting of SEQ ID NO:30-SEQ ID NO:59 or SEQ ID NO:139-144.

Mutations in the HD domain and the PEST domain may occur independently of one another or may be present in a single NOTCH-1 receptor. For example, a substantially purified mutant NOTCH-1 receptor, may comprise or consist of the amino acid sequence of SEQ ID NO:1, but wherein:
 a) the receptor has at least one of the following mutations:
  i) the portion of said amino acid sequence of SEQ ID NO:1 from amino acid 1571 to amino acid 1618 is replaced with a sequence selected from the group consisting of SEQ ID NO:12-SEQ ID NO:22, SEQ ID NO:102-118, or SEQ ID NO:145;
  ii) the portion of the amino acid sequence of SEQ ID NO:1 from amino acid 1571 to amino acid 1622 is replaced with a sequence selected from the group consisting of SEQ ID NO:23-SEQ ID NO:29, SEQ ID NO:119-127;
  iii) the portion of the amino acid sequence of SEQ ID NO:1 from amino acid 1674 to amino acid 1730 is replaced with a sequence selected from the group consisting of SEQ ID NO:70-SEQ ID NO:75 or SEQ ID NO:128-137; and
 b) and, in addition, the receptor is further mutated such that the portion of the amino acid sequence of SEQ ID NO:1 from amino acid 2311 to amino acid 2556 is replaced with a sequence selected from the group consisting of SEQ ID NO:30-SEQ ID NO:59 or SEQ ID NO:138-144.

Alternatively, a substantially purified mutant NOTCH-1 receptor, may comprise or consist of the amino acid sequence of SEQ ID NO:1, but wherein:
 a) the amino acid sequence of SEQ ID NO:1 is mutated in one or more amino acid positions selected from the group consisting of: 1571; 1573; 1575; 1576; 1578; 1579; 1583; 1586; 1588; 1590; 1593; 1594; 1595; 1598; 1600-1607; 1610-1618; 1674; 1675; 1677; 1679-1684; 1686; 1695; 1696; 1703; 1706; 1715; 1720; 1725; and 1728; and
 b) the amino acid sequence of SEQ ID NO:1 is further mutated such that the portion of said amino acid sequence from amino acid 2311 to amino acid 2556 is replaced with a sequence selected from the group consisting of SEQ ID NO:30-SEQ ID NO:59.

When mutations are present in both the HD and PEST regions, this leads to receptors in which signaling in response to gamma-secretase is especially enhanced.

In another aspect, the invention includes polynucleotides that encode any of the mutant NOTCH-1 receptors described above. Nucleic acid sequences coding for the mutant receptors may be incorporated into a vector in which they are operably linked to a promoter. The term "operably linked" refers to genetic elements that are joined in a manner that enables them to carry out their normal functions. For example, a gene is operably linked to a promoter when its transcription is under the control of the promoter and the protein normally encoded by the gene is ultimately produced. The invention includes the vectors coding for the mutant receptors as well as host cells transformed with the vectors.

In another aspect, the invention is directed to methods of diagnostically testing a biological sample for the presence of cancer cells by assaying the sample for any of the mutant NOTCH-1 receptors described above. The term biological sample, as used herein includes all of the different types of samples commonly used in the art of medicine in making diagnoses. Thus, the term encompasses, biopsy samples of tissue or fluid, blood, plasma, serum, lymph, urine, etc. Depending on the type of cancer being considered, certain types of samples will be the ones predominantly used. For example, for leukemia, samples of blood, plasma, or serum would tend to be favored. The choice of appropriate samples for testing is routine in clinical medicine Also included are the same methods applied to the NOTCH-2, NOTCH-3 and NOTCH-4 receptors, which contain regions with high levels of identity to the regions with mutations described for NOTCH-1. The NOTCH-1, -2, -3 and -4 receptors are very highly related and likely perform very similar or identical functions in a variety of cell types, differing mainly in that different members of this receptor family are expressed and used preferentially by different tissues and cell types. Cancers arising in different tissues may thus acquire very similar types of mutations that affect any of the NOTCH-1, -2, -3 or -4 receptors with identical consequences in terms of promoting tumor cell growth, depending on which of the receptor subtypes are expressed by the tissues from which these cancers arise. Thus, in this application, unless otherwise indicated, the term "NOTCH" receptor will be used to refer to diagnostic applications applied collectively to each of the NOTCH-1, -2, -3, and -4 receptors.

The presence of mutant receptor may be detected either by assays directed at the protein or by assays directed at the gene encoding the protein. With respect to assays directed at genes, the preferred method of testing is to amplify either the full-length polynucleotide encoding a mutant NOTCH receptor, or a portion of this polynucleotide, using the polymerase chain reaction (PCR). Oligonucleotide primers that can be used for amplification are described in the Examples section, but one of skill in the art can readily identify other appropriate primers based upon sequence information included herewith and known in the art.

Alternatively, gene mutations may be detected by performing hybridizations using probes under conditions that permit hybrids to form with mutant, but not wild type, nucleic acid. Both the assays and the oligonucleotides used in the assays are encompassed by the invention. The oligonucleotides should be at least 15 bases in length and hybridization assays should be carried out under stringent conditions. As used herein, the term "stringent conditions" refers to hybridizations carried out at approximately 60-70° C. and at a low salt concentration (equivalent to, for example, 0.02-0.15 M NaCl).

Assays designed to detect the mutant protein per se may be carried out using antibodies that bind to mutant NOTCH receptors with at least a hundredfold greater affinity than to unmutated NOTCH receptors. These antibodies may be either monoclonal or polyclonal in nature and can be made by injecting an antibody-producing animal with peptides derived from regions of NOTCH receptor containing mutations. Antibodies made in this manner and which preferentially bind to mutant receptor are also a part of the invention.

The invention is also directed to methods for slowing or stopping the growth of cells with the mutant receptors described above by exposing the cells to an effective amount of an agent, such as a gamma-secretase inhibitor, that interferes with NOTCH receptor signaling. Examples of appropriate inhibitors include III-31-C, N-[N-(3,5-difluorophenacetyl)-L-alanyl]S-phenylglycine t-butyl ester) (DAPT), compound E, D-helical peptide 294, isocoumarins, BOC-Lys(Cbz)Ile-Leu-epoxide, and (Z-LL)$_2$-ketone (see Kornilova, et al., *J. Biol. Chem.* 278:16479-16473 (2003)). The term "effective amount" indicates a sufficient concentration of inhibitor or other agent to significantly reduce NOTCH-1 activity, for example, a sufficient amount to reduce activity by at least 20%. The presence of an effective amount of an agent that inhibits Notch receptor activity should also be reflected clinically. For example, the rate growth of cancer cells should be slowed to a significant extent (e.g., by at least 20%) relative to the rate of growth occurring prior to treatment.

Although gamma-secretase inhibitors have been found to be effective as therapeutics, other agents that inhibit NOTCH activity may also be used. The mutations described herein should cause several effects, including: i) increased metalloprotease cleavage; ii) increased mono-ubiquitination (an enzymatic step carried out by an E3 ligase); iii) increased endocytosis, iv) increased gamma-secretase cleavage (as already discussed); v) increased nuclear translocation; and vi) increased formation of a nuclear NOTCH transcriptional activation complex. Drugs that act at any of these steps should stop the growth of cancer cells. One agent, an inhibitor of the nuclear complex, a dominant negative form of a protein called mastermind-like-1, has been previously described and inhibits all four NOTCH receptor subtypes (Weng, et al., *Mol Cell Biol* 23:655-664 (2003)).

Also encompassed by the invention are methods of assaying a test compound for its ability to inhibit abnormal cellular growth induced by the presence of a mutated NOTCH receptor. This involves incubating the test compound with cells that express any of the mutant NOTCH-1 receptors described above. Such cells may either be isolated from a biological sample or created by transfecting a cell with an expression vector encoding the mutant receptor. The incubation is carried out in the presence of gamma-secretase and the amount of NOTCH receptor activity that occurs is determined. Any method for measuring receptor activity may be used, but the luciferase reporter gene assay described in Hsieh, et al. (*Mol. Cell. Biol.* 16:952-959 (1996)) is preferred. The results obtained are then compared with those from assays carried out under essentially the same conditions but in the absence of the test compound. A reduction in activity caused by the test compound suggests that it is a NOTCH receptor inhibitor and may be useful in limiting the growth of cells expressing the receptor. This can be confirmed directly by comparing the growth of such cells in the presence and the absence of increasing concentrations of the test compound.

In addition to being of value in assays designed to evaluate the ability of a test compound to inhibit NOTCH receptor activity, polynucleotides encoding mutant NOTCH receptors may serve as a source for probes that can be used in the hybridization assays discussed above and as controls in diagnostic assays. The mutant receptor protein can be used to generate antibodies specific for mutated forms of NOTCH and can serve as a control in immunoassays designed to either quantitate the amount of NOTCH receptor present in a sample or to distinguish between normal and mutated forms of receptor. Both the mutant proteins and the polynucleotides encoding the mutant proteins should also be of interest to researchers studying biological processes such as differentiation and apoptosis.

As discussed above the invention includes isolated nucleic acid molecules encoding mutant Notch-1 receptors. Such nucleic acid molecules may comprise a nucleotide sequence selected from the group consisting of:
 a) a sequence of nucleotides that encodes a mutant Notch-1 receptor comprising any of the mutant amino acid sequences described herein and wherein, except for the codons encoding the mutant amino acid(s), the nucleotide sequence is that of SEQ ID NO:76;
 b) a sequence of nucleotides that encodes a mutant Notch-1 receptor having any of the amino acid sequences described herein;
 c) a sequence of nucleotides degenerate with the mutant Notch-1 encoding sequence of (a) or (b).

In another aspect, the invention includes a method of determining the oncogenic potential of a biological sample by assaying the sample for the presence any of one or more mutant Notch-1 receptors as described herein. The presence of mutant receptors indicates increased oncogenic potential relative to a sample in which such mutant Notch-1 receptors are not present.

In addition, the invention includes a method for following the progress of a therapeutic regime designed to alleviate a condition characterized by abnormal expression of a mutant Notch-1 receptor comprising:
 a) assaying a sample from a subject to determine the level of mutant Notch-1 receptor (or nucleic acid encoding a mutant Notch-1 receptor) at a first time point;
 b) assaying the level of the same receptor (or nucleic acid) at a second time point; and
 c) comparing the level at the second time point to the level determined at the first time point. Decreasing levels of mutant protein or nucleic acid is an indication that a therapy is working. Increasing levels are an indication that a therapy is not working.

The invention also encompasses a method for determining regression, progression or onset of a pathological disorder characterized by dysfunctional Notch-1 signal transduction. The method involves incubating a sample obtained from a patient having or suspected of having the disorder with a complementary nucleic acid hybridization probe having a sequence of nucleotides that is substantially homologous to that encoding one or more mutant Notch-1 receptors as described herein. The probe should generally be designed to interact with nucleic acid encoding the mutant form of the receptor and not the normal form as shown in SEQ ID NO:1. Binding between the probe and any complimentary mRNA that may be present in the sample is used to indicate the regression, progression or onset of the pathological disorder in said patient. Alternatively, assays may be performed using antibody (preferably monoclonal antibody) specific for a mutant form of the receptor. As the level of mutant receptor or nucleic acid encoding mutant receptor increases the likelihood that the disorder is present or progressing also increases. Reduced or absent levels of mutant receptor or nucleic acid is an indication of disorder regression or absence.

BRIEF DESCRIPTION OF THE DRAWINGS

FIGS. 1A to 1G: Aligned Full length amino acid sequences of human NOTCH receptors. The sequences shown are: NOTCH-1 (SEQ ID NO:1); NOTCH-2 (SEQ ID NO:2); NOTCH-3 (SEQ ID NO:3); and NOTCH-4 (SEQ ID NO:4).

FIG. 3A-3G2. HD and PEST domain mutations in γ-secretase inhibitor-sensitive T-ALL cell lines and in primary human T-ALL samples. (3A) sequence conservation of the exon 26 HD domain mutational "hotspot" region among vertebrate NOTCH-1 receptors. Positions of recurrent mutations are in bold and italics. (3B) missense mutations and deletions identified in cell lines (underlined) and primary T-ALLs. One mutation SEQ ID NO:145, was associated with acute myelogenous leukemia. Mutation sites are in bold and italics. (3C) in-frame insertions in the HD domain identified in primary T-ALLs. (3D) PEST domain mutations. The amino acid sequences of mutated NOTCH-1 alleles in cell lines (underlined) and primary T-ALLs are shown. Stop codons are indicated by asterisks. (3E) Schematic representation of PEST domain mutations. The circles (white, primary T-ALLs; black, cell lines) correspond to the positions at which the NOTCH-1 polypeptide sequence terminates. Key: NEC, NOTCH-1 extracellular domain; LNR, Lin/NOTCH repeats; HD, heterodimerization domain; NTM, NOTCH transmembrane subunit; TM, transmembrane domain; ANK, ankyrin repeat domain; TAD, transcriptional activation domain. In (A-D), amino acid residues correspond to those of human pro-NOTCH-1. (3F) Western blot analysis of lysates from NOTCH-dependent T-ALL cell lines. Whole cell extracts were analyzed with a NOTCH-1 antibody raised against the intracellular transcriptional activation domain (Aster, et al., *Mol. Cell. Biol.* 20:7505-15). Positions of pro-NOTCH-1 and the normal NTM subunit are denoted. The lower panel is a longer exposure of the same blot that accentuates the presence of additional NOTCH-1 polypeptides of smaller size than the normal NTM polypeptide. Each lane was loaded with 25 μg of total protein. (3G) Sequence conservation and mutations in exon 27, encoding the HD domain of the NOTCH-1 TMT subunit. This subunit of NOTCH is noncovalently bound to exon 26, the HD domain of the NEC subunit. Mutation sites are in bold and italics. For TALL 04.36 the i in the sequence indicates the site of insertion of the 14 amino acids shown immediately below.

FIG. 5A to 5K: Full length human NOTCH-1 gene sequence (SEQ ID NO:76) and encoded amino acid sequence (SEQ ID NO:1).

FIG. 6A to 6C: Compilation of HD and PEST domain mutations.)

DETAILED DESCRIPTION OF THE INVENTION

Figure 2A:
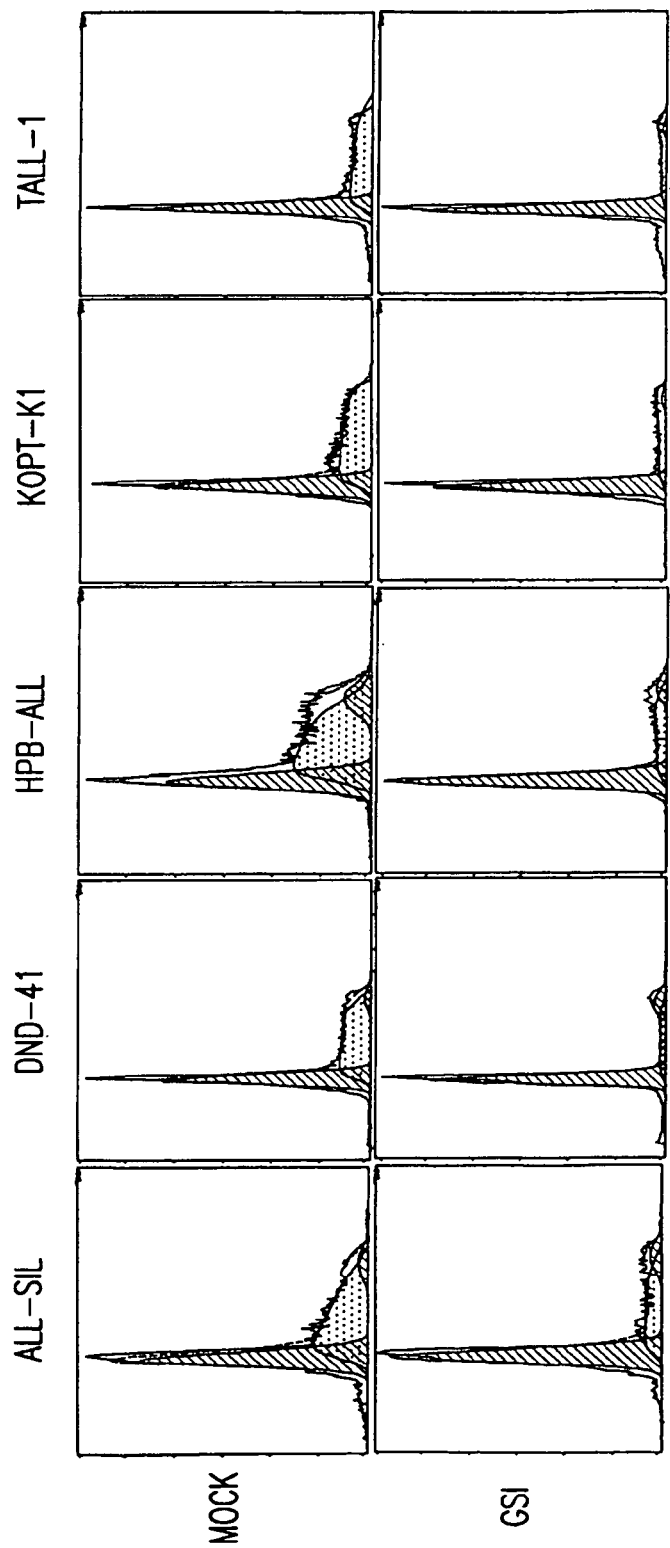
FIG. 2A-2C. Identification of T-ALL cell lines that require NOTCH signals for growth. (2A) Effect of the γ-secretase inhibitor compound E (GSI, 1 μM) or vehicle alone (mock) on the cell cycle distribution of sensitive cell lines. Cells were treated for 4-8 days, fixed in cold 70% ethanol, stained with propidium iodide, and analyzed by flow cytometry. Live cells were gated by forward/side scatter criteria. (2B) Rescue of GSI-induced cell cycle arrest by MSCV-GFP-ICN1 retrovirus. (2C) Induction of cell cycle arrest by dominant negative MSCV-GFP-Mastermind-like-1 retrovirus. In (2B) and (2C), control cultures were transduced with control empty MSCV-GFP retrovirus or the indicated test virus. Two days post-transduction, cultures were split in two and treated with either compound E (GSI) or DMSO vehicle (mock) for 7-10 days. Cultures were then harvested and stained with the DNA dye DRAQ5, which permits flow cytometric measurement of DNA content in unsorted GFP− and GFP+ subpopulations. A minimum of 15,000 events was collected to create each DNA content histogram.

The present invention is concerned with the identification of mutations in the human NOTCH-1 receptor that lead to an increase in receptor signaling. The mutations are associated with cancer cells that respond positively to treatment with agents that interfere with NOTCH-1 activation, such as gamma-secretase inhibitors and are located within two specific regions of the NOTCH-1 protein, the HD domain and the PEST domain. It is expected that analogous mutations in corresponding regions of NOTCH-2, NOTCH-3 and NOTCH-4 receptor subtypes should also lead to increased signaling and abnormal growth.

Assays designed to detect the presence of NOTCH-1 mutations, e.g., assays based upon PCR amplification, may be used diagnostically to identify tissue samples with cells in which abnormal NOTCH-1 receptor signaling is occurring and which are, as a result, more likely to exhibit uncontrolled growth. Cancers characterized by this particular abnormality should be amenable to treatment with agents that reduce NOTCH-1 signaling, such as gamma-secretase inhibitors. Any of the inhibitors described herein or which have been described in the art (for example, in connection with potential use in the treatment of Alzheimer's disease) may be used in treatment regimens. The diagnostic assays and therapeutic methods may be applied to other types of cancer besides T-ALL. Such cancers include but are not limited to: carcinomas of the breast, prostate, lung, pancreas, ovary, colon, bladder, kidney and GI tract, B cell leukemias, B and T cell lymphomas, Hodgkin's lymphoma, acute myelogenous leukemias, melanomas, neuroblastomas, medulloblastomas, glioblastoma multiforme and other glial cancers of the brain, and mesotheliomas.

I. Production of Polynucleotides Encoding Mutant NOTCH-1 Receptors

The full length amino acid sequence of human NOTCH-1 is shown in FIG. 1 and has been given the sequence identification number SEQ ID NO:1. This is the normal, unmutated form of receptor. Mutations in the HD domain and PEST domain that have been associated with samples from cancer patients or cancer cell lines are shown in FIG. 3. It should be noted that certain positions in the hotspots of the HD domain are highly conserved among different species (see FIG. 3A) and are especially sensitive to mutations that lead to increased gamma-secretase-generated activity.

Many methods are available for producing polynucleotides that encode NOTCH-1 receptors having the mutated sequences shown herein (see, e.g., Sambrook, et al., *Molecular Cloning: A Laboratory Manual*, $2^{nd}$ ed., Cold Spring Harbor Press (1989)). For example, a cDNA library prepared by reverse transcribing mRNA isolated from cells that express the mutant NOTCH gene may be screened using probes synthesized based upon the sequences shown in FIG. 1. Alternatively, the desired sequences may be obtained by PCR amplifying reverse transcribed RNA. Primers for PCR may be constructed using the sequences shown herein and specific oligonucleotides that have been found to be suitable for amplification are described in the Examples section. Confirmation that the correct sequence has been amplified and identification of the presence of specific mutations may be obtained by sequencing amplification products.

Alternatively, nucleic acids may be produced using standard chemical synthetic methods well known in the art. Once obtained, the polynucleotides can be used in recombinant methods for making receptor protein, expressed in cells for the purpose of screening for potential therapeutic agents, or used as controls in diagnostic assays.

II. Production of Mutant Receptor Protein

NOTCH-1 receptor protein can be synthesized using chemical methods or produced using the polynucleotides described above. In the latter case, the DNA sequence encoding the mutant receptor may be placed in a vector containing transcriptional and translational signals recognizable by an appropriate host. The cloned receptor sequences, in double-stranded form, are inserted into the expression vector in an operable linkage. Appropriate vectors and techniques for cloning and expressing receptor are well known in the art of molecular biology.

Expression vectors may be introduced into host cells, preferably mammalian host cells, by methods such as calcium phosphate precipitation, microinjection, electroporation or viral transfer. Cells expressing the recombinant mutant receptor can be selected using standard, well established methods. One simple method for confirming the presence of the mutant receptor nucleic acid in cells is to perform PCR amplification using primers known to flank the receptor-encoding nucleotide sequence. The presence of receptor may also be confirmed using functional assays of NOTCH-1 such as the luciferase assay described in the Examples section and in the art (see, Hsieh, et al., *Mol. Cell. Biol.* 16:952-959 (1996)). Once cells producing recombinant mutant NOTCH-1 receptor have been identified, they may be used in assays designed to identify agents capable of reducing signaling, for example, by incubation with gamma-secretase, or in assays that measure the ability of NOTCH-1 inhibitors to arrest uncontrolled cellular growth. The NOTCH-1 receptor itself may be used in diagnostic assays or to generate antibodies specific for mutant receptor that can be used in such assays.

III. Antibodies to Mutant NOTCH Receptor

The present invention encompasses antibodies that bind specifically to mutant forms of NOTCH receptors and processes for producing such antibodies. Antibodies that "bind specifically to mutant NOTCH receptors" are defined as those that have at least a hundredfold greater affinity for the mutant form of the receptor than for the unmutated form. The process for producing such antibodies may involve either injecting the full length mutant receptor protein into an appropriate animal or, preferably, injecting short peptides that include regions where mutations occur. The peptides should be at least five amino acids in length and may be injected either individually or in combinations.

Methods for making and selecting antibodies are well known to those of skill in the art as evidenced by standard reference works such as Harlow, et al., *Antibodies, A Laboratory Manual*, Cold Spring Harbor Laboratory, N.Y. (1988); Klein, *Immunology: The Science of Self-Nonself Discrimination* (1982); Kennett, et al., *Monoclonal Antibodies and Hybridomas: A New Dimension in Biological Analyses* (1980); and Campbell, "Monoclonal Antibody Technology," in: *Laboratory Techniques in Biochemistry and Molecular Biology* (1984).

The term "antibody," as used herein, is meant to include intact molecules as well as fragments that retain their ability to bind antigen such as Fab and F(ab')$_2$ fragments. The term "antibody" is also defined as referring to both monoclonal antibodies and polyclonal antibodies. Polyclonal antibodies are derived from the sera of animals immunized with an appropriate antigen. Monoclonal antibodies can be prepared using hybridoma technology as taught by references such as: Hammerling, et al., in *Monoclonal Antibodies and T-Cell Hybridomas*, Elsevier, N.Y., pp. 563-681 (1981). In general, this technology involves immunizing an immunocompetent animal, typically a mouse, with either intact protein or a fragment derived therefrom. Splenocytes are then extracted from the immunized animal and are fused with suitable myeloma cells, such as SP$_2$O cells. Thereafter, the resulting hybridoma cells are selectively maintained in HAT medium and then cloned by limiting dilution (Wands, et al., *Gastroenterology* 80:225-232 (1981)). The cells obtained through such selection may then be assayed to identify clones that secrete antibodies binding preferentially to mutant forms of NOTCH-1 or mutant forms of other NOTCH receptors.

The antibodies, or fragments of antibodies, of the present invention may be used to detect the presence of mutant NOTCH receptor proteins using a variety of immunoassays. For example, the antibodies may be used in radioimmunoassays or immunometric assays, also known as "two site" or "sandwich" assays (see Chard, "An Introduction to Radioimmune Assay and Related Techniques" in: *Laboratory Techniques in Biochemistry and Molecular Biology*, North Holland Publishing Co., N.Y. (1978)). In a typical immunometric assay, a quantity of unlabeled antibody is bound to a solid support that is insoluble in the fluid being tested, e.g., blood, lymph, cellular extracts, etc. After the initial binding of antigen to immobilized antibody, a quantity of detectably labeled second antibody (which may or may not be the same as the first) is added to permit detection and/or quantitation of bound antigen (see, e.g., Kirkham, et al., *Radioimmune Assay Methods*, pp. 199-206 (1970)). Many variations of these types of assays are known in the art and may be employed for the detection of mutant NOTCH receptors.

Antibodies to mutant NOTCH receptors may also be used in the purification of either the intact receptor or fragments of these receptors (see generally, Dean, et al., *Affinity Chromatograph, A Practical Approach*, IRLP Press (1986)). Typically, antibody is immobilized on a chromatographic matrix such as Sepharose 4B. The matrix is then packed into a column and a preparation containing mutant receptor is passed through the column under conditions that promote binding, e.g., under conditions of low salt. The column is then washed and bound receptor is eluted using a buffer that promotes dissociation from antibody (e.g., a buffer having an altered pH or salt concentration). The eluted receptor protein may be transferred into a buffer of choice, e.g., by dialysis and either stored or used directly. Purified receptor may be used in the immunoassays described above or for the generation of antibodies for use in assays.

IV. Assay Methods

Diagnostic assays for determining whether a biological sample contains cancer cells in which the mutations described herein contribute to uncontrolled growth may be performed either using the immunoassays described above to analyze protein or, preferably, by assaying a sample for the presence of nucleic acid sequences encoding a mutant form of receptor. The preferred method for nucleic acid analysis is by PCR amplifying polynucleic acid that has been extracted from cells using methods well known in the art. Amplification may be performed using the oligonucleotide primers described in the Examples section below or using other oligonucleotides based upon the sequence of NOTCH-1 shown as SEQ ID NO:1. The amplified NOTCH receptor product may then be sequenced to determine whether it carries a mutation leading to increased signaling.

Alternatively, hybridizations may be performed under stringent conditions using probes that bind only to mutant sequences. The probes should be a minimum of 15 nucleotides in length and must cover the portion of the polynucleotide sequence that encodes the mutated region of NOTCH-1. Stringent conditions would typically involve hybridization at a temperature of 60-70° C. with a low salt concentration (e.g., 0.02 M to 0.15 M NaCl). Procedures for identifying and labeling probes as well as for carrying out hybridizations and analyzing results are well known in the art of molecular biology.

Host cells transformed with vectors encoding recombinant mutant NOTCH receptors may also be used in assays designed to identify test compounds that reduce inappropriate signaling by the receptor. The assays will typically involve incubating cells in the presence of gamma-secretase and test compound. NOTCH receptor signaling can then be quantitated using assays such as those described herein or using other assays that are known in the art (see also, Hsieh, et al., *Mol. Cell. Biol.* 16:952-959 (1996)). As a simple alternative, cells known to be expressing mutated forms of NOTCH-1 that lead to uncontrolled growth may be cultured in the presence and absence of gamma-secretase and test compound to determine the extent to which the compound is capable of arresting growth.

V. Treatment Methods

Gamma-secretase inhibitors have been developed by pharmaceutical companies interested in their potential use as a treatment for Alzheimer's disease. These same inhibitors can be used to treat cancer cells in cases in which uncontrolled growth is associated with the NOTCH receptor mutations described herein.

The therapeutic regimen involves first testing a biological sample containing cancer cells removed from a patient to determine whether a mutated form of a NOTCH receptor is present. Patients whose samples evidence the presence of mutations would then be treated using a gamma-secretase inhibitor or another agent that interferes with NOTCH receptor activity. The dosage administered will depend upon the particular condition being treated, the route of administration and clinical considerations that are well known in the art. Dosages can be gradually increased until a beneficial effect, e.g., a slowing of tumor growth, is detected. Agents may be provided in either single or multiple dosage regimens and may be given either alone or in conjunction with other therapeutic agents.

Treatment of mutant NOTCH receptor-associated cancers is compatible with any route of administration and dosage form. Depending upon the particular condition being treated, certain dosage forms will tend to be more convenient or effective than others. For example, topical administration may be preferred in treating skin cancers, whereas parenteral administration might be preferred for leukemias. Apart from parenteral and topical preparations, agents may be administered orally, perorally, internally, intranasally, rectally, vaginally, lingually and transdermally. Specific dosage forms include tablets, pills, capsules, powders, aerosols, suppositories, skin patches, parenterals and oral liquids including suspensions, solutions and emulsions. Sustained release dosage forms may also be used. All dosage forms may be prepared using methods that are standard in the art (see, e.g., *Remington's Pharmaceutical Sciences*, 16$^{th}$ ed., Easton, Pa. (1980)).

EXAMPLES

The present example provides results suggesting that approximately 65% of human T cell acute lymphoblastic leukemias (T-ALLs), including tumors from all major molecular oncogenic subtypes and those occurring in children and adults, have NOTCH-1 mutations. Most of these mutations occur in regions encoding an extracellular heterodimerization domain and as truncations removing a C-terminal PEST destruction box. The mutations cause increased NOTCH-1 signaling, and T-ALL cell lines bearing such mutations are growth arrested by NOTCH-1 pathway inhibitors.

Introduction

T cell acute lymphoblastic leukemia (T-ALL) is an aggressive neoplasm that preferentially affects children and adolescents. It is commonly associated with acquired chromosomal translocations and other genetic or epigenetic abnormalities, which lead to aberrant expression of a select group of transcription factors, including the helix-loop-helix proteins TAL1, TAL2, LYL1, and BHLHB1, the orphan homeobox proteins HOX11 and HOX11L2, and the fusion proteins MLL-ENL and CALM-AF10. Mis-expression of these proteins, alone or in combination, perturbs normal pathways of T cell development, growth, and survival, and defines subgroups of T-ALL with distinct gene expression profiles. Nevertheless, enforced expression of any one of these proteins alone in murine models is not sufficient to cause T-ALL, emphasizing the multistep molecular pathogenesis of this disease.

Materials and Methods

Cell Lines

All T-ALL cell lines were cultured in RPMI (Invitrogen) supplemented with 10% fetal bovine serum (Hyclone), 1 mM sodium pyruvate, 2 mM L-glutamine, 100 U/ml penicillin G, and 100 μ/ml streptomycin at 37° C. under 5% $CO_2$. U2OS cells were grown in Dulbecco's modified Eagle's medium (DMEM) supplemented with 10% fetal bovine serum (Hyclone), 2 mM L-glutamine, 100 U/ml penicillin G, and 100 μ/ml streptomycin at 37° C. under 5% $CO_2$.

Gamma-Secretase Inhibitor Treatment of Cell Lines

Gamma-secretase activity was inhibited by addition of compound E to growing cells to a final concentration of 1μ/M. Mock-treated cultures were exposed to vehicle only, DMSO at a final concentration of 0.01%. The following human T-ALL cell lines were tested for sensitivity to compound E: T-ALL-1, ALL-SIL, KOPT-K1, HPB-ALL, DND-41, CCRF-HSB2, RPMI8402, THP-6, BE-13, JM-Jurkat, Jurkat-E6, REX, CEM, LOUCY, DU-528, KE-37, SKW-3, MKB-1, MOLT-3, MOLT-4, MOLT-13, MOLT-15, MOLT-16, SUPT-7, SUPT-11, SUPT-13, P12-Ichikawa, KARPAS-45, DSMZ-PEER and PF-382. The murine cell line T-6E, which was derived from a T-ALL induced with a membrane-tethered form of truncated NOTCH-1 that requires gamma-secretase cleavage for activation, was used as a positive control.

Retroviruses

Construction of retroviral expression plasmids (MSCV-GFP-ICN1 and MSCV-dominant negative Mastermind-like-1-GFP), production of high-titer pseudotyped, amphotropic, replication-defective retroviruses and spinoculation procedure were performed as described previously (Weng, et al., *Mol. Cell. Biol.* 23:655-664).

Cell Cycle Analysis

Cells were stained with either propidium iodide after overnight fixation in cold 70% ethanol, or DRAQ5 (Biostatus, Leicester, UK) in complete medium (as suggested by the manufacturer) in instances where GFP fluorescence and DNA content measurement were measured simultaneously. DNA content was ascertained by flow cytometry and cell cycle factors determined using multicycle software (Phoenix Flow Systems, San Diego).

NOTCH-1 Expression Plasmids

NOTCH-1 expression plasmids in pcDNA3 have been described previously. To create a generic PEST deletion, the insertion mutation in the PEST domain of the T-ALL cell line ALL-SIL was amplified by PCR, identified by sequencing, and then sub-cloned into pcDNA3-NOTCH-1. Site-directed mutagenesis of the HD domain was conducted using the QuikChange kit (Stratagene). Mutagenic PCR primers were designed using the Stratagene web tool.

Receptor Gene Assays

NOTCH-1 expression plasmids (pcDNA3) were transiently transfected with U2OS cells with (i) an artificial luciferase reporter gene under the control of a promoter containing CSL binding sites and (ii) an internal Renilla luciferase control gene, as described previously (Aster, et al., *Mol. Cell. Biol.* 20:7505-7515 (2000)), using Lipofectamine Plus (Invitrogen). Total DNA was kept constant by adding empty vector as needed. All transfections were carried out in triplicate, and each experiment was repeated at least three times. Cell lysates were harvested 44-48 hours post-transfection and luciferase assays were carried out using the Dual Luciferase Assay System (Promega) on a Turner Systems luminometer, as per the manufacturer's suggestions.

PCR Amplification of NOTCH-1 cDNAs

RNA isolated from T-ALL cell lines (1) μ/g was reverse transcribed into cDNA using oligo-dT priming and Superscript reverse transcriptase (Invitrogen) in 20 μl reactions per the manufacturer's suggested conditions. PCR amplifications were performed using 1 μl of cDNA as template, 20 pMol of 5'-TTTGAATTCGGGCTGGACTGTGCGGAGCA TGTACCCGA (SEQ ID NO:78) and 5'-TTTGGATCCT-CGGAATGCGGGCGATCTG GGACTGCA (SEQ ID NO:79) NOTCH-1-specific primers, 0.25 μl of Ex-Taq Takara, Japan), 1× reaction buffer, 1×dNTPs and 7.5% DMSO in a 50 μl reaction volume. Cycle parameters were: 94° C. for three minutes; 30 cycles of 94° C. for one minute; 60° C. for thirty seconds; 72° C. for two minutes; and 72° C. for eight minutes. PCR products were purified on Qiagen columns, digested with Bam HI and Eco RI, ligated into pSP72 and used to transform DH5 alpha cells. Miniprep DNA from individual colonies was sequenced using T7 and SP6 primers.

Patient Material

Samples of cryopreserved lymphoblasts from 96 children and young adults with T-ALL treated at St. Jude Children's Research Hospital and Dana Farber Cancer Institute were obtained with informed consent at the time of diagnosis. Genomic DNA from each sample was extracted with a commercial kit (GENTRA) following the manufacturer's instructions. RNA was prepared from cryopreserved lymphoblasts with RNAaqueous reagents (Ambion) according to the manufacturer's instructions.

Quantitative RT-PCR

Quantitative RT-PCR analysis of HOX11, HOX11L2, TAL1, LYL1, TAL2 and BHLHB1 was performed as previously described (Ferrando, et al., *Cancer Cell* 1:75-87; Ferrando, et al., *Lancet* 363:535-536) using an ABI PRISM 7700 Sequence Detection System instrument (Perkin Elmer Applied Biosystems). RT-PCR-based detection of MLL-ENL and CALM-AF10 fusion transcripts was also performed as previously described (Ferrando, et al., *Lancet* 363:535-536; Asnafi, et al., *Blood* 102:1000-1006).

Genomic DNA Preparation

Genomic DNA was prepared from primary T-ALLs by extraction with a commercial kit (GENTRA) following the manufacturer's instructions. DNA was prepared from cell lines by SDS lysis/proteinase K digestion, followed by phenol:chloroform extraction and ethanol precipitation. DNAs were resuspended in TE buffer, spectrophotometrically quantified and stored at −20° C.

Mutation Detection

Mutation detection in exons 26, 27, and 34 of NOTCH-1 was performed via PCR-based denaturing HPLC using a WAVE DNA fragment analysis system (Transgenomic) equipped with a DNASep HT cartridge. Amplicons for mutation analysis were prepared with the following primer combinations. The N-terminal region of the HD domain of NOTCH-1, encoded in exon 26 was divided into two amplicons. Amplicon HD-N1 was amplified by PCR using primers HD-N1FW1: 5'-AGCCCCCTGTACGACCAGTA (SEQ ID NO:80), HD-N1RV1: 5'-CTTGCGCAGCTCCTCCTC (SEQ ID NO:81), and by nested PCR using primers HD-N1FW2: 5'-GACCAGTACTGCAAGGACCA (SEQ ID NO:82), HD-N1RV2: 5'-TCCTCGCGGCCGTAGTAG (SEQ ID NO:83). Amplicon HD2 was amplified by PCR using primers HD-N2FW1: 5'-GTGCTGCACACCAACGTG (SEQ ID NO:84), HD-N2RV1: 5'-GAGGGCCCAGGAGAGTTG (SEQ ID NO:85), and by nested PCR using primers HD-N2FW2: 5'-GCACACGGCCAGCAGATGAT (SEQ ID NO:86), and HD-N2RV2: 5'-CGCCGGGTCTCACTCAC (SEQ ID NO:87).

The C terminal region of the HD domain of NOTCH 1, encoded in exon 27, was amplified by PCR using primers HD-CFW1: GTGGCGTCATGGGCCTCA (SEQ ID NO:88) and HD-CRV1: TAGCAACTGGCACAAACAGC (SEQ ID NO:89), and by nested PCR using primers HD-CFW2: CATGGGCCTCAGTGTCCT (SEQ ID NO:90) and HD-CRV2: GCACAAACAGCCAGCGTGTC (SEQ ID NO:91).

Sequences of exon 34 encoding the PEST domain and the continuous N-region containing the TAD of NOTCH-1 were divided into three amplicons. Amplicon PEST1 and PEST2 were amplified by PCR using primers PESTFW1: 5'-GCAG-CATGGCATGGTAGG (SEQ ID NO:92), and PESTRV1: 5'-AACATGTGTTTTAAAAAGGCTCCTC (SEQ ID NO:93), and by nested PCR using primers PEST1FW: 5'-AAACATCCAGCAGCAGC AAA (SEQ ID NO:94), PEST1RV: 5'-CACAGGCGAGGAGTAGCTGTG (SEQ ID NO:95), and PEST2FW: 5'-GTGACCGCAGCCCAGTTC (SEQ ID NO:96), and PEST2RV: 5'-AAAGGAAGC-CGGGGTCTC (SEQ ID NO:97). Amplicon TAD1 was amplified by PCR using primers TAD1FW1: 5'-AGACTG-GCCCACCTCGTCTCT (SEQ ID NO:98), TAD1RV1: 5'-GCTCTCCACTCAGGAAGCTC (SEQ ID NO:99), and by nested PCR using primers TAD1FW2: 5'-CGTCTCTC-CCACCTGCCTGT (SEQ ID NO:100), and TAD1RV2: 5'-CTGAGCTCACGCCAAGGT (SEQ ID NO:101). Before DHPLC analysis, nested PCR products were denatured at 95° C. for five minutes and slowly ramped to 40° C. using a Peltier Thermal Cycler (MJ Research, PTC-225) in order to allow the formation of homo- and hetero-duplexes in samples heterozygous for a mutant allele.

Fifteen to 30 microliters of annealed PCR fragments per sample were injected on to the DNASep HT cartridge for analysis. Products were eluted at a constant flow rate of 1.5 ml/min with a linear acetonitrile gradient determined by Navigator software (Transgenomic) based on the size and GC-content of the amplicon. The gradient was produced by combining 0.1 m trimethylammonium acetate (TEAA) buffer (pH 7) (Transgenomic) and Buffer B (0.1 m TEAA with 25% acetonitrile). The elution profiles of DNA fragments, monitored by the system's UV detector, were used to produce chromatographs. The analysis sequence for each sample was as follows: a 1.9-minute time lapse for the detector, a 0.1-minute loading stage with a 3% decrease in Buffer B, a 2.0-minute linear gradient with an increasing slope of 2% Buffer B per minute, a 0.1-minute cleaning stage using 75% acetonitrile, and a 0.1-minute equilibration before the next injection. Homo- and hetero-duplex peaks were detected between the initial injection peak, produced by residual nucleotides and primers in the reaction, and the wash stage.

Melting profiles for the nested PCR products, ranging from 276 to 452 based pairs, were constructed using the Navigator software. Appropriate partial denaturing temperatures for mutation detection, which produced percent helicities between 30% and 98% at each base contained in regions of interest, were predicted for all amplicons: PEST1, 66.5° C.;

PEST2, 65.0° C.; HD1, 67.0° C. and 64.5° C.; HD2, 67.0° C. and 64.0° C.; and TAD1, 64.5° C. and 63.9° C. Less stable heteroduplexes denature earlier than homoduplexes and, thus, appear first in elution profiles. Therefore, direct sequencing was performed on samples with chromatographs displaying species that eluted before normal homoduplexes.

Results

Figure 2B:
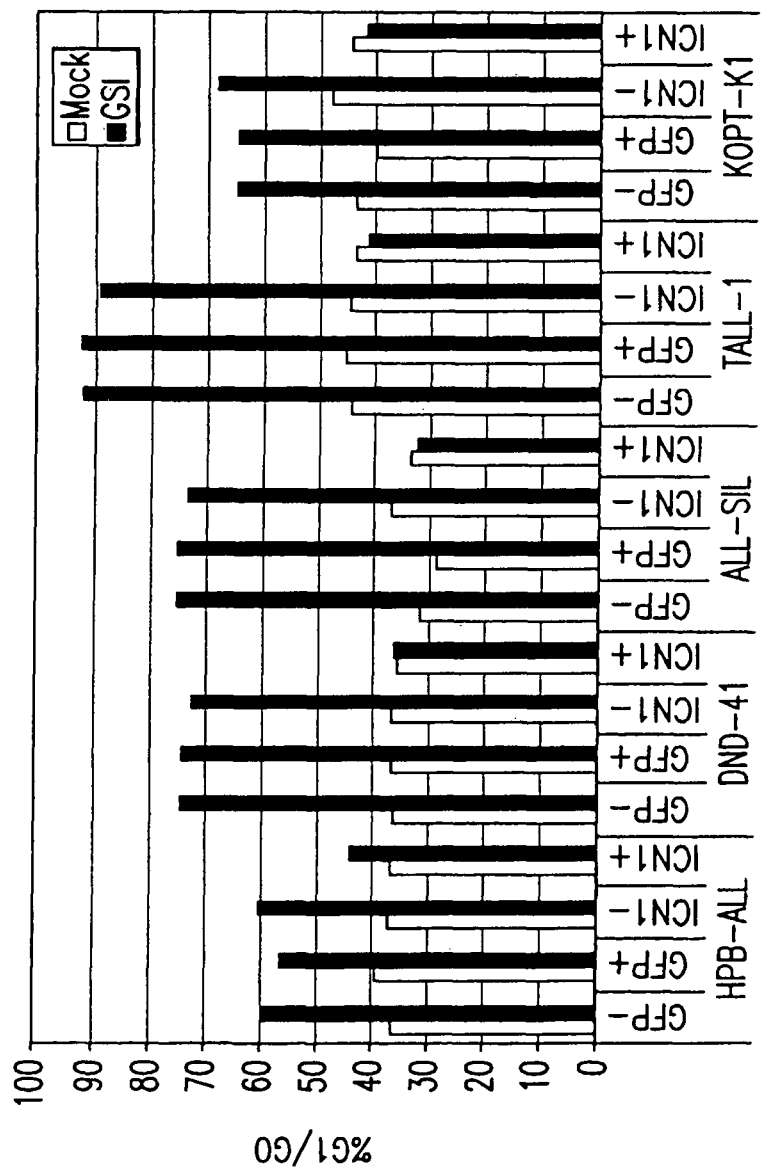
Figure 2C:
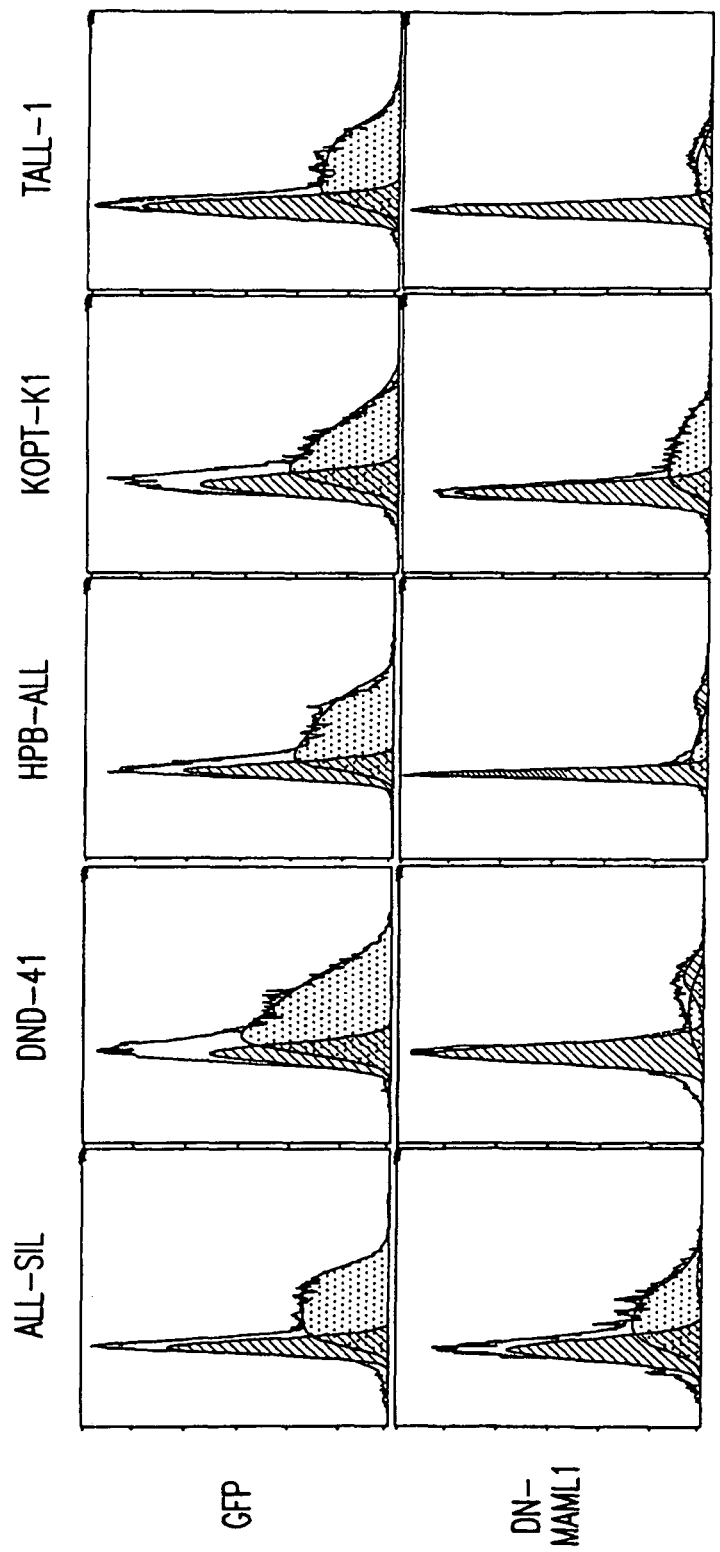

To evaluate the possible role of NOTCH-1 signaling in human T-ALL beyond the rare cases associated with the t(7; 9), we first tested T-ALL cell lines lacking the t(7; 9) for NOTCH dependency by treating these cells with a γ-secretase inhibitor (Weng, et al., *Mol. Cell. Biol.* 23:655-64). We observed that five of thirty human T-ALL cell lines tested showed a $G_0/G_1$ cell cycle arrest, which equaled or exceeded that of the T6E cell line, a reference NOTCH-1-dependent murine T-ALL (FIG. 2A). The growth suppression caused by gamma-secretase inhibitor was abrogated by retroviral expression of ICN1 (FIG. 2B), which is the fragment released after γ-secretase cleavage, and reproduced by retroviral expression of dominant negative Mastermind-like-1 (FIG. 2C). Taken together, these results indicated that the growth of these five cell lines depends on NOTCH-mediated signals.

Because NOTCH receptors can be activated by physical dissociation of the NOTCH extracellular domain (Rand et al., *Mol. Cell. Biol.* 20:1825-35; Kramer, Sci. STKE 2000, PE1), we reasoned that a newly identified HD domain of NOTCH-1 could be the site of gain-of-function mutations. One class of retroviral insertion observed in murine T-ALL causes deletion of the negative regulatory C-terminal PEST sequences (Hoemann, et al., *Mol. Cell. Biol.* 20:3831-42; Feldman, et al., *Blood* 96:1906-13), making this a second candidate region for oncogenic NOTCH-1 mutations. Remarkably, DNA sequencing of these genomic regions revealed both HD domain and PEST domain mutations in 4 of the 5 NOTCH-dependent cell lines. Missense mutations affecting the HD domain (encoded by exon 26 of NOTCH-1) involved residues that are invariant in vertebrate NOTCH-1 receptors, and caused non-conservative changes in amino acid residues (FIG. 3A-C). One cell line, DND-41, had two different HD domain mutations within the same NOTCH-1 allele.

Figure 3E:
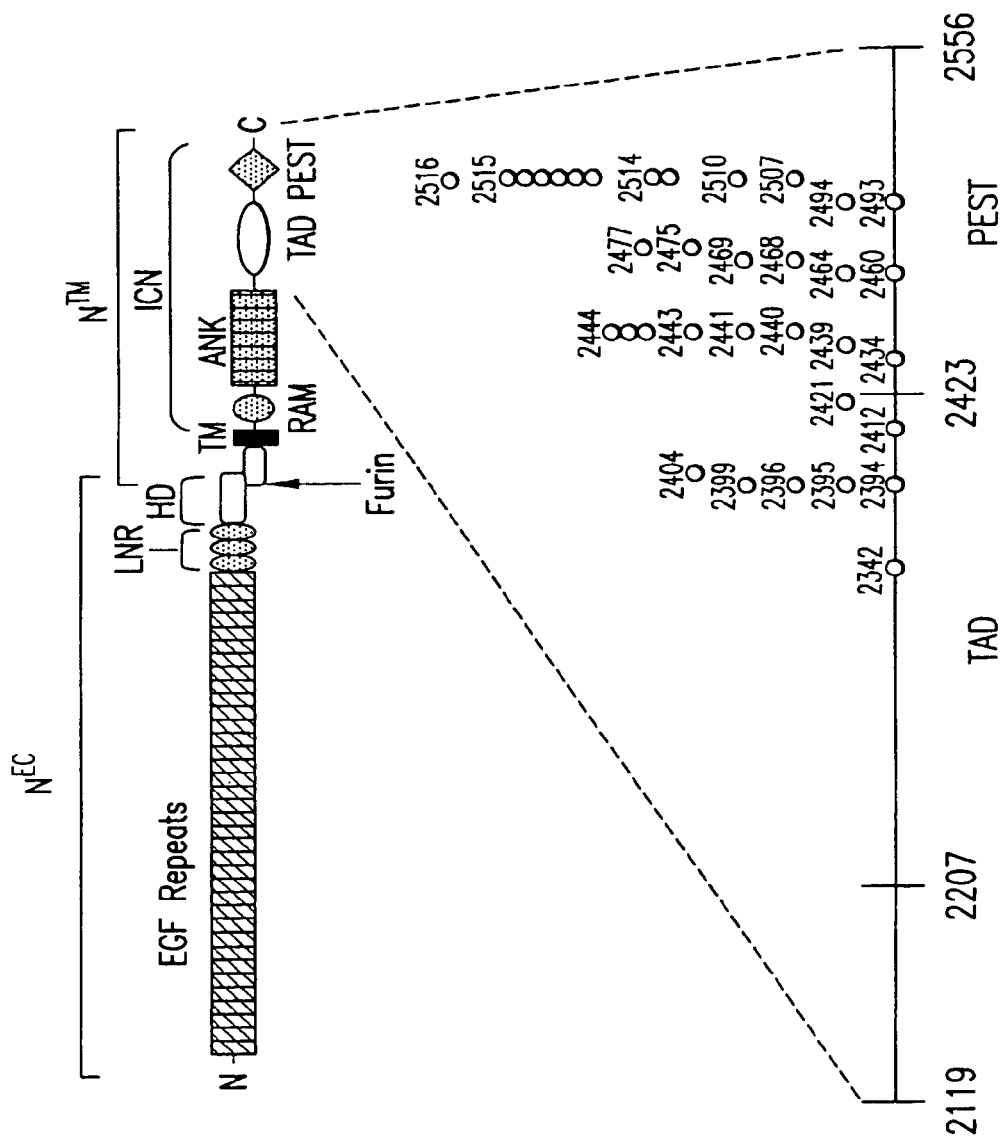
Figure 3F:
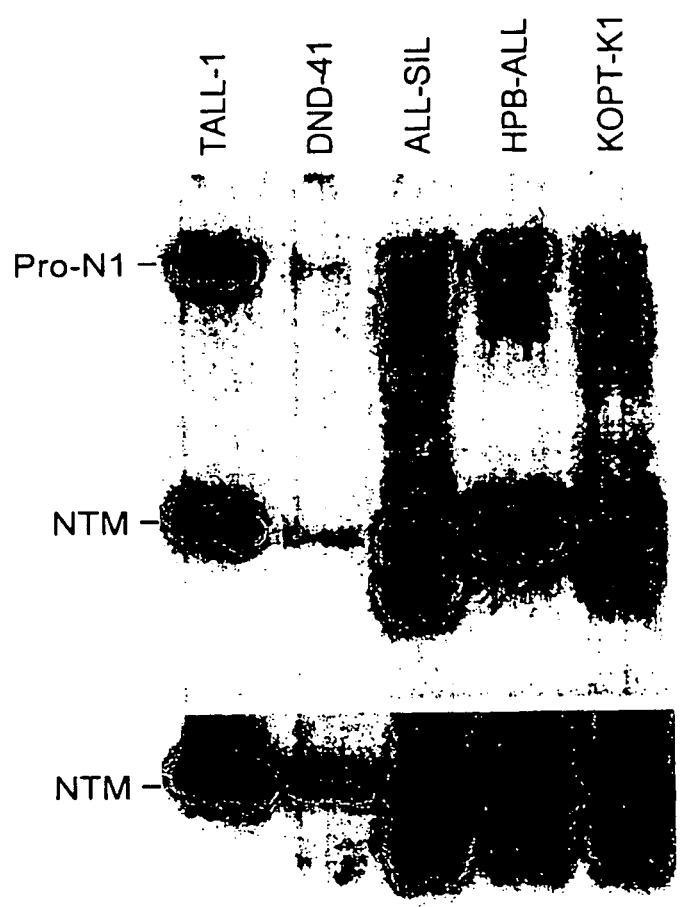

The PEST mutations (found in exon 34) were short insertions or deletions causing shifts in reading frame that are predicted to result in partial or complete deletion of the negative regulatory, C-terminal PEST domain (FIGS. 3D and 3E). PCR amplification, cloning, and sequencing of cDNAs revealed that the HD domain and PEST domain mutations lay in cis in the same NOTCH-1 allele in each of the 4 cell lines tested. Normal NOTCH-1 cDNA clones were also identified in each cell line, indicating that both alleles are expressed. This is consistent with the results of Western blot analysis (FIG. 3F), which revealed that cell lines with exon 26 and 34 mutations contained a polypeptide of the expected size of NTM and additional aberrant polypeptides of slightly smaller size than NTM. In contrast, the cell line TALL-1, which lacks mutations in exons 26 and 34, contained only NOTCH-1 polypeptides of the expected sizes.

We extended our mutational analysis of the HD and PEST domains of NOTCH-1 to cryopreserved primary T-ALL samples obtained from the bone marrow of ninety-six children and adolescents at the time of diagnosis. At least one mutation was identified in 49 tumors (51%); 20 tumors (20.8%) had HD domain mutations only, 15 tumors (15.6%) had PEST domain mutations only, and 14 tumors (14.6%) had mutations in both the HD and PEST domains. Mutations were seen in tumors associated with mis-expression of HOX11 (2 of 3 cases), HOX11L2 (10 of 13, or 77%), TAL1 (11 of 31, or 35%), LYL1 (7 of 14, or 50%), MLL-ENL (1 of 3), or CALM-AF10 (1 of 2), which together define the major molecular subtypes of T-ALL. The HD domain mutations in primary tumors were clustered in a "hotspot" spanning residues 1574-1622, and included each of the three L to P missense mutations originally identified in the NOTCH-dependent T-ALL cell lines, as well as deletions of 1-2 residues and short "in-frame" insertions (FIG. 3A-B). PEST domain mutations included insertions or deletions that induced a shift in reading frame, as well as point mutations that created premature stop codons (FIG. 3D-E, and FIG. 6).

In contrast to T-ALLs, no mutations were observed in 89 primary B-ALL samples. Mutations were also absent from four remission bone marrow samples obtained from patients whose T-ALLs harbored NOTCH-1 mutations, indicating that these mutations are not present in the germline, but rather acquired within the malignant clones. Polymorphisms have not been detected within the HD domain region of NOTCH-1 (NCBI SNP database), leading us to further suspect that the mutations in conserved residues we detected in T-ALLs were likely to have functional consequences.

Figure 4A:
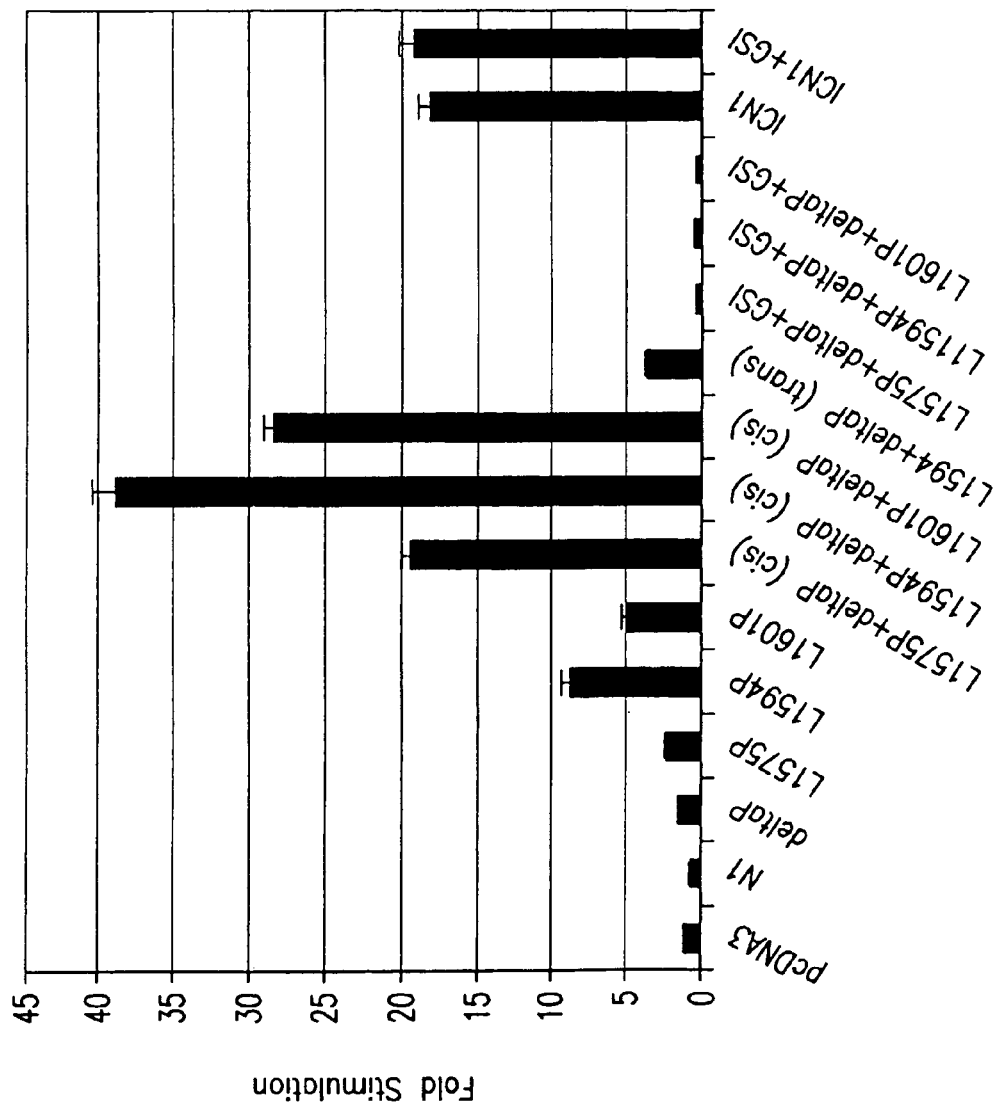
FIG. 4A-4B. HD and PEST domain mutations activate NOTCH-1 signaling synergistically. (4A) Reporter gene assays. U2OS cells were transiently co-transfected in 24-well format with the indicated pcDNA3 plasmids, a NOTCH-responsive luciferase reporter gene, and an internal Renilla luciferase internal control plasmid, as described previously (Aster, et al., *Mol. Cell. Biol.* 20:7505-15). Twenty-five ng of pcDNA3 plasmid was used per well, except for experiments with pcDNA3-ICN1, in which 5 ng of plasmid per well were used. Normalized luciferase activities in whole cell lysates were determined in triplicate and expressed relative to the activity in lysates prepared from cells transfected with the empty vector control. (4B) Model for synergistic NOTCH-1 activation by dual mutations involving both the HD and PEST domains.

To address this issue directly, we studied the effects of common HD domain mutations, with and without a PEST domain deletion, on activation of a NOTCH-sensitive luciferase reporter gene in transient expression assays (FIG. 4A). Single L to P mutations within the HD domain at residues 1575, 1594, or 1601 caused a 3-9-fold stimulation of luciferase activity, while an isolated PEST deletion (corresponding to the mutation found in the ALL-SIL cell line that produces a truncation at amino acid 2471) resulted in an approximate 1.5-2-fold stimulation. More strikingly, each HD mutation and the same PEST domain truncation in cis resulted in 20-40-fold stimulations of transcriptional activation. In contrast, the same mutations in trans produced lower levels of stimulation that were close to the average of each mutation acting alone.

Additional reporter gene assays carried out as described in FIG. 4 have proven that all HD mutations tested to date convey increased function on NOTCH-1. The mutations tested in these functional assays are:

| | |
|---|---|
| V1577E | Sequence ID NO: 102 |
| L1586Q | Sequence ID NO: 106 |
| F1593S | Sequence ID NO: 117 |
| L1597H | Sequence ID NO: 109 |
| R1599P | Sequence ID NO: 15 |
| I1617N | Sequence ID NO: 115 |
| I1617T | Sequence ID NO: 116 |
| V1677D | Sequence ID NO: 135 |
| L1679P | Sequence ID NO: 71 |
| I1681N | Sequence ID NO: 73 |
| A1702P | Sequence ID NO: 129 |
| I1719T | Sequence ID NO: 128 |
| ins(RLGSLNIPYKIEAV) | Sequence ID NO: 137 |

These data suggest that increased function will be a general feature of mutations found in the HD domain of NOTCH1.

Figure 4B:
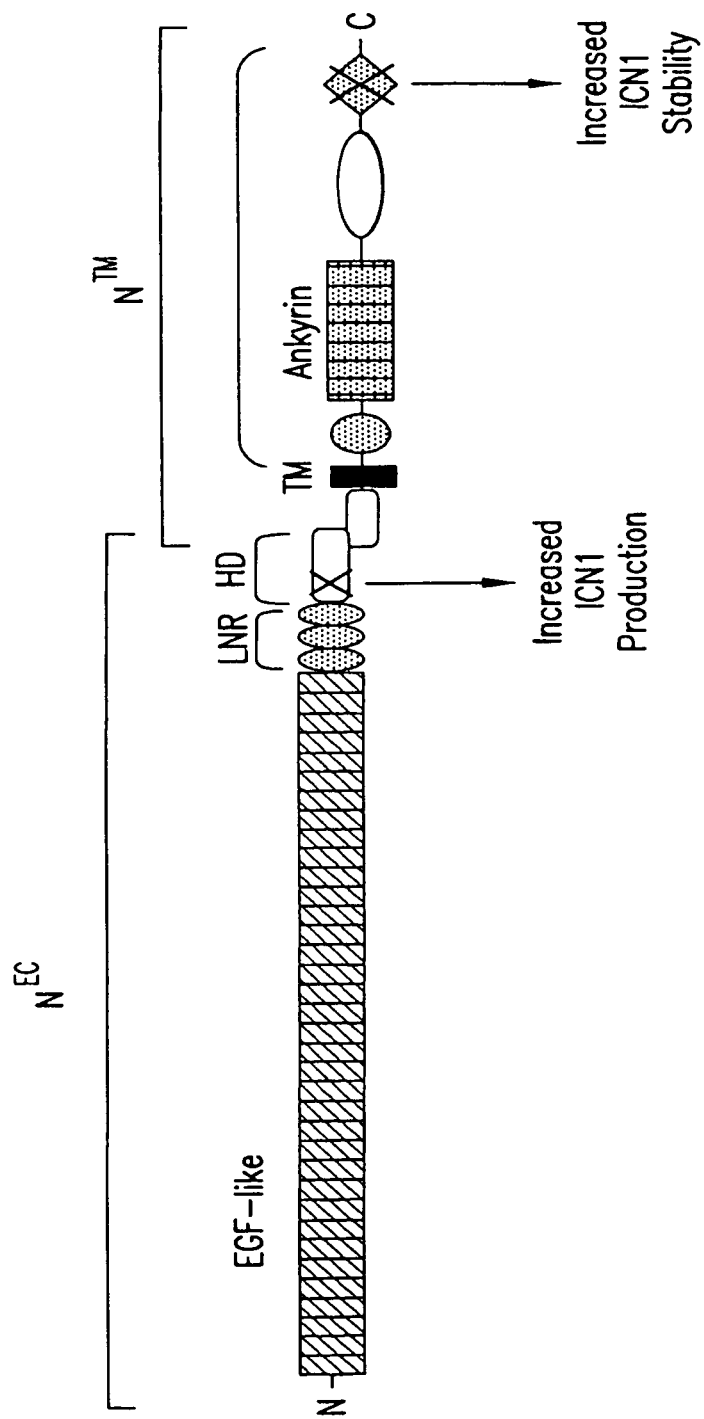

The synergistic interaction of HD and PEST domain mutations in cis is consistent with a model in which (i) HD domain mutations enhance γ-secretase cleavage and increase the rate of production of ICN1, and (ii) truncations removing the PEST domain of ICN1 increase the half-life of this activated form of NOTCH (FIG. 4B). The intermediate levels of activation produced by these mutations in trans presumably reflect competition between relatively weak and strong gain-of-function NOTCH-1 polypeptides for factors required for processing and signaling. The stimulatory effects of mutated transmembrane NOTCH-1 polypeptides were completely abrogated by a γ-secretase inhibitor, indicating a requirement for proteolysis at the juxtamembrane site of mutated NTM subunits for signal transduction (FIG. 4A). In contrast, the stimulation produced by ICN1, which is constitutively nuclear, was unaffected by γ-secretase inhibition (FIG. 4A).

More recently we have observed two mutations in tumors other than T-ALL. An insertional mutation in exon 26 of NOTCH-1 was found in a case of acute myelogenous leukemia that causes amino acid residues 1593-1594 to be changed from FL to LSL. This mutation stimulates the ability of NOTCH-1 to activate a CSL-sensitive luciferase gene in assays analogous to those shown in FIG. 4A, indicating that it increases NOTCH-1 function. A novel NOTCH-1 mutation in exon 27 was found in a case of Langerhans cell histiocytosis, in which a highly conserved residue, amino acid 1693, was changed from a C to an R. Together, these data support the prediction that mutations identical or functionally similar to those discovered in T-ALL will be found in other forms of human neoplasia.

Discussion

The prevalence of gain-of-function NOTCH-1 mutations, which are found in every major molecular oncogenic subtype of T-ALL, strongly supports a pre-eminent role for upregulated NOTCH signaling in the pathogenesis of this tumor. The existence of at least one cell line, TALL-1, that apparently requires NOTCH signals for growth, yet lacks NOTCH-1 HD domain and PEST region mutations, suggests that other mechanisms exist that account for pre-T cell transformation involving the NOTCH pathway. It is conceivable that activating mutations affecting other regions of NOTCH-1 may be identified in human T-ALL cases.

Prior work has shown that activation of NOTCH receptors is achieved primarily through release of the NEC subunit (Rand, et al., *Mol. Cell. Biol.* 20:1825-35; Kramer, *Sci. STKE* 2000, PE1), which normally represses proteolysis. Recombinant "mini-receptors" consisting of just the NEC HD domain and the extracellular portion of NTM form stable heterodimers after furin cleavage, indicating that critical inter-subunit contacts lie in these regions. Hence, HD domain mutations may act by destabilizing NEC/NTM heterodimers.

It follows that similar effects might be imparted by mutations occurring in the analogous heterodimerization region of the NTM subunit.

Several factors may explain the high frequency of NOTCH-1 mutations in T-ALL. The absolute requirement for NOTCH-1 signals during several stages of normal early T cell development provides a functional basis for the frequent involvement of this pathway. Further, unlike the t(7;9), which is created by aberrant recombination during attempted V-D-Jβ rearrangement in committed T cell progenitors, the more common point mutations and insertions described here could occur in multipotent hematopoietic progenitors, which also normally express NOTCH-1 (Calvi, et al., *Nature* 425, 841-6). If so, such mutations would be predicted to induce daughter cells to adopt a T cell fate (Allman, et al., *J. Exp. Med.* 194:99-106) and thereby increase the pool of cells that are at risk for additional leukemogenic events, which could include additional mutations affecting the same NOTCH-1 allele, as well as the chromosomal, genetic and epigenetic events that lead to the mis-expression of other critical transcription factors. Analogous NOTCH mutations might be involved in the molecular pathogenesis of certain more common types of human cancer, as NOTCH receptors are expressed in many normal tissues and a variety of malignancies (Allenspach, et al., *Cancer Biol. Ther.* 1:466-76).

Our findings identify the NOTCH pathway as a rational target for molecular therapy in T-ALL. Although approximately 75% of patients are currently cured of this disease with very intensive and cytotoxic chemotherapy regimens (Pui, et al., *N. Engl. J. Med.* 350:1535-48), new therapies are needed for patients with refractory disease, and less toxic, more efficacious combinations of drugs would be beneficial to all T-ALL patients. The development of potent, specific inhibitors of γ-secretase (Wolfe, *Nat. Rev. Drug Discov.* 1:859-66), due to the involvement of this protease in the pathogenesis of Alzheimer's disease, should expedite clinical trials of cancer therapies aimed at blocking NOTCH-1 activity.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of treating a patient for T-cell acute lymphoblastic leukemia (T-ALL) comprising: administering an effective amount of a gamma-secretase inhibitor to said patient, wherein prior to treatment, said patient has been found to have cancer cells with a mutant NOTCH-1 receptor comprising the amino acid sequence of SEQ ID NO:1 except for one or more mutations which:
 a) are associated with increased receptor signaling in response to gamma-secretase, and
 b) are in the region of SEQ ID NO:1 from amino acid 2311 to amino acid 2556.

2. The method of claim 1, wherein, except for said one or more mutations, said mutant NOTCH-1 receptor consists of the amino sequence of SEQ ID NO:1.

3. The method of claim 1, wherein said gamma-secretase inhibitor is selected from the group consisting of: III-31-C; N-[N-(3,5-difluorophenacetyl)-L-alanyl]S-phenylglycine t-butyl ester) (DAPT); compound E; D-helical peptide 294; isocoumarins; BOC-Lys(Cbz)Ile-Leu-epoxide; and (Z-LL)$_2$-ketone.

4. The method of claim 3, wherein, except for said one or more mutations, said mutant NOTCH-1 receptor consists of the amino sequence of SEQ ID NO:1.

5. A method of treating a patient for T-cell acute lymphoblastic leukemia (T-ALL) comprising: administering an effective amount of a gamma-secretase inhibitor to said patient, wherein prior to treatment, said patient has been found to have cancer cells with a mutant NOTCH-1 receptor comprising the amino acid sequence of SEQ ID NO:1 except that the portion of said amino acid sequence from amino acid 2311 to amino acid 2556 is replaced with a sequence selected from the group consisting of: SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; SEQ ID NO:58; SEQ ID NO:59; SEQ ID NO:138; SEQ ID NO:139; SEQ ID NO:140; SEQ ID NO:141; SEQ ID NO:142; SEQ ID NO:143; and SEQ ID NO:144.

6. The method of claim 5, wherein, except for the replacement of the portion of said amino acid sequence from amino acid 2311 to amino acid 2556, said mutant NOTCH-1 receptor consists of the amino sequence of SEQ ID NO:1.

7. The method of claim 5, wherein said gamma-secretase inhibitor is selected from the group consisting of: III-31-C; N-[N-(3,5-difluorophenacetyl)-L-alanyl]S-phenylglycine t-butyl ester) (DAPT); compound E; D-helical peptide 294; isocoumarins; BOC-Lys(Cbz)Ile-Leu-epoxide; and (Z-LL)$_2$-ketone.

8. The method of claim 7, wherein, except for said one or more mutations, said mutant NOTCH-1 receptor consists of the amino sequence of SEQ ID NO:1.

9. The method of claim 5, wherein, in addition to the replacement of the sequence of SEQ ID NO:1 from amino acid 2311 to amino acid 2556 in said mutant NOTCH-1 receptor, the portion of the amino acid sequence of SEQ ID NO:1 from amino acid 1571 to amino acid 1618 is replaced with a sequence selected from the group consisting of: SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:102; SEQ ID NO:103; SEQ ID NO:104; SEQ ID NO:105; SEQ ID NO:106; SEQ ID NO:107; SEQ ID NO:108; SEQ ID NO:109; SEQ ID NO:110; SEQ ID NO:111; SEQ ID NO:112; SEQ ID NO:113; SEQ ID NO:114; SEQ ID NO:115; SEQ ID NO:116; SEQ ID NO:117; SEQ ID NO:118; and SEQ ID NO:145.

10. The method of claim 9, wherein, except for the replacement of the sequence of SEQ ID NO:1 from amino acid 2311 to amino acid 2556 and for the replacement of the sequence from amino acid 1571 to amino acid 1618, said mutant NOTCH-1 receptor consists of the amino sequence of SEQ ID NO:1.

11. The method of claim 9, wherein said gamma-secretase inhibitor is selected from the group consisting of: III-31-C; N-[N-(3,5-difluorophenacetyl)-L-alanyl]S-phenylglycine t-butyl ester) (DAPT); compound E; D-helical peptide 294; isocoumarins; BOC-Lys(Cbz)Ile-Leu-epoxide; and (Z-LL)$_2$-ketone.

12. The method of claim 5, wherein, in addition to the replacement of the sequence of SEQ ID NO:1 from amino acid 2311 to amino acid 2556 in said mutant NOTCH-1 receptor, the portion of the amino acid sequence of SEQ ID NO:1 from amino acid 1571 to amino acid 1622 is replaced with a sequence selected from the group consisting of: SEQ ID NO:23; SEQ ID NO:24; SEQ ID NO:25; SEQ ID NO:26; SEQ ID NO:27; SEQ ID NO:28; SEQ ID NO:29; SEQ ID NO:119; SEQ ID NO:120; SEQ ID NO:121; SEQ ID NO:122; SEQ ID NO:123; SEQ ID NO:124; SEQ ID NO:125; SEQ ID NO:126; and SEQ ID NO:127.

13. The method of claim 12, wherein, except for the replacement of the sequence of SEQ ID NO:1 from amino acid 2311 to amino acid 2556 and for the replacement of the sequence from amino acid 1571 to amino acid 1622, said mutant NOTCH-1 receptor consists of the amino sequence of SEQ ID NO:1.

14. The method of claim 12, wherein said gamma-secretase inhibitor is selected from the group consisting of: III-31-C; N-[N-(3,5-difluorophenacetyl)-L-alanyl]S-phenylglycine t-butyl ester) (DAPT); compound E; D-helical peptide 294; isocoumarins; BOC-Lys(Cbz)Ile-Leu-epoxide; and (Z-LL)$_2$-ketone.

15. The method of claim 5, wherein, in addition to the replacement of the sequence of SEQ ID NO:1 from amino acid 2311 to amino acid 2556 in said mutant NOTCH-1 receptor, the portion of the amino acid sequence of SEQ ID NO:1 from amino acid 1674 to amino acid 1730 is replaced with a sequence selected from the group consisting of: SEQ ID NO:70; SEQ ID NO:71; SEQ ID NO:72; SEQ ID NO:73; SEQ ID NO:74; SEQ ID NO:75; SEQ ID NO:128; SEQ ID NO:129; SEQ ID NO:130; SEQ ID NO:131; SEQ ID NO:132; SEQ ID NO:133; SEQ ID NO:134; SEQ ID NO:135; SEQ ID NO:136; and SEQ ID NO:137.

16. The method of claim 15, wherein, except for the replacement of the sequence of SEQ ID NO:1 from amino acid 2311 to amino acid 2556 and for the replacement of the sequence from amino acid 1674 to amino acid 1730, said mutant NOTCH-1 receptor consists of the amino sequence of SEQ ID NO:1.

17. The method of claim 15, wherein said gamma-secretase inhibitor is selected from the group consisting of: III-31-C; N-[N-(3,5-difluorophenacetyl)-L-alanyl]S-phenylglycine t-butyl ester) (DAPT); compound E; D-helical peptide 294; isocoumarins; BOC-Lys(Cbz)Ile-Leu-epoxide; and (Z-LL)$_2$-ketone.

18. The method of claim 5, wherein in addition to the replacement of the sequence of SEQ ID NO:1 from amino acid 2311 to amino acid 2556 in said mutant NOTCH-1 receptor, said mutant NOTCH-1 receptor is mutated at one or more amino acid positions selected from the group consisting of: 1571; 1573; 1575; 1576; 1578; 1579; 1583; 1586; 1588; 1590; 1593; 1594; 1595; 1598; 1600-1607; 1610-1618; 1674; 1675; 1677; 1679-1684; 1686; 1695; 1696; 1703; 1706; 1715; 1720; 1725; and 1728.

19. The method of claim 18, wherein, except for the replacement of the sequence of SEQ ID NO:1 from amino acid 2311 to amino acid 2556 and for the mutation of one or more amino acid positions selected from the group consisting of: 1571; 1573; 1575; 1576; 1578; 1579; 1583; 1586; 1588; 1590; 1593; 1594; 1595; 1598; 1600-1607; 1610-1618; 1674; 1675; 1677; 1679-1684; 1686; 1695; 1696; 1703; 1706; 1715; 1720; 1725; and 1728, said mutant NOTCH-1 receptor consists of the amino sequence of SEQ ID NO:1.

20. The method of claim 18, wherein said gamma-secretase inhibitor is selected from the group consisting of: III-31-C; N-[N-(3,5-difluorophenacetyl)-L-alanyl]S-phenylglycine t-butyl ester) (DAPT); compound E; D-helical peptide 294; isocoumarins; BOC-Lys(Cbz)Ile-Leu-epoxide; and (Z-LL)$_2$-ketone.

* * * * *